(12) United States Patent
Shim et al.

(10) Patent No.: US 10,709,697 B2
(45) Date of Patent: Jul. 14, 2020

(54) BIS-AMINES, COMPOSITIONS, AND USES RELATED TO CXCR4 INHIBITION

(71) Applicants: Emory University, Atlanta, GA (US); Georgia State University Research Foundation, Inc., Atlanta, GA (US)

(72) Inventors: Hyunsuk Shim, Atlanta, GA (US); Suazette Reid Mooring, Ellenwood, GA (US); Renren Bai, Atlanta, GA (US)

(73) Assignees: Emory University, Atlanta, GA (US); Georgia State University Research Foundation, Inc., Atlanta, GA (US)

( * ) Notice: Subject to any disclaimer, the term of this patent is extended or adjusted under 35 U.S.C. 154(b) by 0 days.

(21) Appl. No.: 15/745,291

(22) PCT Filed: Jul. 13, 2016

(86) PCT No.: PCT/US2016/042021
§ 371 (c)(1),
(2) Date: Jan. 16, 2018

(87) PCT Pub. No.: WO2017/011517
PCT Pub. Date: Jan. 19, 2017

(65) Prior Publication Data
US 2019/0008840 A1  Jan. 10, 2019

Related U.S. Application Data

(60) Provisional application No. 62/193,367, filed on Jul. 16, 2015.

(51) Int. Cl.
| | | |
|---|---|---|
| *A61K 31/444* | (2006.01) | |
| *C07D 333/20* | (2006.01) | |
| *C07C 211/27* | (2006.01) | |
| *C07D 405/14* | (2006.01) | |
| *C07D 401/14* | (2006.01) | |
| *C07D 213/53* | (2006.01) | |
| *C07C 217/58* | (2006.01) | |
| *C07C 211/53* | (2006.01) | |
| *C07D 307/52* | (2006.01) | |
| *C07D 241/12* | (2006.01) | |
| *C07C 211/29* | (2006.01) | |
| *A61P 31/18* | (2006.01) | |
| *A61P 35/02* | (2006.01) | |
| *A61P 29/00* | (2006.01) | |
| *A61K 31/5377* | (2006.01) | |

(52) U.S. Cl.
CPC ........ *A61K 31/444* (2013.01); *A61K 31/5377* (2013.01); *A61P 29/00* (2018.01); *A61P 31/18* (2018.01); *A61P 35/02* (2018.01); *C07C 211/27* (2013.01); *C07C 211/29* (2013.01); *C07C 211/53* (2013.01); *C07C 217/58* (2013.01); *C07D 213/53* (2013.01); *C07D 241/12* (2013.01); *C07D 307/52* (2013.01); *C07D 333/20* (2013.01); *C07D 401/14* (2013.01); *C07D 405/14* (2013.01); *A61K 2300/00* (2013.01); *C07C 2601/02* (2017.05)

(58) Field of Classification Search
None
See application file for complete search history.

(56) References Cited

U.S. PATENT DOCUMENTS

| | | |
|---|---|---|
| 6,872,714 B1 | 3/2005 | Schols |
| 7,291,631 B2 | 11/2007 | Bridger |
| 7,354,899 B2 | 4/2008 | Clark-Lewis |
| 7,682,611 B2 | 3/2010 | Hanai |
| 8,008,312 B2 | 8/2011 | Shim |
| 8,114,884 B2 | 2/2012 | Shim |
| 9,545,453 B2 | 1/2017 | Oupicky |
| 2005/0002939 A1 | 1/2005 | Zlotnik |
| 2007/0054930 A1 | 3/2007 | Shim |
| 2007/0275965 A1 | 11/2007 | Thomas |
| 2010/0204219 A1 | 8/2010 | Garcia |

(Continued)

FOREIGN PATENT DOCUMENTS

| | | |
|---|---|---|
| CA | 2707418 | 5/2009 |
| EP | 0287465 | 10/1988 |
| EP | 1541585 | 6/2005 |

(Continued)

OTHER PUBLICATIONS

α, α'-dianilino-p-xylene, https://pubchem.ncbi.nlm.nih.gov/compound/607368#section=IUPAC-name, accessed Mar. 19, 2019, create date Mar. 27, 2005, attached as PDF (Year: 2005).*
Zawilska. Pharmacological Reports, 2013, 65, 1-14 (Year: 2013).*
Grau. Inorganic Chemistry, 2013, 52, 11867-11874 (Year: 2013).*
Takashima. Chemistry: A European Journal, 2014, 20, 2184-2192 (Year: 2014).*
Bai. European Journal of Medicinal Chemistry, 2016, 118, 340-350 (Year: 2016).*
Bai et al. Symmetrical bis-tertiary amines as novel CXCR4 inhibitors. European journal of medicinal chemistry, 2016, 118, 340-350.
Bai et al. Development of CXCR4 modulators based on the lead compound RB-108, European Journal of Medicinal Chemistry 173 (2019) 32e43.

(Continued)

*Primary Examiner* — Noble E Jarrell
(74) *Attorney, Agent, or Firm* — Emory Patent Group

(57) ABSTRACT

This disclosure relates bis-amine compounds disclosed herein and uses related to CXCR4 inhibition. In certain embodiments, the compounds have formula (I), salts, derivatives, and prodrugs thereof wherein, A is a bridging aryl or heterocyclyl and $R^1$ and $R^2$ are further disclosed herein. In certain embodiments, the disclosure contemplates pharmaceutical compositions comprising compounds disclosed herein. In certain embodiments, the disclosure relates to methods of treating or preventing CXCR4 related diseases or conditions by administering an effective amount of a compound disclosed herein to a subject in need thereof.

13 Claims, 4 Drawing Sheets

(56) References Cited

U.S. PATENT DOCUMENTS

2011/0245265 A1  10/2011  Zuk
2014/0248236 A1  9/2014  Natchus

FOREIGN PATENT DOCUMENTS

| EP | 1739085 | 1/2007 |
|---|---|---|
| WO | 2001085196 | 11/2001 |
| WO | 2004087068 | 10/2004 |
| WO | 2012049277 | 4/2012 |
| WO | 2013052585 | 4/2013 |

OTHER PUBLICATIONS

Garcia et al. Synthsis of thiophene analogs as potential antagonists of Chemokine Receptor Type 4 (CXCR4) Poster Presentation #32B,2014.
Liang et al. Development of a Unique Small Molecule Modulator of CXCR4. (2012) PLoS One 7(4): e34038.
Mooring et al. Synthesis of pyridine derivatives as potential antagonists of chemokine receptor type 4, Heterocycl Comm. 2014, 20(3): 149-153.
Mukherjee et al. The Role of chemokine receptor CXCR4 in breast cancer metastasis, Am J Cancer Res 2013;3(1):46-57.
Wiley et al. Alkylidene- and Arylideneaminomorpholines, J. Org. Chem.1959, 24(11) 1784-1786.
Zhan et al. Discovery of Small Molecule CXCR4 Antagonists, J. Med. Chem. 2007, 50, 5655-5664.
Zhu et al. AMD3100 inhibits epithelial-mesenchymal transition, cell invasion, and metastasis in the liver and the lung through blocking the SDF-1α/CXCR4 signaling pathway in prostate cancer, J Cell Physiol. 2019, 234:11746-11759.

* cited by examiner

BIS-AMINES, COMPOSITIONS, AND USES RELATED TO CXCR4 INHIBITION

CROSS-REFERENCE TO RELATED APPLICATIONS

This application is the National Stage of International Application No. PCT/US2016/042021 filed Jul. 13, 2016, which claims the benefit of priority to U.S. Provisional Application No. 62/193,367 filed Jul. 16, 2015. The entirety of each of these applications is hereby incorporated by reference for all purposes.

STATEMENT REGARDING FEDERALLY FUNDED RESEARCH

This invention was made with government support under Grant R01 CA165306 awarded by the NIH NCI. The government has certain rights in the invention.

BACKGROUND

C—X—C chemokine receptor type 4 (CXCR4), also known as fusin or cluster of differentiation 184 (CD184), is a seven transmembrane G-protein coupled receptor (GPCR) belonging to the Class I GPCR or rhodopsin-like GPCR family. Stromal-derived-factor-1 (SDF-1) or C—X—C chemokine ligand 12 (CXCL12) is the major ligand of CXCR4 and the interaction recognition between CXCL12 and CXCR4 recruits cells to the organ sites with high levels of CXCL12 expression. The CXCL12/CXCR4 axis has been shown to be involved in a number of pathological conditions, including cancer and inflammation. CXCR4 plays a role as a homing receptor to the lymph nodes, lung, liver, and bone. Homing, the mechanism that allows foreign tissue-origin cells to reside and proliferate, is believed to be the rate-limiting step of the multi-step metastatic process. CXCR4 is overexpressed in many human cancer types, such as breast, leukemia, lung, and prostate cancers.

Inflammation is inextricably associated with primary tumor progression and contributes to metastatic outgrowth in distant organs. The COX pathway has long been used as the major target for anti-inflammatory drugs. Both traditional non-steroidal anti-inflammatory drugs (NSAIDs) and selective COX-2 inhibitors exhibit their anti-inflammatory activity by inhibiting COX-2. Nevertheless, the prolonged use of traditional anti-inflammatory drugs is associated with potential serious side effects such as kidney failure, ulcers and prolonged bleeding after an injury or surgery. Furthermore, rofecoxib and valdecoxib were withdrawn from the market due to an increased risk of cardiovascular complications.

Accumulating evidence suggests the involvement of CXCR4CXCL12 interaction in various inflammatory diseases, including rheumatoid arthritis, autoimmune diseases, ischemic injuries, inflammatory bowel disease, and pneumonia. Based on these findings, development of inhibitors blocking CXCR4 presents a new avenue for complementary therapeutic strategy in inflammatory diseases as well as cancer.

AMD3100 is a CXCR4 inhibitor approved by FDA for stem cell mobilization. Although it benefits patients with certain diseases, long term treatment can introduce lung and liver fibrosis. Hence there is a need to develop improved CXCR4 inhibitors.

Mooring et al. report pyridine derivatives as potential antagonists of chemokine receptor type 4, Heterocyclic communications, 2014, 20(3):149-153. Zhu et al. report dipyrimidine amines as chemokine receptor type 4 antagonists. J. Med. Chem., 53 (2010), pp. 8556-8568. See also Zhan et al., J. Med. Chem., 50 (2007), pp. 5655-5664, U.S. Pat. Nos. 8,008,312 and 8,114,884.

Liang et al. report a small molecule modulator of CXCR4. PLoS One 2012, 7 (4), e34038.

Bai et al. report symmetrical bis-tertiary amines as CXCR4 inhibitors. Eur J Med Chem 2016, 118, 340-350.

References cited herein are not an admission of prior art.

SUMMARY

The disclosure relates bis-amine compounds disclosed herein and uses related to CXCR4 inhibition. In certain embodiments, the compounds have formula I,

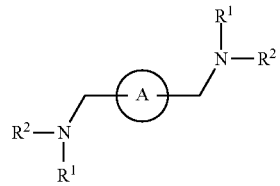

Formula I salts, derivatives, and prodrugs thereof wherein, A is an bridging aryl or heterocyclyl and $R^1$ and $R^2$ are further disclosed herein. In certain embodiments, the disclosure contemplates pharmaceutical compositions comprising compounds disclosed herein. In certain embodiments, the disclosure relates to methods of treating or preventing CXCR4 related diseases or conditions by administering an effective amount of a compound disclosed herein to a subject in need thereof.

In certain embodiments, the disclosure relates to a compound N,N'-(pyridine-2,6-diylbis(methylene))bis(N-methyl-1-(pyridin-2-yl)methanamine), salts, derivatives, or prodrugs thereof.

In certain embodiments, the disclosure relates to a compound 2,6-bis(morpholinomethyl)pyridine optionally substituted with one or more substituent, salts, derivatives, or prodrugs thereof.

In certain embodiments, the disclosure relates to a compound 2,6-bis(4-ethylanilinomethyl)pyridine optionally substituted with one or more substituent, salts, derivatives, or prodrugs thereof.

In certain embodiments, the disclosure relates to pharmaceutical composition comprising a compound disclosed herein or salt or derivative or prodrug thereof and a pharmaceutically acceptable excipient, diluent, or carrier. In certain embodiments, the pharmaceutical composition further comprise another active ingredient.

In certain embodiments, the disclosure relates to methods of treating or preventing an inflammatory condition comprising administering pharmaceutical composition comprising a compound disclosed herein to a subject in need thereof.

In certain embodiments, the disclosure relates to methods of treating or preventing cancer comprising administering pharmaceutical composition comprising a compound disclosed herein to a subject in need thereof.

In certain embodiments, the disclosure relates to methods of of treating or preventing cancer comprising administering pharmaceutical composition comprising a compound disclosed herein in combination with another anticancer agent to a subject in need thereof.

In certain embodiments, the disclosure relates to methods of of treating or preventing cancer comprising administering pharmaceutical composition comprising a compound disclosed herein in combination with another anticancer agent to a subject in need thereof.

In certain embodiments, the disclosure relates to methods of treating or preventing an viral infection comprising administering pharmaceutical composition comprising a compound disclosed herein to a subject in need thereof.

In certain embodiments, the disclosure relates to methods of treating or preventing an viral infection comprising administering pharmaceutical composition comprising a compound disclosed herein in combination with another antiviral agent to a subject in need thereof.

In certain embodiments, the disclosure relates to uses of a compound disclosed herein in the production of a medicament for the treatment of a CXCR4 related condition.

In certain embodiment, the disclosure relates to methods of making compounds disclosed herein comprising mixing a starting material disclosed herein with a reactant and/or reagents under conditions such that the products are formed.

DETAILED DISCUSSION

Figure 1A:
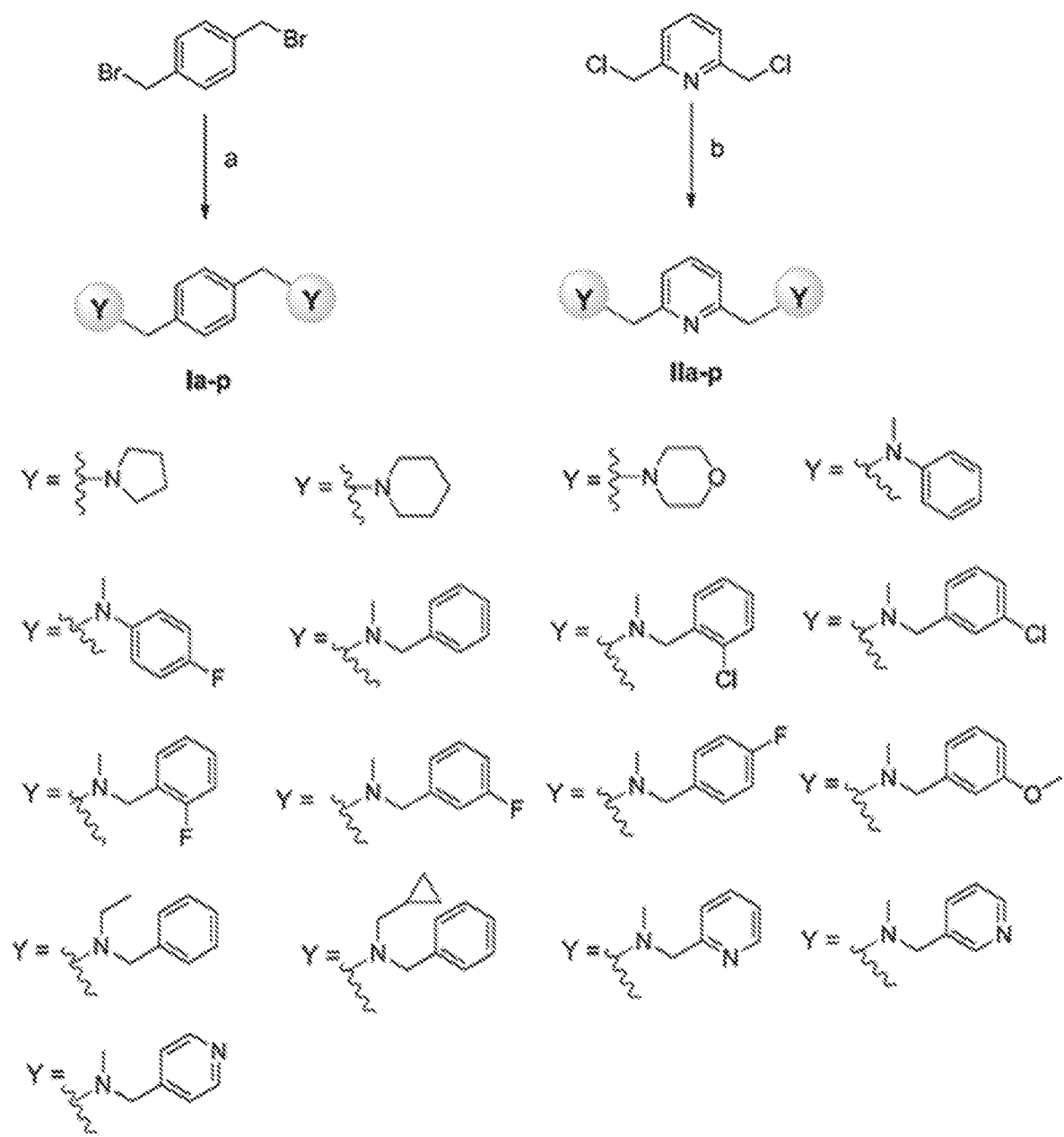
FIG. 1A illustrates the preparation of embodiments of this disclosure. Reagents and conditions to make our compounds: (a) $CH_3CN$, $K_2CO_3$, reflux, 3 h, 78-95%; (b) $CH_3CN$, $Cs_2CO_3$, reflux, 5 h, 70-90%.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, organic chemistry, biochemistry, molecular biology, pharmacology, and the like, which are within the skill of the art. Such techniques are explained fully in the literature.

It must be noted that, as used in the specification and the appended claims, the singular forms "a," "an," and "the" include plural referents unless the context clearly dictates otherwise. In this specification and in the claims that follow, reference will be made to a number of terms that shall be defined to have the following meanings unless a contrary intention is apparent.

Certain of the compounds described herein may contain one or more asymmetric centers and may give rise to enantiomers, diastereomers, and other stereoisomeric forms that can be defined, in terms of absolute stereochemistry at each asymmetric atom, as (R)- or (S)-. The present chemical entities, pharmaceutical compositions and methods are meant to include all such possible isomers, including racemic mixtures, tautomer forms, hydrated forms, optically substantially pure forms and intermediate mixtures.

Unless otherwise stated, structures depicted herein are also meant to include compounds which differ only in the presence of one or more isotopically enriched atoms. For example, compounds having the present structures except for the replacement or enrichment of a hydrogen by deuterium or tritium at one or more atoms in the molecule, or the replacement or enrichment of a carbon by $^{13}C$ or $^{14}C$ at one or more atoms in the molecule, are within the scope of this disclosure. In one embodiment, provided herein are isotopically labeled compounds having one or more hydrogen atoms replaced by or enriched by deuterium. In one embodiment, provided herein are isotopically labeled compounds having one or more hydrogen atoms replaced by or enriched by tritium. In one embodiment, provided herein are isotopically labeled compounds having one or more carbon atoms replaced or enriched by $^{13}C$. In one embodiment, provided herein are isotopically labeled compounds having one or more carbon atoms replaced or enriched by $^{14}C$.

The disclosure also embraces isotopically labeled compounds which are identical to those recited herein, except that one or more atoms are replaced by an atom having an atomic mass or mass number different from the atomic mass or mass number usually found in nature. Examples of isotopes that can be incorporated into disclosed compounds include isotopes of hydrogen, carbon, nitrogen, oxygen, phosphorus, sulfur, fluorine, and chlorine, such as, e.g., $^2H$, $^3H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. Certain isotopically-labeled disclosed compounds (e.g., those labeled with $^3H$ and/or $^{14}C$) are useful in compound and/or substrate tissue distribution assays. Tritiated (i.e., $^3H$) and carbon-14 (i.e., $^{14}C$) isotopes can allow for ease of preparation and detectability. Further, substitution with heavier isotopes such as deuterium (i.e., $^2H$) can afford certain therapeutic advantages resulting from greater metabolic stability (e.g., increased in vivo half-life or reduced dosage requirements). Isotopically labeled disclosed compounds can generally be prepared by substituting an isotopically labeled reagent for a non-isotopically labeled reagent. In some embodiments, provided herein are compounds that can also contain unnatural proportions of atomic isotopes at one or more of atoms that constitute such compounds. All isotopic variations of the compounds as disclosed herein, whether radioactive or not, are encompassed within the scope of the present disclosure.

As used herein, "alkyl" means a noncyclic straight chain or branched, unsaturated or saturated hydrocarbon such as those containing from 1 to 22 carbon atoms, while the term "lower alkyl" or "$C_{1-4}$alkyl" has the same meaning as alkyl but contains from 1 to 4 carbon atoms. The term "higher alkyl" has the same meaning as alkyl but contains from 8 to 22 carbon atoms. Representative saturated straight chain alkyls include methyl, ethyl, n-propyl, n-butyl, n-pentyl, n-hexyl, n-septyl, n-octyl, n-nonyl, and the like; while saturated branched alkyls include isopropyl, sec-butyl, isobutyl, tert-butyl, isopentyl, and the like. Unsaturated alkyls contain at least one double or triple bond between adjacent carbon atoms (referred to as an "alkenyl" or "alkynyl", respectively). Representative straight chain and branched alkenyls include ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like; while representative straight chain and branched alkynyls include acetylenyl, propynyl, 1-butynyl, 2-butynyl, 1-pentynyl, 2-pentynyl, 3-methyl-1-butynyl, and the like.

Non-aromatic mono or polycyclic alkyls are referred to herein as "carbocycles" or "carbocyclyl" groups. Representative saturated carbocycles include cyclopropyl, cyclobutyl, cyclopentyl, cyclohexyl, and the like; while unsaturated carbocycles include cyclopentenyl and cyclohexenyl, and the like.

"Heterocarbocycles" or heterocarbocyclyl" groups are carbocycles which contain from 1 to 4 heteroatoms independently selected from nitrogen, oxygen and sulfur which may be saturated or unsaturated (but not aromatic), monocyclic or polycyclic, and wherein the nitrogen and sulfur heteroatoms may be optionally oxidized, and the nitrogen heteroatom may be optionally quaternized. Heterocarbocycles include morpholinyl, pyrrolidinonyl, pyrrolidinyl, piperidinyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl, tetrahydrothiopyranyl, tetrahydropyrimidinyl, tetrahydrothiophenyl, tetrahydrothiopyranyl, and the like. "Aryl" means an aromatic carbocyclic monocyclic or polycyclic ring such as phenyl or naphthyl. Polycyclic ring systems may, but are not required to, contain one or more non-aromatic rings, as long as one of the rings is aromatic. "Arylalkyl" means an alkyl substituted with an aryl, e.g., benzyl, methyl substituted with phenyl.

As used herein, "heteroaryl" refers to an aromatic heterocarbocycle having 1 to 4 heteroatoms selected from nitrogen, oxygen and sulfur, and containing at least 1 carbon atom, including both mono- and polycyclic ring systems. Polycyclic ring systems may, but are not required to, contain one or more non-aromatic rings, as long as one of the rings is aromatic. Representative heteroaryls are furyl, benzofuranyl, thiophenyl, benzothiophenyl, pyrrolyl, indolyl, isoindolyl, azaindolyl, pyridyl, quinolinyl, isoquinolinyl, oxazolyl, isooxazolyl, benzoxazolyl, pyrazolyl, imidazolyl, benzimidazolyl, thiazolyl, benzothiazolyl, isothiazolyl, pyridazinyl, pyrimidinyl, pyrazinyl, triazinyl, cinnolinyl, phthalazinyl, and quinazolinyl. It is contemplated that the use of the term "heteroaryl" includes N-alkylated derivatives such as a 1-methylimidazol-5-yl substituent.

As used herein, "heterocycle" or "heterocyclyl" refers to mono- and polycyclic ring systems having 1 to 4 heteroatoms selected from nitrogen, oxygen and sulfur, and containing at least 1 carbon atom. The mono- and polycyclic ring systems may be aromatic, non-aromatic or mixtures of aromatic and non-aromatic rings. Heterocycle includes heterocarbocycles, heteroaryls, and the like.

"Alkylthio" refers to an alkyl group as defined above attached through a sulfur bridge. An example of an alkylthio is methylthio, (i.e., —S—$CH_3$).

"Alkoxy" refers to an alkyl group as defined above attached through an oxygen bridge.

Examples of alkoxy include, but are not limited to, methoxy, ethoxy, n-propoxy, i-propoxy, n-butoxy, s-butoxy, t-butoxy, n-pentoxy, and s-pentoxy. Preferred alkoxy groups are methoxy, ethoxy, n-propoxy, propoxy, n-butoxy, s-butoxy, and t-butoxy.

"Alkylamino" refers to an alkyl group as defined above attached through an amino bridge. An example of an alkylamino is methylamino, (i.e., —NH—$CH_3$).

"Alkanoyl" refers to an alkyl as defined above attached through a carbonyl bride (i.e., —(C=O)alkyl).

"Alkylsulfonyl" refers to an alkyl as defined above attached through a sulfonyl bridge (i.e., —S(=O)$_2$alkyl) such as mesyl and the like, and "Arylsulfonyl" refers to an aryl attached through a sulfonyl bridge (i.e., —S(=O)$_2$aryl).

"Alkylsulfinyl" refers to an alkyl as defined above attached through a sulfinyl bridge (i.e. —S(=O)alkyl).

"Aminoalkyl" refers to an amino group attached through an alkyl bridge. An example of an aminoalkyl is aminomethyl, (i.e., $NH_2$—$CH_2$—).

"Hydroxyalkyl" refers to a hydroxy group attached through an alkyl bridge. An example of a hydroxyalkyl is hydroxyethyl, (i.e., HO—$CH_2CH_2$—).

The term "substituted" refers to a molecule wherein at least one hydrogen atom is replaced with a substituent. When substituted, one or more of the groups are "substituents." The molecule may be multiply substituted. In the case of an oxo substituent ("=O"), two hydrogen atoms are replaced. Example substituents within this context may include halogen, hydroxy, alkyl, alkoxy, nitro, cyano, oxo, carbocyclyl, carbocycloalkyl, heterocarbocyclyl, heterocarbocycloalkyl, aryl, arylalkyl, heteroaryl, heteroarylalkyl, —NRaRb, —NRaC(=O)Rb, —NRaC(=O)NRaNRb, —NRaC(=O)ORb, —NRaSO2Rb, —C(=O)Ra, —C(=O)ORa, —C(=O)NRaRb, —OC(=O)NRaRb, —ORa, —SRa, —SORa, —S(=O)$_2$Ra, —OS(=O)$_2$Ra and —S(=O)$_2$ORa. Ra and Rb in this context may be the same or different and independently hydrogen, halogen hydroxyl, alkyl, alkoxy, alkyl, amino, alkylamino, dialkylamino, carbocyclyl, carbocycloalkyl, heterocarbocyclyl, heterocarbocycloalkyl, aryl, arylalkyl, heteroaryl, heteroarylalkyl.

The term "optionally substituted," as used herein, means that substitution is optional and therefore it is possible for the designated atom to be unsubstituted.

As used herein, "salts" refer to derivatives of the disclosed compounds where the parent compound is modified making acid or base salts thereof. Examples of salts include, but are not limited to, mineral or organic acid salts of basic residues such as amines, alkylamines, or dialkylamines; alkali or organic salts of acidic residues such as carboxylic acids; and the like. In typical embodiments, the salts are conventional nontoxic pharmaceutically acceptable salts including the quaternary ammonium salts of the parent compound formed, and non-toxic inorganic or organic acids. Preferred salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

"Subject" refers to any animal, preferably a human patient, livestock, rodent, monkey or domestic pet.

The term "prodrug" refers to an agent that is converted into a biologically active form in vivo. Prodrugs are often useful because, in some situations, they may be easier to administer than the parent compound. They may, for instance, be bioavailable by oral administration whereas the parent compound is not. The prodrug may also have improved solubility in pharmaceutical compositions over the parent drug. A prodrug may be converted into the parent drug by various mechanisms, including enzymatic processes and metabolic hydrolysis.

Typical prodrugs are pharmaceutically acceptable esters. Prodrugs include compounds wherein a hydroxy, amino or mercapto group is bonded to any group that, when the prodrug of the active compound is administered to a subject, cleaves to form a free hydroxy, free amino or free mercapto group, respectively. Examples of prodrugs include, but are not limited to, acetate, formate and benzoate derivatives of an alcohol or acetamide, formamide and benzamide derivatives of an amine functional group in the active compound and the like.

As used herein, "pharmaceutically acceptable esters" include, but are not limited to, alkyl, alkenyl, alkynyl, aryl, arylalkyl, and cycloalkyl esters of acidic groups, including, but not limited to, carboxylic acids, phosphoric acids, phosphinic acids, sulfonic acids, sulfinic acids, and boronic acids.

As used herein, the term "derivative" refers to a structurally similar compound that retains sufficient functional attributes of the identified analogue. The derivative may be structurally similar because it is lacking one or more atoms, substituted with one or more substituents, a salt, in different hydration/oxidation states, e.g., substituting a single or double bond, substituting a hydroxy group for a ketone, or because one or more atoms within the molecule are switched, such as, but not limited to, replacing an oxygen atom with a sulfur or nitrogen atom or replacing an amino group with a hydroxyl group or vice versa. Replacing a carbon with nitrogen in an aromatic ring is a contemplated derivative. The derivative may be a prodrug. Derivatives may be prepared by any variety of synthetic methods or appropriate adaptations presented in the chemical literature or as in synthetic or organic chemistry text books, such as those provide in March's Advanced Organic Chemistry: Reactions, Mechanisms, and Structure, Wiley, 6th Edition (2007) Michael B. Smith or Domino Reactions in Organic Synthesis, Wiley (2006) Lutz F. Tietze hereby incorporated by reference.

"Cancer" refers any of various cellular diseases with malignant neoplasms characterized by the proliferation of cells. It is not intended that the diseased cells must actually invade surrounding tissue and metastasize to new body sites. Cancer can involve any tissue of the body and have many different forms in each body area. Within the context of certain embodiments, whether "cancer is reduced" may be identified by a variety of diagnostic manners known to one skill in the art including, but not limited to, observation the reduction in size or number of tumor masses or if an increase of apoptosis of cancer cells observed, e.g., if more than a 5% increase in apoptosis of cancer cells is observed for a sample compound compared to a control without the compound. It may also be identified by a change in relevant biomarker or gene expression profile, such as PSA for prostate cancer, HER2 for breast cancer, or others.

The cancer to be treated in the context of the present disclosure may be any type of cancer or tumor. These tumors or cancer include, and are not limited to, tumors of the hematopoietic and lymphoid tissues or hematopoietic and lymphoid malignancies, tumors that affect the blood, bone marrow, lymph, and lymphatic system. Hematological malignancies may derive from either of the two major blood cell lineages: myeloid and lymphoid cell lines. The myeloid cell line normally produces granulocytes, erythrocytes, thrombocytes, macrophages and mast cells; the lymphoid cell line produces B, T, NK and plasma cells. Lymphomas, lymphocytic leukemias, and myeloma are from the lymphoid line, while acute and chronic myelogenous leukemia, myelodysplastic syndromes and myeloproliferative diseases are myeloid in origin.

A "chemotherapy agent," "chemotherapeutic," "anti-cancer agent" or the like, refer to molecules that are recognized to aid in the treatment of a cancer. Contemplated examples include the following molecules or derivatives such as temozolomide, carmustine, bevacizumab, procarbazine, lomustine, vincristine, gefitinib, erlotinib, cisplatin, carboplatin, oxaliplatin, 5-fluorouracil, gemcitabine, tegafur, raltitrexed, methotrexate, cytosine arabinoside, hydroxyurea, adriamycin, bleomycin, doxorubicin, daunomycin, epirubicin, idarubicin, mitomycin-C, dactinomycin, mithramycin, vinblastine, vindesine, vinorelbine, paclitaxel, taxol, docetaxel, etoposide, teniposide, amsacrine, topotecan, camptothecin, bortezomib, anagrelide, tamoxifen, toremifene, raloxifene, droloxifene, iodoxyfene, fulvestrant, bicalutamide, flutamide, nilutamide, cyproterone, goserelin, leuprorelin, buserelin, megestrol, anastrozole, letrozole, vorozole, exemestane, finasteride, marimastat, trastuzumab, cetuximab, dasatinib, imatinib, combretastatin, thalidomide, azacitidine, azathioprine, capecitabine, chlorambucil, cyclophosphamide, cytarabine, daunorubicin, doxifluridine, epothilone, irinotecan, mechlorethamine, mercaptopurine, mitoxantrone, pemetrexed, tioguanine, valrubicin and/or lenalidomide or combinations thereof such as cyclophosphamide, methotrexate, 5-fluorouracil (CMF); doxorubicin, cyclophosphamide (AC); mustine, vincristine, procarbazine, prednisolone (MOPP); sdriamycin, bleomycin, vinblastine, dacarbazine (ABVD); cyclophosphamide, doxorubicin, vincristine, prednisolone (CHOP); bleomycin, etoposide, cisplatin (BEP); epirubicin, cisplatin, 5-fluorouracil (ECF); epirubicin, cisplatin, capecitabine (ECX); methotrexate, vincristine, doxorubicin, cisplatin (MVAC).

As used herein, the terms "prevent" and "preventing" include the prevention of the recurrence, spread or onset. It is not intended that the present disclosure be limited to complete prevention. In some embodiments, the onset is delayed, or the severity of the disease is reduced.

As used herein, the terms "treat" and "treating" are not limited to the case where the subject (e.g., patient) is cured and the disease is eradicated. Rather, embodiments, of the present disclosure also contemplate treatment that merely reduces symptoms, and/or delays disease progression.

As used herein, the term "combination with" when used to describe administration with an additional treatment means that the agent may be administered prior to, together with, or after the additional treatment, or a combination thereof.

CXCR4 Inhibitory Compounds

In certain embodiments, this disclosure relates to bis-amines, salts, and derivatives thereof that are CXCR4 inhibitors. In certain embodiments, the compounds have the following formula:

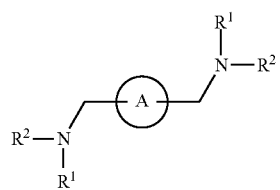

Formula I salts, derivatives, and prodrugs thereof wherein,

A is an bridging aryl or heterocyclyl;

$R^1$ is hydrogen, alkyl, formyl, carboxy, hydroxyalkyl, thioalkyl, aminoalkyl, alkanoyl, alkoxycarbonyl, alkylsulfinyl, alkyl sulfonyl, aryl sulfonyl, carbocyclyl, benozyl, benzyl, aryl, or heterocyclyl, wherein $R^1$ is optionally substituted with one or more, the same or different, $R^{10}$;

$R^2$ is alkyl, halogen, nitro, cyano, hydroxy, amino, mercapto, formyl, carboxy, carbamoyl, alkoxy, hydroxyalkyl, alkylthio, thioalkyl, alkylamino, aminoalkyl, (alkyl)$_2$amino, alkanoyl, alkoxycarbonyl, alkyl sulfinyl, alkyl sulfonyl, aryl sulfonyl, carbocyclyl, benozyl, benzyl, aryl, or heterocyclyl, wherein $R^2$ is optionally substituted with one or more, the same or different, $R^{10}$; or $R^1$ and $R^2$ come together to form a heterocyclyl optionally substituted with one or more, the same or different, $R^{10}$; and $R^{10}$ is alkyl, halogen, nitro, cyano, hydroxy, amino, mercapto, formyl, carboxy, carbamoyl, alkoxy, hydroxyalkyl, alkylthio, thioalkyl, alkylamino, aminoalkyl, (alkyl)$_2$amino, alkanoyl, alkoxycarbonyl, alkylsulfinyl, alkyl sulfonyl, aryl sulfonyl, carbocyclyl, benozyl, benzyl, aryl, or heterocyclyl, wherein $R^{10}$ is optionally substituted with one or more, the same or different, $R^{11}$; and $R^{11}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, isopropoxy, tert-butoxy, hydoxymethyl, hydroxyethyl, thiomethyl, thioethyl, aminomethyl, aminoethyl, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, isopropoxycarbonyl, tert-butoxycarbonyl, N-methylsulfamoyl, N-ethylsulfamoyl, N,N-dimethylsulfamoyl, N,N-diethylsulfamoyl, N-methyl-N-ethylsulfamoyl, benozyl, benzyl, carbocyclyl, aryl, or heterocyclyl.

For any of the embodiments disclosed herein, both $R^1$ may be alkyl optionally substituted.

In certain embodiments, the compounds have the following formula:

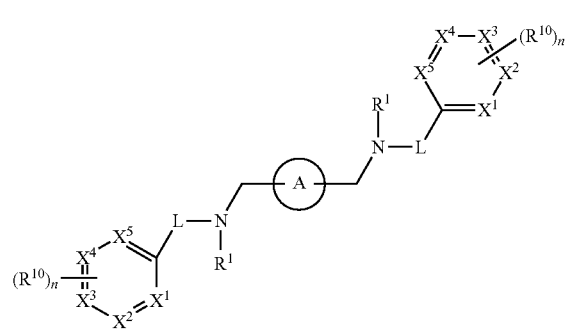

Formula IA salts, derivatives, and prodrugs thereof wherein,

A is an bridging aryl or heterocyclyl;

$X^1, X^2, X^3, X^4$, and $X^5$ are individually and independently selected from N or CH;

n is 0, 1, 2, 3, 4, or 5;

L is —CH$_2$— or a direct bond;

$R^1$ is hydrogen, alkyl, formyl, carboxy, hydroxyalkyl, thioalkyl, aminoalkyl, alkanoyl, alkoxycarbonyl, alkyl sulfinyl, alkyl sulfonyl, aryl sulfonyl, carbocyclyl, benozyl, benzyl, aryl, or heterocyclyl, wherein $R^1$ is optionally substituted with one or more, the same or different, $R^{10}$;

$R^{11}$ is alkyl, halogen, nitro, cyano, hydroxy, amino, mercapto, formyl, carboxy, carbamoyl, alkoxy, hydroxyalkyl, alkylthio, thioalkyl, alkylamino, aminoalkyl, (alkyl)$_2$amino, alkanoyl, alkoxycarbonyl, alkyl sulfinyl, alkyl sulfonyl, aryl sulfonyl, carbocyclyl, benozyl, benzyl, aryl, or heterocyclyl, wherein $R^{10}$ is optionally substituted with one or more, the same or different, $R^{11}$; and $R^{11}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, isopropoxy, tert-butoxy, hydoxymethyl, hydroxyethyl, thiomethyl, thioethyl, aminomethyl, aminoethyl, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, isopropoxycarbonyl, tert-butoxycarbonyl, N-methylsulfamoyl, N-ethylsulfamoyl, N,N-dimethylsulfamoyl, N,N-diethylsulfamoyl, N-methyl-N-ethylsulfamoyl, benozyl, benzyl, carbocyclyl, aryl, or heterocyclyl.

In certain embodiments, at least one of $X^1, X^2, X^3, X^4$, and $X^5$ is N. In certain embodiments, at least two of $X^1, X^2, X^3, X^4$, and $X^5$ are N.

In certain embodiments, the compounds have the following formula:

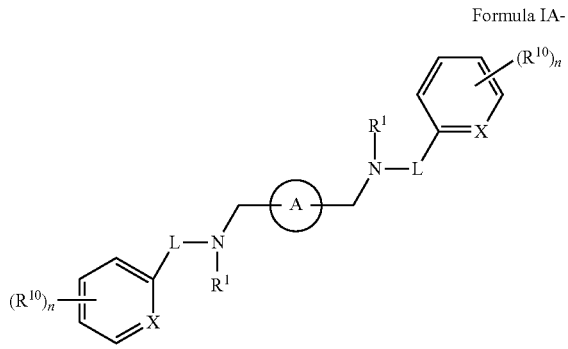

Formula IA-1 salts, derivatives, and prodrugs thereof wherein,
A is an bridging aryl or heterocyclyl;
n is 0, 1, 2, 3, 4, or 5; or n is 0 or 1; or n is 2;
X is N or CH;
L is —CH$_2$— or a direct bond;
R$^1$ is hydrogen, alkyl, formyl, carboxy, hydroxyalkyl, thioalkyl, aminoalkyl, alkanoyl, alkoxycarbonyl, alkyl sulfinyl, alkyl sulfonyl, aryl sulfonyl, carbocyclyl, benozyl, benzyl, aryl, or heterocylyl, wherein leis optionally substituted with one or more, the same or different, R$^{10}$;
R$^{10}$ is alkyl, halogen, nitro, cyano, hydroxy, amino, mercapto, formyl, carboxy, carbamoyl, alkoxy, hydroxyalkyl, alkylthio, thioalkyl, alkylamino, aminoalkyl, (alkyl)$_2$amino, alkanoyl, alkoxycarbonyl, alkyl sulfinyl, alkyl sulfonyl, aryl sulfonyl, carbocyclyl, benozyl, benzyl, aryl, or heterocyclyl, wherein R$^{10}$ is optionally substituted with one or more, the same or different, R$^{11}$; and
R$^{11}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, isopropoxy, tert-butoxy, hydoxymethyl, hydroxyethyl, thiomethyl, thioethyl, aminomethyl, aminoethyl, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, isopropoxycarbonyl, tert-butoxycarbonyl, N-methylsulfamoyl, N-ethylsulfamoyl, N,N-dimethylsulfamoyl, N,N-diethylsulfamoyl, N-methyl-N-ethylsulfamoyl, benozyl, benzyl, carbocyclyl, aryl, or heterocyclyl.

In certain embodiments, the compounds have the following formula:

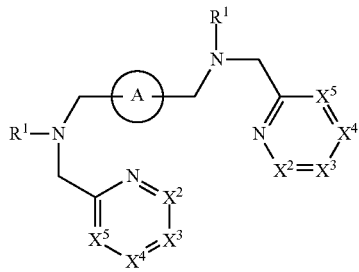

Formula IB salts, derivatives, and prodrugs thereof wherein,
A is an bridging aryl or heterocyclyl;
X$^2$ is N or CR$^6$; X$^3$ is N or CR$^5$; X$^4$ is N or CR$^3$; X$^5$ is N or CR$^2$;
R$^1$ is hydrogen, alkyl, formyl, carboxy, hydroxyalkyl, thioalkyl, aminoalkyl, alkanoyl, alkoxycarbonyl, alkyl sulfinyl, alkyl sulfonyl, aryl sulfonyl, carbocyclyl, benozyl, benzyl, aryl, or heterocyclyl, wherein R$^1$ is optionally substituted with one or more, the same or different, R$^{10}$;
R$^3$, R$^4$, R$^5$, and R$^6$, are each individually and independently selected from hydrogen, alkyl, halogen, nitro, cyano, hydroxy, amino, mercapto, formyl, carboxy, carbamoyl, alkoxy, hydroxyalkyl, alkylthio, thioalkyl, alkylamino, aminoalkyl, (alkyl)$_2$amino, alkanoyl, alkoxycarbonyl, alkyl sulfinyl, alkyl sulfonyl, aryl sulfonyl, carbocyclyl, benozyl, benzyl, aryl, or heterocyclyl, wherein R$^3$, R$^4$, R$^5$, and R$^6$, are optionally substituted with one or more, the same or different, R$^{10}$; and
R$^{10}$ is alkyl, halogen, nitro, cyano, hydroxy, amino, mercapto, formyl, carboxy, carbamoyl, alkoxy, hydroxyalkyl, alkylthio, thioalkyl, alkylamino, aminoalkyl, (alkyl)$_2$amino, alkanoyl, alkoxycarbonyl, alkyl sulfinyl, alkyl sulfonyl, aryl sulfonyl, carbocyclyl, benozyl, benzyl, aryl, or heterocyclyl, wherein R$^{10}$ is optionally substituted with one or more, the same or different, R$^{11}$; and
R$^{11}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, isopropoxy, tert-butoxy, hydoxymethyl, hydroxyethyl, thiomethyl, thioethyl, aminomethyl, aminoethyl, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, isopropoxycarbonyl, tert-butoxycarbonyl, N-methylsulfamoyl, N-ethylsulfamoyl, N,N-dimethylsulfamoyl, N,N-diethylsulfamoyl, N-methyl-N-ethylsulfamoyl, benozyl, benzyl, carbocyclyl, aryl, or heterocyclyl.

In certain embodiments, at least one X$^2$, X3, X$^4$, and X$^5$ is N.

In certain embodiments, the compounds have the following formula:

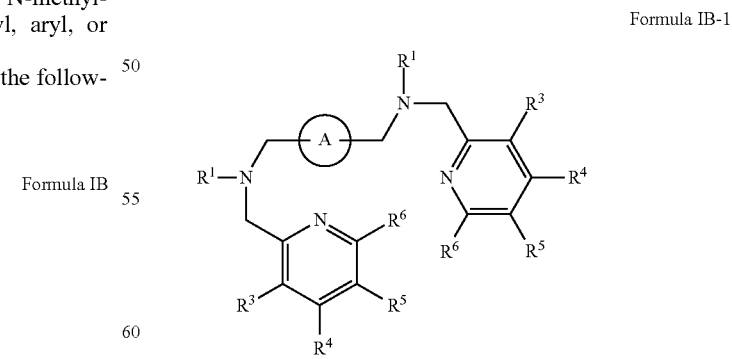

Formula IB-1 salts, derivatives, and prodrugs thereof wherein,
A is an bridging aryl or heterocyclyl;
R$^1$ is hydrogen, alkyl, formyl, carboxy, hydroxyalkyl, thioalkyl, aminoalkyl, alkanoyl, alkoxycarbonyl, alkyl sulfinyl, alkyl sulfonyl, aryl sulfonyl, carbocyclyl, benozyl, benzyl, aryl, or heterocyclyl, wherein $R^1$ is optionally substituted with one or more, the same or different, $R^{10}$;

$R^3$, $R^4$, $R^5$, and $R^6$, are each individually and independently selected from hydrogen, alkyl, halogen, nitro, cyano, hydroxy, amino, mercapto, formyl, carboxy, carbamoyl, alkoxy, hydroxyalkyl, alkylthio, thioalkyl, alkylamino, aminoalkyl, (alkyl)$_2$amino, alkanoyl, alkoxycarbonyl, alkyl sulfinyl, alkyl sulfonyl, aryl sulfonyl, carbocyclyl, benozyl, benzyl, aryl, or heterocyclyl, wherein $R^3$, $R^4$, $R^5$, and $R^6$, are optionally substituted with one or more, the same or different, $R^{10}$; and $R^{10}$ is alkyl, halogen, nitro, cyano, hydroxy, amino, mercapto, formyl, carboxy, carbamoyl, alkoxy, hydroxyalkyl, alkylthio, thioalkyl, alkylamino, aminoalkyl, (alkyl)$_2$amino, alkanoyl, alkoxycarbonyl, alkyl sulfinyl, alkyl sulfonyl, aryl sulfonyl, carbocyclyl, benozyl, benzyl, aryl, or heterocyclyl, wherein $R^{10}$ is optionally substituted with one or more, the same or different, $R^{11}$; and $R^{11}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, isopropoxy, tert-butoxy, hydoxymethyl, hydroxyethyl, thiomethyl, thioethyl, aminomethyl, aminoethyl, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, isopropoxycarbonyl, tert-butoxycarbonyl, N-methylsulfamoyl, N-ethylsulfamoyl, N,N-dimethylsulfamoyl, N,N-diethylsulfamoyl, N-methyl-N-ethylsulfamoyl, benozyl, benzyl, carbocyclyl, aryl, or heterocyclyl.

In certain embodiments, A is

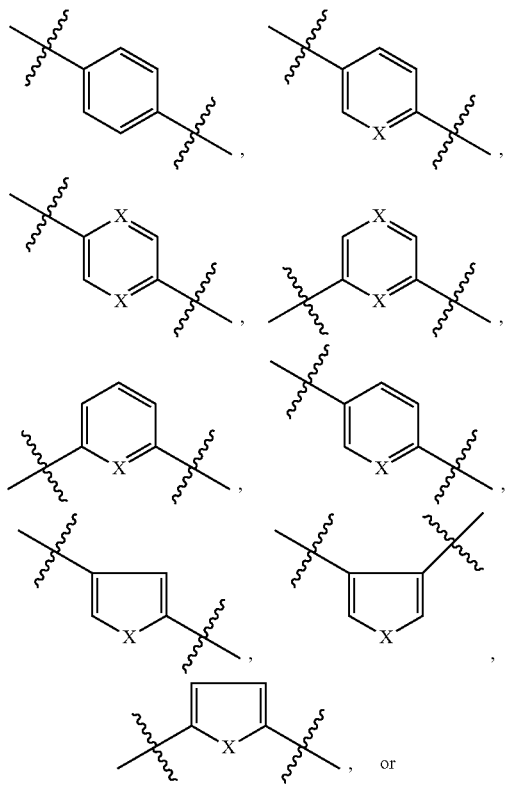

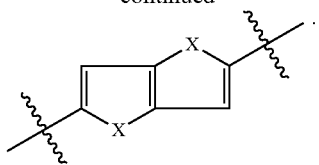

Wherein X is CH or N, or S or O, or X is N or CH, and/or at least one X is N, or both X are N; individually and independently at each occurrence.

In certain embodiments, the compounds have the following formula:

Formula IC

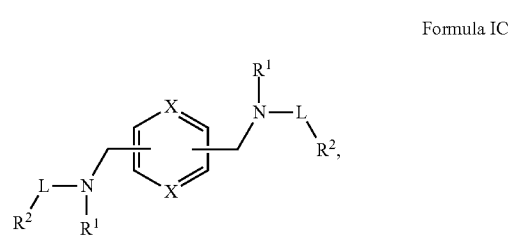

Formula ID

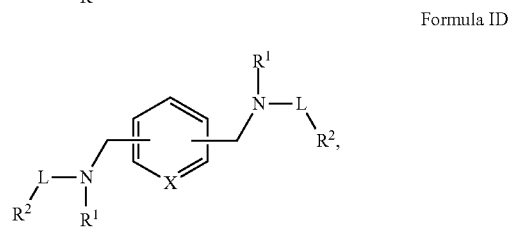

Formula IE

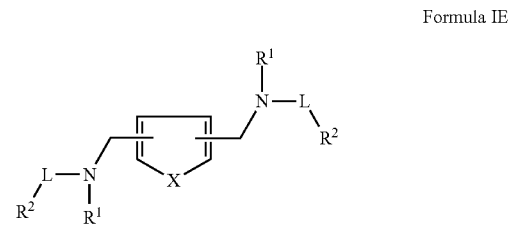

salts, derivatives, or prodrugs thereof wherein,

X is individually and independently at each occurrence N or CH, or O or S; or X is N or CH, and/or at least one X is N, or both X are N;

L is —CH$_2$— or a direct bond;

$R^1$ is hydrogen, alkyl, formyl, carboxy, hydroxyalkyl, thioalkyl, aminoalkyl, alkanoyl, alkoxycarbonyl, alkyl sulfinyl, alkyl sulfonyl, aryl sulfonyl, carbocyclyl, benozyl, benzyl, aryl, or heterocyclyl, wherein $R^1$ is optionally substituted with one or more, the same or different, $R^{10}$;

$R^2$ is aryl or heterocyclyl, wherein $R^2$ is optionally substituted with one or more, the same or different, $R^{10}$; or $R^1$ and $R^2$ come together to form a heterocyclyl optionally substituted with one or more, the same or different, $R^{10}$; and $R^{10}$ is alkyl, halogen, nitro, cyano, hydroxy, amino, mercapto, formyl, carboxy, carbamoyl, alkoxy, hydroxyalkyl, alkylthio, thioalkyl, alkylamino, aminoalkyl, (alkyl)$_2$amino, alkanoyl, alkoxycarbonyl, alkyl sulfinyl, alkyl sulfonyl, aryl sulfonyl, carbocyclyl, benozyl, benzyl, aryl, or heterocyclyl, wherein $R^{10}$ is optionally substituted with one or more, the same or different, $R^{11}$; and $R^{11}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, isopropoxy, tert-butoxy, hydoxymethyl, hydroxyethyl, thiomethyl, thioethyl, aminomethyl, aminoethyl, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, isopropoxycarbonyl, tert-butoxycarbonyl, N-methylsulfamoyl, N-ethylsulfamoyl, N,N-dimethylsulfamoyl, N,N-diethylsulfamoyl, N-methyl-N-ethylsulfamoyl, benozyl, benzyl, carbocyclyl, aryl, or heterocyclyl.

In certain embodiments, the compounds have the following formula:

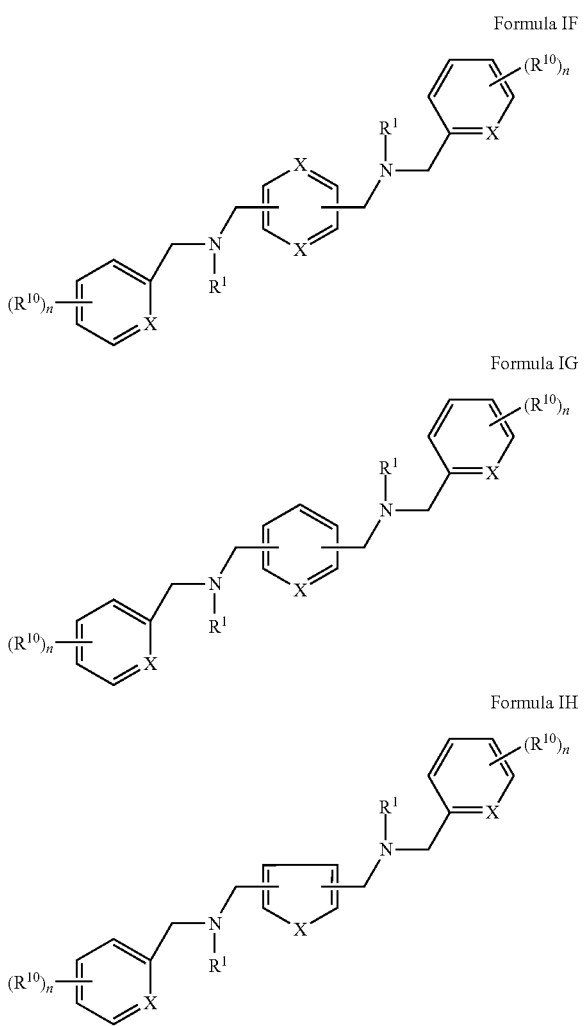

Formula IF

Formula IG

Formula IH salts, derivatives, or prodrugs thereof wherein,

X is individually and independently at each occurrence N or CH, or O or S; or X is N or CH, and/or at least one X is N, or both X are N;

L is —CH$_2$— or a direct bond;

n is 0, 1, 2, 3, 4, or 5; or n is 0 or 1; or n is 2;

R$^1$ is hydrogen, alkyl, formyl, carboxy, hydroxyalkyl, thioalkyl, aminoalkyl, alkanoyl, alkoxycarbonyl, alkyl sulfinyl, alkyl sulfonyl, aryl sulfonyl, carbocyclyl, benozyl, benzyl, aryl, or heterocyclyl, wherein R$^1$ is optionally substituted with one or more, the same or different, R$^{10}$;

R$^{10}$ is alkyl, halogen, nitro, cyano, hydroxy, amino, mercapto, formyl, carboxy, carbamoyl, alkoxy, hydroxyalkyl, alkylthio, thioalkyl, alkylamino, aminoalkyl, (alkyl)$_2$amino, alkanoyl, alkoxycarbonyl, alkyl sulfinyl, alkyl sulfonyl, aryl sulfonyl, carbocyclyl, benozyl, benzyl, aryl, or heterocyclyl, wherein R$^{10}$ is optionally substituted with one or more, the same or different, R$^{11}$; and R$^{11}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, isopropoxy, tert-butoxy, hydoxymethyl, hydroxyethyl, thiomethyl, thioethyl, aminomethyl, aminoethyl, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, isopropoxycarbonyl, tert-butoxycarbonyl, N-methylsulfamoyl, N-ethylsulfamoyl, N,N-dimethylsulfamoyl, N,N-diethylsulfamoyl, N-methyl-N-ethylsulfamoyl, benozyl, benzyl, carbocyclyl, aryl, or heterocyclyl.

In certain embodiments, the compounds have the following formula:

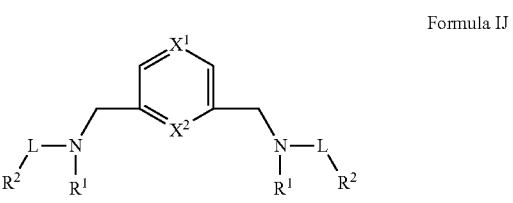

Formula IJ salts, derivatives, and prodrugs thereof wherein,

X$^1$ is CH or N;

X$^2$ is N;

L is —CH$_2$— or a direct bond;

R$^1$ is hydrogen or alkyl optionally substituted with one or more, the same or different, R$^{10}$;

R$^2$ is aryl, or heterocyclyl, wherein R$^2$ is optionally substituted with one or more, the same or different, R$^{10}$; and R$^{10}$ is alkyl, halogen, nitro, cyano, hydroxy, amino, mercapto, formyl, carboxy, carbamoyl, alkoxy, hydroxyalkyl, alkylthio, thioalkyl, alkylamino, aminoalkyl, (alkyl)$_2$amino, alkanoyl, alkoxycarbonyl, alkyl sulfinyl, alkyl sulfonyl, aryl sulfonyl, carbocyclyl, benozyl, benzyl, aryl, or heterocyclyl, wherein R$^{10}$ is optionally substituted with one or more, the same or different, R$^{11}$; and R$^{11}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, isopropoxy, tert-butoxy, hydoxymethyl, hydroxyethyl, thiomethyl, thioethyl, aminomethyl, aminoethyl, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, isopropoxycarbonyl, tert-butoxycarbonyl, N-methylsulfamoyl, N-ethylsulfamoyl, N,N-dimethylsulfamoyl, N,N-diethylsulfamoyl, N-methyl-N-ethylsulfamoyl, benozyl, benzyl, carbocyclyl, aryl, or heterocyclyl.

In certain embodiments, the compounds have the following formula:

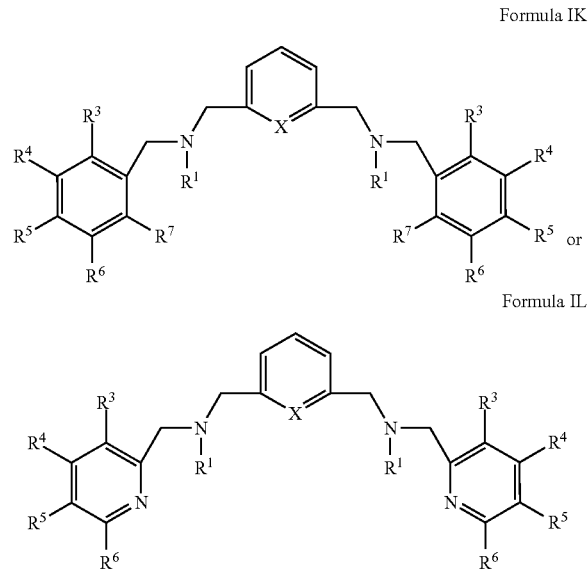

Formula IK

Formula IL salts, derivatives, and prodrugs thereof wherein,

X is N or CH;

$R^1$ is hydrogen or alkyl optionally substituted with one or more, the same or different, $R^{10}$;

$R^3$, $R^4$, $R^5$, $R^6$, and $R^7$, are each individually and independently selected from hydrogen, alkyl, halogen, nitro, cyano, hydroxy, amino, mercapto, formyl, carboxy, carbamoyl, alkoxy, hydroxyalkyl, alkylthio, thioalkyl, alkylamino, aminoalkyl, (alkyl)$_2$amino, alkanoyl, alkoxycarbonyl, alkyl sulfinyl, alkyl sulfonyl, aryl sulfonyl, carbocyclyl, benozyl, benzyl, aryl, or heterocyclyl, wherein $R^3$, $R^4$, $R^5$, $R^6$, and $R^7$ are optionally substituted with one or more, the same or different, $R^{10}$; and $R^{10}$ is alkyl, halogen, nitro, cyano, hydroxy, amino, mercapto, formyl, carboxy, carbamoyl, alkoxy, hydroxyalkyl, alkylthio, thioalkyl, alkylamino, aminoalkyl, (alkyl)$_2$amino, alkanoyl, alkoxycarbonyl, alkyl sulfinyl, alkyl sulfonyl, aryl sulfonyl, carbocyclyl, benozyl, benzyl, aryl, or heterocyclyl, wherein $R^{10}$ is optionally substituted with one or more, the same or different, $R^{11}$; and $R^{11}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, isopropoxy, tert-butoxy, hydoxymethyl, hydroxyethyl, thiomethyl, thioethyl, aminomethyl, aminoethyl, acetyl, acetoxy, methylamino, ethylamino, dimethylamino, diethylamino, N-methyl-N-ethylamino, acetylamino, N-methylcarbamoyl, N-ethylcarbamoyl, N,N-dim ethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, isopropoxycarbonyl, tert-butoxycarbonyl, N-methylsulfamoyl, N-ethylsulfamoyl, N,N-dimethylsulfamoyl, N,N-diethylsulfamoyl, N-methyl-N-ethylsulfamoyl, benozyl, benzyl, carbocyclyl, aryl, or heterocyclyl.

In certain embodiments, the compounds have the following formula:

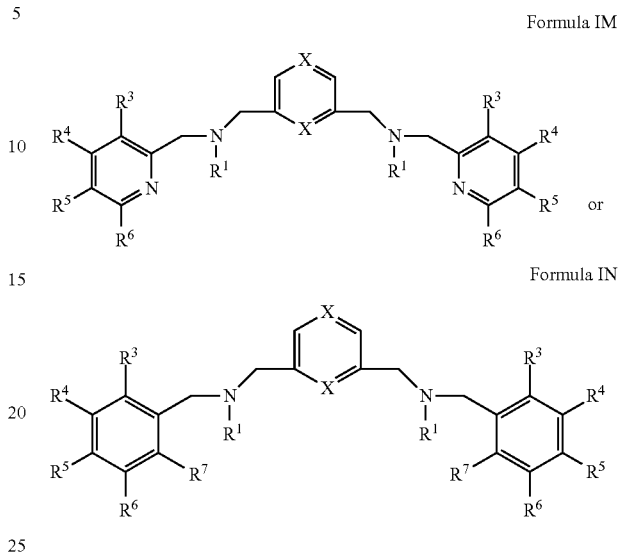

Formula IM

Formula IN salts, derivatives, and prodrugs thereof wherein,

X is N or CH; or X is N or CH, and/or at least one X is N, or both X are N;

$R^1$ is hydrogen or alkyl optionally substituted with one or more, the same or different, $R^{10}$;

$R^3$, $R^4$, $R^5$, $R^6$, and $R^7$, are each individually and independently selected from hydrogen, alkyl, halogen, nitro, cyano, hydroxy, amino, mercapto, formyl, carboxy, carbamoyl, alkoxy, hydroxyalkyl, alkylthio, thioalkyl, alkylamino, aminoalkyl, (alkyl)$_2$amino, alkanoyl, alkoxycarbonyl, alkyl sulfinyl, alkyl sulfonyl, aryl sulfonyl, carbocyclyl, benozyl, benzyl, aryl, or heterocyclyl, wherein $R^3$, $R^4$, $R^5$, $R^6$, and $R^7$ are optionally substituted with one or more, the same or different, $R^{10}$; and $R^{10}$ is alkyl, halogen, nitro, cyano, hydroxy, amino, mercapto, formyl, carboxy, carbamoyl, alkoxy, hydroxyalkyl, alkylthio, thioalkyl, alkylamino, aminoalkyl, (alkyl)$_2$amino, alkanoyl, alkoxycarbonyl, alkyl sulfinyl, alkyl sulfonyl, aryl sulfonyl, carbocyclyl, benozyl, benzyl, aryl, or heterocyclyl, wherein $R^{10}$ is optionally substituted with one or more, the same or different, $R^{11}$; and $R^{11}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, isopropoxy, tert-butoxy, hydoxymethyl, hydroxyethyl, thiomethyl, thioethyl, aminomethyl, aminoethyl, acetyl, acetoxy, methylamino, ethylamino, dimethylamino, diethylamino, N-methyl-N-ethylamino, acetylamino, N-methylcarbamoyl, N-ethylcarbamoyl, N,N-dim ethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, isopropoxycarbonyl, tert-butoxycarbonyl, N-methylsulfamoyl, N-ethylsulfamoyl, N,N-dimethylsulfamoyl, N,N-diethylsulfamoyl, N-methyl-N-ethylsulfamoyl, benozyl, benzyl, carbocyclyl, aryl, or heterocyclyl.

In certain embodiments, the compounds have the following formula:

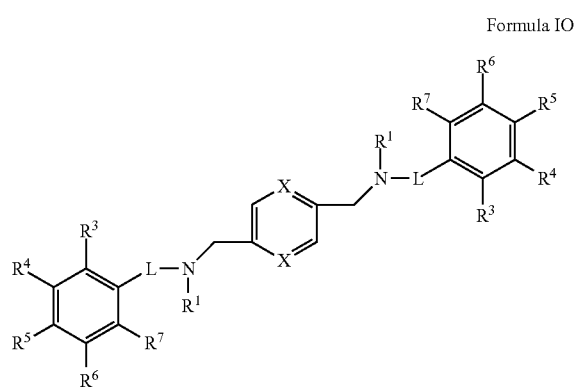

Formula IO salts, derivatives, and prodrugs thereof wherein,

X is N or CH, and/or at least one X is N, or both X are N;

L is —$CH_2$— or a direct bond;

$R^1$ is hydrogen or alkyl optionally substituted with one or more, the same or different, $R^{10}$;

$R^3$, $R^4$, $R^5$, $R^6$, and $R^7$, are each individually and independently selected from hydrogen, alkyl, halogen, nitro, cyano, hydroxy, amino, mercapto, formyl, carboxy, carbamoyl, alkoxy, hydroxyalkyl, alkylthio, thioalkyl, alkylamino, aminoalkyl, (alkyl)$_2$amino, alkanoyl, alkoxycarbonyl, alkylsulfinyl, alkylsulfonyl, arylsulfonyl, carbocyclyl, benozyl, benzyl, aryl, or heterocyclyl, wherein $R^3$, $R^4$, $R^5$, $R^6$, and $R^7$ are optionally substituted with one or more, the same or different, $R^{10}$; and $R^{10}$ is alkyl, halogen, nitro, cyano, hydroxy, amino, mercapto, formyl, carboxy, carbamoyl, alkoxy, hydroxyalkyl, alkylthio, thioalkyl, alkylamino, aminoalkyl, (alkyl)$_2$amino, alkanoyl, alkoxycarbonyl, alkylsulfinyl, alkylsulfonyl, arylsulfonyl, carbocyclyl, benozyl, benzyl, aryl, or heterocyclyl, wherein $R^{10}$ is optionally substituted with one or more, the same or different, $R^{11}$; and $R^{11}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, isopropoxy, tert-butoxy, hydoxymethyl, hydroxyethyl, thiomethyl, thioethyl, aminomethyl, aminoethyl, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, isopropoxycarbonyl, tert-butoxycarbonyl, N-methylsulfamoyl, N-ethylsulfamoyl, N,N-dim ethylsulfamoyl, N,N-diethylsulfamoyl, N-methyl-N-ethylsulfamoyl, benozyl, benzyl, carbocyclyl, aryl, or heterocyclyl.

In certain embodiments, the compounds have the following formula:

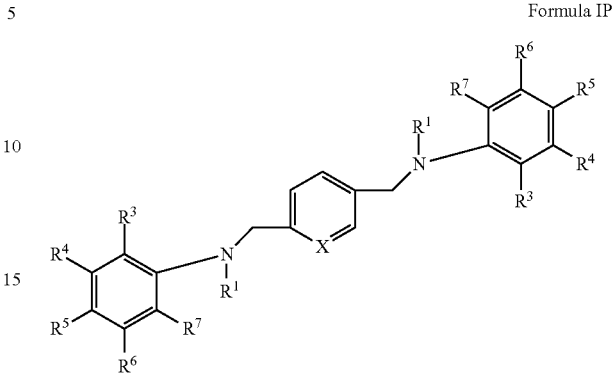

Formula IP salts, derivatives, and prodrugs thereof wherein,

X is N or CH;

L is —$CH_2$— or a direct bond;

$R^1$ is hydrogen or alkyl optionally substituted with one or more, the same or different, $R^{10}$;

$R^3$, $R^4$, $R^5$, $R^6$, and $R^7$, are each individually and independently selected from hydrogen, alkyl, halogen, nitro, cyano, hydroxy, amino, mercapto, formyl, carboxy, carbamoyl, alkoxy, hydroxyalkyl, alkylthio, thioalkyl, alkylamino, aminoalkyl, (alkyl)$_2$amino, alkanoyl, alkoxycarbonyl, alkyl sulfinyl, alkyl sulfonyl, aryl sulfonyl, carbocyclyl, benozyl, benzyl, aryl, or heterocyclyl, wherein $R^3$, $R^4$, $R^5$, $R^6$, and $R^7$ are optionally substituted with one or more, the same or different, $R^{10}$; and $R^{10}$ is alkyl, halogen, nitro, cyano, hydroxy, amino, mercapto, formyl, carboxy, carbamoyl, alkoxy, hydroxyalkyl, alkylthio, thioalkyl, alkylamino, aminoalkyl, (alkyl)$_2$amino, alkanoyl, alkoxycarbonyl, alkyl sulfinyl, alkyl sulfonyl, aryl sulfonyl, carbocyclyl, benozyl, benzyl, aryl, or heterocyclyl, wherein $R^{10}$ is optionally substituted with one or more, the same or different, $R^{11}$; and $R^{11}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, isopropoxy, tert-butoxy, hydoxymethyl, hydroxyethyl, thiomethyl, thioethyl, aminomethyl, aminoethyl, acetyl, acetoxy, methylamino, ethylamino, dimethylamino, diethylamino, N-methyl-N-ethylamino, acetylamino, N-methylcarbamoyl, N-ethylcarbamoyl, N,N-dim ethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, isopropoxycarbonyl, tert-butoxycarbonyl, N-methylsulfamoyl, N-ethylsulfamoyl, N,N-dimethylsulfamoyl, N,N-diethylsulfamoyl, N-methyl-N-ethylsulfamoyl, benozyl, benzyl, carbocyclyl, aryl, or heterocyclyl.

In certain embodiments, the compound has the following formula:

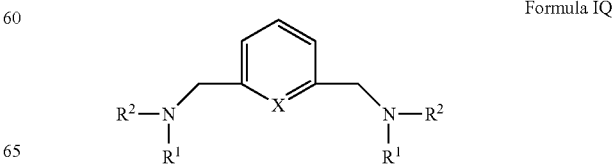

Formula IQ salts, derivatives, and prodrugs thereof wherein,

R¹ and R² come together to form a heterocyclyl optionally substituted with one or more, the same or different, R¹⁰, and R¹⁰ is alkyl, halogen, nitro, cyano, hydroxy, amino, mercapto, formyl, carboxy, carbamoyl, alkoxy, hydroxyalkyl, alkylthio, thioalkyl, alkylamino, aminoalkyl, (alkyl)₂amino, alkanoyl, alkoxycarbonyl, alkyl sulfinyl, alkyl sulfonyl, aryl sulfonyl, carbocyclyl, benozyl, benzyl, aryl, or heterocyclyl, wherein R¹⁰ is optionally substituted with one or more, the same or different, R¹¹; and R¹¹ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, isopropoxy, tert-butoxy, hydoxymethyl, hydroxyethyl, thiomethyl, thioethyl, aminomethyl, aminoethyl, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, isopropoxycarbonyl, tert-butoxycarbonyl, N-methylsulfamoyl, N-ethylsulfamoyl, N,N-dimethylsulfamoyl, N,N-diethylsulfamoyl, N-methyl-N-ethylsulfamoyl, benozyl, benzyl, carbocyclyl, aryl, or heterocyclyl.

In certain embodiments, the compounds have the following formula:

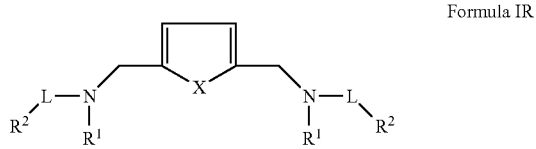

Formula IR salts, derivatives, and prodrugs thereof wherein,

X is O or S or NH;

L is —CH₂— or a direct bond;

R¹ is hydrogen or alkyl optionally substituted with one or more, the same or different, R¹⁰;

R² is aryl or heterocyclyl, wherein R² is optionally substituted with one or more, the same or different, R¹⁰; and R¹⁰ is alkyl, halogen, nitro, cyano, hydroxy, amino, mercapto, formyl, carboxy, carbamoyl, alkoxy, hydroxyalkyl, alkylthio, thioalkyl, alkylamino, aminoalkyl, (alkyl)₂amino, alkanoyl, alkoxycarbonyl, alkylsulfinyl, alkyl sulfonyl, aryl sulfonyl, carbocyclyl, benozyl, benzyl, aryl, or heterocyclyl, wherein R¹⁰ is optionally substituted with one or more, the same or different, R¹¹; and R¹¹ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, isopropoxy, tert-butoxy, hydoxymethyl, hydroxyethyl, thiomethyl, thioethyl, aminomethyl, aminoethyl, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, isopropoxycarbonyl, tert-butoxycarbonyl, N-methylsulfamoyl, N-ethylsulfamoyl, N,N-dimethylsulfamoyl, N,N-diethylsulfamoyl, N-methyl-N-ethylsulfamoyl, benozyl, benzyl, carbocyclyl, aryl, or heterocyclyl.

In certain embodiments, the compounds have the following formula:

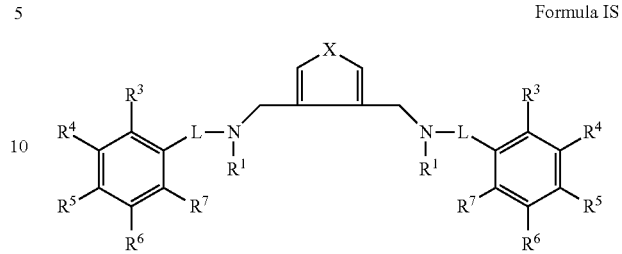

Formula IS salts, derivatives, and prodrugs thereof wherein,

X is O or S or NH;

L is —CH₂— or a direct bond;

R¹ is hydrogen or alkyl optionally substituted with one or more, the same or different, R¹⁰;

R³, R⁴, R⁵, R⁶, and R⁷, are each individually and independently selected from hydrogen, alkyl, halogen, nitro, cyano, hydroxy, amino, mercapto, formyl, carboxy, carbamoyl, alkoxy, hydroxyalkyl, alkylthio, thioalkyl, alkylamino, aminoalkyl, (alkyl)₂amino, alkanoyl, alkoxycarbonyl, alkyl sulfinyl, alkyl sulfonyl, aryl sulfonyl, carbocyclyl, benozyl, benzyl, aryl, or heterocyclyl, wherein R³, R⁴, R⁵, R⁶, and R⁷ are optionally substituted with one or more, the same or different, R¹⁰; and R¹⁰ is alkyl, halogen, nitro, cyano, hydroxy, amino, mercapto, formyl, carboxy, carbamoyl, alkoxy, hydroxyalkyl, alkylthio, thioalkyl, alkylamino, aminoalkyl, (alkyl)₂amino, alkanoyl, alkoxycarbonyl, alkyl sulfinyl, alkyl sulfonyl, aryl sulfonyl, carbocyclyl, benozyl, benzyl, aryl, or heterocyclyl, wherein R¹⁰ is optionally substituted with one or more, the same or different, R¹¹; and R¹¹ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, isopropoxy, tert-butoxy, hydoxymethyl, hydroxyethyl, thiomethyl, thioethyl, aminomethyl, aminoethyl, acetyl, acetoxy, methyl amino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, isopropoxycarbonyl, tert-butoxycarbonyl, N-methylsulfamoyl, N-ethylsulfamoyl, N,N-dimethylsulfamoyl, N,N-diethylsulfamoyl, N-methyl-N-ethylsulfamoyl, benozyl, benzyl, carbocyclyl, aryl, or heterocyclyl.

In certain embodiments, the compounds have the following formula:

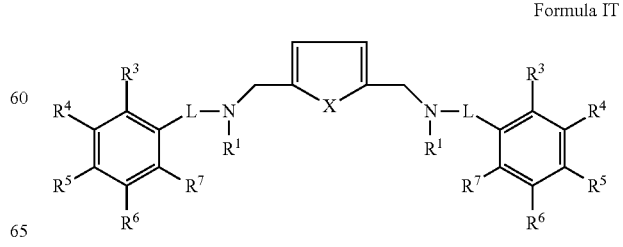

Formula IT salts, derivatives, and prodrugs thereof wherein,
X is O or S or NH;
L is —CH$_2$— or a direct bond;
R$^1$ is hydrogen or alkyl optionally substituted with one or more, the same or different, R$^{10}$;

R$^3$, R$^4$, R$^5$, R$^6$, and R$^7$, are each individually and independently selected from hydrogen, alkyl, halogen, nitro, cyano, hydroxy, amino, mercapto, formyl, carboxy, carbamoyl, alkoxy, hydroxyalkyl, alkylthio, thioalkyl, alkylamino, aminoalkyl, (alkyl)$_2$amino, alkanoyl, alkoxycarbonyl, alkyl sulfinyl, alkyl sulfonyl, aryl sulfonyl, carbocyclyl, benozyl, benzyl, aryl, or heterocyclyl, wherein R$^3$, R$^4$, R$^5$, R$^6$, and R$^7$ are optionally substituted with one or more, the same or different, R$^{10}$; and R$^{10}$ is alkyl, halogen, nitro, cyano, hydroxy, amino, mercapto, formyl, carboxy, carbamoyl, alkoxy, hydroxyalkyl, alkylthio, thioalkyl, alkylamino, aminoalkyl, (alkyl)$_2$amino, alkanoyl, alkoxycarbonyl, alkyl sulfinyl, alkyl sulfonyl, aryl sulfonyl, carbocyclyl, benozyl, benzyl, aryl, or heterocyclyl, wherein R$^{10}$ is optionally substituted with one or more, the same or different, R$^{11}$; and R$^{11}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, isopropoxy, tert-butoxy, hydoxymethyl, hydroxyethyl, thiomethyl, thioethyl, aminomethyl, aminoethyl, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, isopropoxycarbonyl, tert-butoxycarbonyl, N-methylsulfamoyl, N-ethylsulfamoyl, N,N-dimethylsulfamoyl, N,N-diethylsulfamoyl, N-methyl-N-ethylsulfamoyl, benozyl, benzyl, carbocyclyl, aryl, or heterocyclyl.

In certain embodiments, the compound having the following formula:

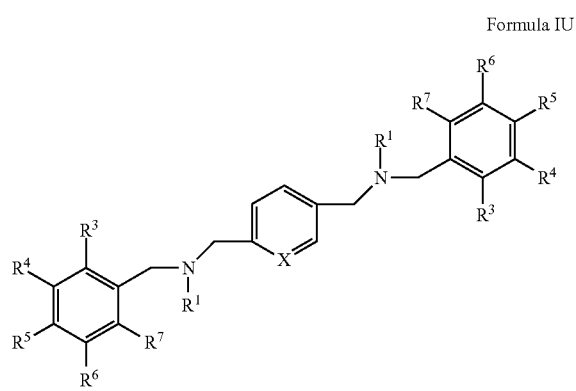

Formula IU salts, derivatives, and prodrugs thereof wherein,
X is N or CH;
R$^1$ is hydrogen or alkyl optionally substituted with one or more, the same or different, R$^{10}$;

R$^3$, R$^4$, R$^5$, R$^6$, and R$^7$, are each individually and independently selected from hydrogen, alkyl, halogen, nitro, cyano, hydroxy, amino, mercapto, formyl, carboxy, carbamoyl, alkoxy, hydroxyalkyl, alkylthio, thioalkyl, alkylamino, aminoalkyl, (alkyl)$_2$amino, alkanoyl, alkoxycarbonyl, alkylsulfinyl, alkylsulfonyl, arylsulfonyl, carbocyclyl, benozyl, benzyl, aryl, or heterocyclyl, wherein R$^3$, R$^4$, R$^5$, R$^6$, and R$^7$ are optionally substituted with one or more, the same or different, R$^{10}$; and R$^{10}$ is alkyl, halogen, nitro, cyano, hydroxy, amino, mercapto, formyl, carboxy, carbamoyl, alkoxy, hydroxyalkyl, alkylthio, thioalkyl, alkylamino, aminoalkyl, (alkyl)$_2$amino, alkanoyl, alkoxycarbonyl, alkylsulfinyl, alkylsulfonyl, arylsulfonyl, carbocyclyl, benozyl, benzyl, aryl, or heterocyclyl, wherein R$^{10}$ is optionally substituted with one or more, the same or different, R$^{11}$; and R$^{11}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, isopropoxy, tert-butoxy, hydoxymethyl, hydroxyethyl, thiomethyl, thioethyl, aminomethyl, aminoethyl, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, isopropoxycarbonyl, tert-butoxycarbonyl, N-methylsulfamoyl, N-ethylsulfamoyl, N,N-dimethylsulfamoyl, N,N-diethylsulfamoyl, N-methyl-N-ethylsulfamoyl, benozyl, benzyl, carbocyclyl, aryl, or heterocyclyl.

In certain embodiment, the disclosure contemplates compounds of the following formula:

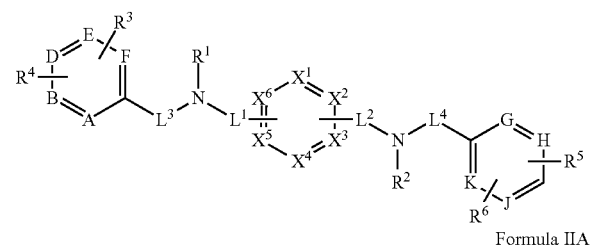

Formula II

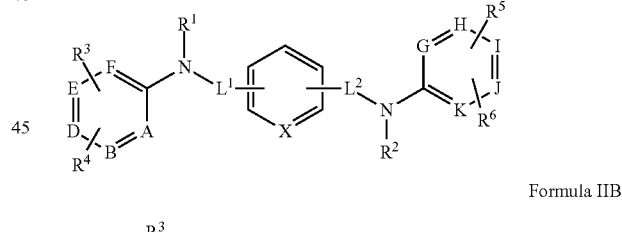

Formula IIA

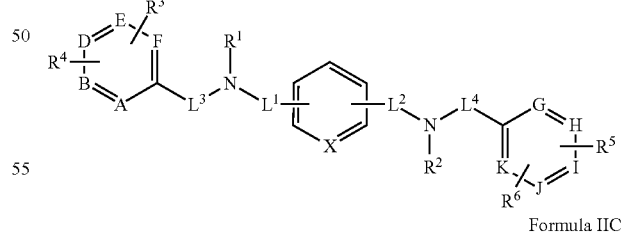

Formula IIB

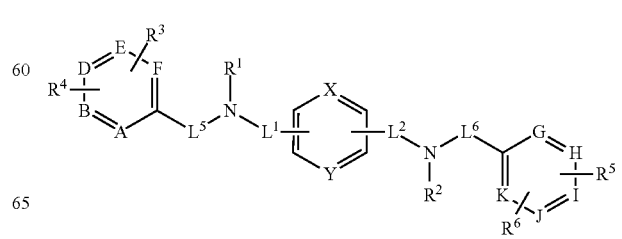

Formula IIC

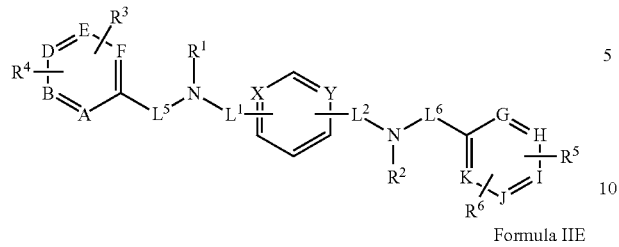

Wherein any of the above formula are defined by
X1, X2, X3, X4, X5, X6, Y1, Y2, Y3, Y4 are each independently N, —CH—, or CR1, at least one of X1, X2, X3, X4, X5, X6 is N;
X and Y are each independently N or CR1;
Z is NH, NR1, O or S;
A, B, D, E, F, G, H, I, J, K are independently N or CH, they can be all CH or N, or at least one of A, B, D, E, F, G, H, I, J, K is N;
L1 and L2 are each independently —CH$_2$— or covalent bond;
L3 and L4 are each independently —CH$_2$—;
L5 and L6 are each independently —CH$_2$—, or covalent bond;
L7 and L8 are each independently —CH$_2$—, —CH$_2$CH$_2$—, —CH$_2$CH$_2$CH$_2$— or covalent bond;
R1 and R2 are each independently substituted or unsubstituted alkyl, substituted or unsubstituted alkenyl, substituted or unsubstituted alkynyl, alkoxy, alkoxyalkyl, alkoxyacyl, haloalkyl, cyanoalkyl, hydroxyalkyl, thioalkyl, alkylthioalkyl, substituted or unsubstituted aminoalkyl, substituted or unsubstituted aminoacylalkyl, substituted or unsubstituted amino, substituted or unsubstituted arylamino, substituted or unsubstituted heteroarylamino, substituted or unsubstituted arylacyl, substituted or unsubstituted heteroarylacyl, substituted or unsubstituted aminoacyl, substituted or unsubstituted arylalkyl, substituted or unsubstituted heteroarylalkyl, substituted or unsubstituted heterocyclylalkyl, substituted or unsubstituted aryl, substituted or unsubstituted heteroaryl, substituted or unsubstituted cycloalkyl, substituted or unsubstituted cycloalkylalkyl, substituted or unsubstituted heterocyclyl;

R3, R4, R5 and R6 are independently hydrogen, halogen, —ORx, —N(RxRy), —SRx, N-alkylaminoalkyl, N,N-dialkylaminoalkyl, alkylthioalkyl, —S(O)—RX, —S(O)2-Rx, —S(O)2-N(RxRy), N-acylamino, —C(O)—Rx, —C(O)2-Rx, and —C(O)2-N(RxRy); wherein Rx and Ry are independently hydrogen, substituted or unsubstituted alkyl, substituted or unsubstituted arylalkyl, substituted or unsubstituted heteroarylalkyl, substituted or unsubstituted aryl, or substituted or unsubstituted heteroaryl;

R3, R4, R5 and R6 are each independently substituted or unsubstituted alkyl, substituted or unsubstituted alkenyl, substituted or unsubstituted alkynyl, alkoxy, alkoxyalkyl, alkoxyacyl, haloalkyl, cyanoalkyl, hydroxyalkyl, thioalkyl, alkylthioalkyl, substituted or unsubstituted aminoalkyl, substituted or unsubstituted aminoacylalkyl, substituted or unsubstituted amino, substituted or unsubstituted arylamino, substituted or unsubstituted heteroarylamino, substituted or unsubstituted arylacyl, substituted or unsubstituted heteroarylacyl, substituted or unsubstituted aminoacyl, substituted or unsubstituted arylalkyl, substituted or unsubstituted heteroarylalkyl, substituted or unsubstituted heterocyclylalkyl, substituted or unsubstituted aryl, substituted or unsubstituted heteroaryl, substituted or unsubstituted cycloalkyl, substituted or unsubstituted cycloalkylalkyl, substituted or unsubstituted heterocyclyl.

R7 and R8 are each independently

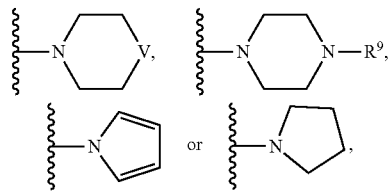

Or at least one is;

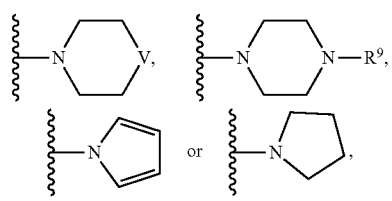

The other one is

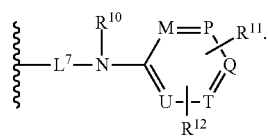

L7 is —CH2- or covalent bond;
V=O, NH or CH2;
M, P, Q, T, U are independently N or CH, they can be all CH or N, or at least one of M, P, Q, T, U is N;
R9 is hydrogen, halogen, —ORx, —N(RxRy), —SRx, N-alkylaminoalkyl, N,N-dialkylaminoalkyl, alkylthioalkyl, —S(O)—RX, —S(O)2-Rx, —S(O)2-N(RxRy), N-acylamino, —C(O)—Rx, —C(O)2-Rx, and —C(O)2-N(RxRy); wherein Rx and Ry are independently hydrogen, substituted or unsubstituted alkyl, substituted or unsubstituted arylalkyl, substituted or unsubstituted heteroarylalkyl, substituted or unsubstituted aryl, or substituted or unsubstituted heteroaryl;

R9 is substituted or unsubstituted alkyl, substituted or unsubstituted alkenyl, substituted or unsubstituted alkynyl, alkoxy, alkoxyalkyl, alkoxyacyl, haloalkyl, cyanoalkyl, hydroxyalkyl, thioalkyl, alkylthioalkyl, substituted or unsubstituted aminoalkyl, substituted or unsubstituted aminoacylalkyl, substituted or unsubstituted amino, substituted or unsubstituted arylamino, substituted or unsubstituted heteroarylamino, substituted or unsubstituted arylacyl, substituted or unsubstituted heteroarylacyl, substituted or unsubstituted aminoacyl, substituted or unsubstituted arylalkyl, substituted or unsubstituted heteroarylalkyl, substituted or unsubstituted heterocyclylalkyl, substituted or unsubstituted aryl, substituted or unsubstituted heteroaryl, substituted or unsubstituted cycloalkyl, substituted or unsubstituted cycloalkylalkyl, substituted or unsubstituted heterocyclyl;

R10 is substituted or unsubstituted alkyl, substituted or unsubstituted alkenyl, substituted or unsubstituted alkynyl, alkoxy, alkoxyalkyl, alkoxyacyl, haloalkyl, cyanoalkyl, hydroxyalkyl, thioalkyl, alkylthioalkyl, substituted or unsubstituted aminoalkyl, substituted or unsubstituted aminoacylalkyl, substituted or unsubstituted amino, substituted or unsubstituted arylamino, substituted or unsubstituted heteroarylamino, substituted or unsubstituted arylacyl, substituted or unsubstituted heteroarylacyl, substituted or unsubstituted aminoacyl, substituted or unsubstituted arylalkyl, substituted or unsubstituted heteroarylalkyl, substituted or unsubstituted heterocyclylalkyl, substituted or unsubstituted aryl, substituted or unsubstituted heteroaryl, substituted or unsubstituted cycloalkyl, substituted or unsubstituted cycloalkylalkyl, substituted or unsubstituted heterocyclyl;

R11 and R12 are each independently hydrogen, halogen, substituted or unsubstituted alkyl, substituted or unsubstituted alkenyl, substituted or unsubstituted alkynyl, alkoxy, alkoxyalkyl, alkoxyacyl, haloalkyl, cyanoalkyl, hydroxyalkyl, thioalkyl, alkylthioalkyl, substituted or unsubstituted aminoalkyl, substituted or unsubstituted aminoacylalkyl, substituted or unsubstituted amino, substituted or unsubstituted arylamino, substituted or unsubstituted heteroarylamino, substituted or unsubstituted arylacyl, substituted or unsubstituted heteroarylacyl, substituted or unsubstituted aminoacyl, substituted or unsubstituted arylalkyl, substituted or unsubstituted heteroarylalkyl, substituted or unsubstituted heterocyclylalkyl, substituted or unsubstituted aryl, substituted or unsubstituted heteroaryl, substituted or unsubstituted cycloalkyl, substituted or unsubstituted cycloalkylalkyl, substituted or unsubstituted heterocyclyl.

In certain embodiments, the formula exclude or do not cover the following compounds:
2,6-Bis(anilinomethyl)pyridine
2,6-Bis(3-fluoroanilinomethyl)pyridine
2,6-Bis(4-fluoroanilinomethyl)pyridine
2,6-Bis(3-chloroanilinomethyl)pyridine
2,6-Bis(4-chloroanilinomethyl)pyridine
2,6-Bis[(3-trifluoromethyl)anilinomethyl)]pyridine
2,6-Bis(3-nitroanilinomethyl)pyridine
2,6-Bis(4-nitroanilinomethyl)pyridine
2,6-Bis(4-ethylanilinomethyl)pyridine
2,6-Bis(4-methoxyanilinomethyl)pyridine
2,6-Bis(2-methoxyanilinomethyl)pyridine
2,6-Bis(pyridyl-2-aminomethyl)pyridine.

Methods of Use

The compounds can be used to treat disorders of abnormal cell proliferation generally, examples of which include, but are not limited to, types of cancers and proliferative disorders listed below. Abnormal cellular proliferation, notably hyperproliferation, can occur as a result of a wide variety of factors, including genetic mutation, infection, exposure to toxins, autoimmune disorders, and benign or malignant tumor induction.

There are a number of skin disorders associated with cellular hyperproliferation. Psoriasis, for example, is a benign disease of human skin generally characterized by plaques covered by thickened scales. The disease is caused by increased proliferation of epidermal cells of unknown cause. In normal skin the time required for a cell to move from the basal layer to the upper granular layer is about five weeks. In psoriasis, this time is only 6 to 9 days, partially due to an increase in the number of proliferating cells and an increase in the proportion of cells which are dividing (G. Grove, Int. J. Dermatol. 18:111, 1979). Chronic eczema is also associated with significant hyperproliferation of the epidermis. Other diseases caused by hyperproliferation of skin cells include atopic dermatitis, lichen planus, warts, pemphigus vulgaris, actinic keratosis, basal cell carcinoma and squamous cell carcinoma.

Other hyperproliferative cell disorders include blood vessel proliferation disorders, fibrotic disorders, autoimmune disorders, graft-versus-host rejection, tumors and cancers.

Blood vessel proliferative disorders include angiogenic and vasculogenic disorders. Proliferation of smooth muscle cells in the course of development of plaques in vascular tissue cause, for example, restenosis, retinopathies and atherosclerosis. The advanced lesions of atherosclerosis result from an excessive inflammatory-proliferative response to an insult to the endothelium and smooth muscle of the artery wall (Ross, R. Nature, 1993, 362:801-809). Both cell migration and cell proliferation play a role in the formation of atherosclerotic lesions.

Fibrotic disorders are often due to the abnormal formation of an extracellular matrix. Examples of fibrotic disorders include hepatic cirrhosis and mesangial proliferative cell disorders. Hepatic cirrhosis is characterized by the increase in extracellular matrix constituents resulting in the formation of a hepatic scar. Hepatic cirrhosis can cause diseases such as cirrhosis of the liver. An increased extracellular matrix resulting in a hepatic scar can also be caused by viral infection such as hepatitis. Lipocytes appear to play a major role in hepatic cirrhosis.

Mesangial disorders are brought about by abnormal proliferation of mesangial cells. Mesangial hyperproliferative cell disorders include various human renal diseases, such as glomerulonephritis, diabetic nephropathy, malignant nephrosclerosis, thrombotic microangiopathy syndromes, transplant rejection, and glomerulopathies.

Another disease with a proliferative component is rheumatoid arthritis. Rheumatoid arthritis is generally considered an autoimmune disease that is thought to be associated with activity of autoreactive T cells (See, e.g., Harris, E. D., Jr. (1990) The New England Journal of Medicine, 322:1277-1289), and to be caused by auto-antibodies produced against collagen and IgE.

Other disorders that can include an abnormal cellular proliferative component include Behcet's syndrome, acute respiratory distress syndrome (ARDS), ischemic heart disease, post-dialysis syndrome, leukemia, acquired immune deficiency syndrome, vasculitis, lipid histiocytosis, septic shock and inflammation in general.

Examples of cancers or proliferative disorders which can be the primary tumor that is treated include but are not limited to neoplasms located in the: colon, abdomen, bone, breast, digestive system, liver, pancreas, peritoneum, endocrine glands (adrenal, parathyroid, pituitary, testicles, ovary, thymus, thyroid), eye, head and neck, nervous (central and peripheral), lymphatic system, pelvis, skin, soft tissue, spleen, thorax, and urogenital tract.

In certain embodiments, the subject is diagnosed with acute childhood lymphoblastic leukemia; acute lymphoblastic leukemia, acute lymphocytic leukemia, acute myeloid leukemia, adrenocortical carcinoma, adult (primary) hepatocellular cancer, adult (primary) liver cancer, adult acute lymphocytic leukemia, adult acute myeloid leukemia, adult Hodgkin's disease, adult Hodgkin's lymphoma, adult lymphocytic leukemia, adult non-Hodgkin's lymphoma, adult primary liver cancer, adult soft tissue sarcoma, AIDS-related lymphoma, AIDS-related malignancies, anal cancer, astrocytoma, bile duct cancer, bladder cancer, bone cancer, brain stem glioma, brain tumors, breast cancer, cancer of the renal pelvis and ureter, central nervous system (primary) lymphoma, central nervous system lymphoma, cerebellar astrocytoma, cerebral astrocytoma, cervical cancer, childhood (primary) hepatocellular cancer, childhood (primary) liver cancer, childhood acute lymphoblastic leukemia, childhood acute myeloid leukemia, childhood brain stem glioma, childhood cerebellar astrocytoma, childhood cerebral astrocytoma, childhood extracranial germ cell tumors, childhood Hodgkin's disease, childhood Hodgkin's lymphoma, childhood hypothalanic and visual pathway glioma, childhood lymphoblastic leukemia, childhood medulloblastoma, childhood non-Hodgkin's lymphoma, childhood pineal and supratentorial primitive neuroectodermal tumors, childhood primary liver cancer, childhood rhabdomyosarcoma, childhood soft tissue sarcoma, childhood visual pathway and hypothalamic glioma, chronic lymphocytic leukemia, chronic myelogenous leukemia, colon cancer, cutaneous T-cell lymphoma, endocrine pancreas islet cell carcinoma, endometrial cancer, ependymoma, epithelial cancer, esophageal cancer, Ewing's sarcoma and related tumors, exocrine pancreatic cancer, extracranial germ cell tumor, extragonadal germ cell tumor, extrahepatie bile duct cancer, eye cancer, female Breast cancer, Gaucher's disease, gallbladder cancer, gastric cancer, gastrointestinal carcinoid tumor, gastrointestinal tumors, germ cell tumors, gestational trophoblastic tumor, hairy cell leukemia, head and neck cancer, hepatocellular cancer, Hodgkin's disease, Hodgkin's lymphoma, hypergammaglobulinemia, hypopharyngeal cancer, intestinal cancers, intraocular melanoma, islet cell carcinoma, islet cell pancreatic cancer, Kaposi's sarcoma, kidney cancer, laryngeal cancer, lip and oral cavity cancer, liver cancer, lung cancer, lympho proliferative disorders, macroglobulinemia, male breast cancer, malignant mesothelioma, malignant thymoma, medulloblastomia, melanoma, mesothelioma, metastatie occult primary squamous neck cancer, metastatie primary squamous neck cancer, metastatie squamous neck cancer, multiple myeloma, multiple myeloma/plasma cell neoplasm, myelodysplasia syndrome, myelogenous leukemia, myeloid leukemia, myeloproliferative disorders, nasal cavity and paranasal sinus cancer, nasopharyngeal cancer, neuroblastoma, non-Hodgkin's lymphoma during pregnancy, nonmelanoma skin cancer, non-small cell lung cancer, occult primary metastatie squamous neck cancer, oropharyngeal cancer, osteo/malignant fibrous sarcoma, osteosarcoma/malignant fibrous histiocytoma, osteosarcoma/malignant fibrous histiocytoma of bone, ovarian epithelial cancer, ovarian germ cell tumor, ovarian low malignant potential tumor, pancreatic cancer, paraproteinemias, purpura, parathyroid, cancer, penile cancer, pheochromocytoma, pituitary tumor, plasma cell neoplasm/multiple myeloma, primary central nervous system lymphoma, primary liver cancer, prostate cancer, rectal cancer, renal cell cancer, renal pelvis and ureter cancer, retinoblastoma, rhabdomyosarcoma, salivary gland cancer, sarcoidosis sarcomas, sezary syndrome, skin cancer, small cell lung cancer, small Intestine cancer, soft tissue sarcoma, squamous neck cancer, stomach cancer, supratentorial primitive neuroectodermal and pineal tumors, T-cell lymphoma, testicular cancer, thymoma, thyroid cancer, transitional cell cancer of the renal pelvis and ureter, transitional renal pelvis and ureter cancer, trophoblastic tumors, ureter and renal pelvis cell cancer, urethial cancer, uterine cancer, uterine sarcoma, vaginal cancer, visual pathway and hypothalamic glioma, vulvar cancer, Waldenstrom's macroglobulinemia, Wilm's tumor, and any other hyperproliferative disease located in an organ system listed above.

In certain embodiments, the compound disclosed herein can be used to treat or prevent hyperplastic disorders including, but are not limited to, angiofollicular mediastinal lymph node hyperplasia, angiolymphoid hyperplasia with eosinophilia, atypical melanocytic hyperplasia, basal cell hyperplasia, benign giant lymph node hyperplasia, cementum hyperplasia, congenital adrenal hyperplasia, congenital sebaceous hyperplasia, cystic hyperplasia, cystic hyperplasia of the breast, denture hyperplasia, ductal hyperplasia, endometrial hyperplasia, fibromuscular hyperplasia, foca epithelial hyperplasia, gingival hyperplasia, inflammatory fibrous hyperplasia, inflammatory papillary hyperplasia, intravascular papillary endothelial hyperplasia, nodular hyperplasia of prostate, nodular regenerative hyperplasia, pseudoepitheliomatous hyperplasia, senile sebaceous hyperplasia, and verrucous hyperplasia; leukemia (including acute leukemia (e.g., acute lymphocytic leukemia, acute myelocytic leukemia (including myeloblasts, promyelocyte, mylomonocytic, monocytic, and erythroleukemia)) and chronic leukemia (e.g., chronic myelocytic (granulocytic) leukemia and chronic lymphocytic leukemia)), polycythemia vera, lymphomas (e.g., Hodgkin's disease and non-Hodgkin's disease), multiple myeloma, Waldenstrom's macroglobulinemia, heavy chain disease, and solid tumors including, but not limited to, sarcomas and, carcinomas such as fibrosarcoma, myxosarcoma, fiposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, emangioblastoma, acoustic neuroma, oligodendrogliomia, menangioma, melanoma, neuroblastoma, and retinoblastoma.

In a separate embodiment, the disclosure relates to a method for the treatment of, prevention of, or reduced severity of, age-related macular degeneration (ARMD) and other pathogenic states involving macular retinal pigment epithelial (RPE) cells by administering at least one compound described herein to a subject in need thereof.

CXCR4 plays a role in ocular diseases involving the retina such as age-related macular degeneration (ARMD). The retinal pigment epithelium has a major role in the physiological renewal of photoreceptor outer segments in the provision of a transport and storage system for nutrients essential to the photoreceptor layer. The retinal pigment epithelial (RPE) cells predominantly express CXCR4 receptors. (Crane, et al. (2000) J. Immunol. 165: 4372-4278). CXCR4 receptor expression on human retinal pigment epithelial cells from the blood-retina barrier leads to chemokine secretion and migration in response to stromal cell-derived factor Ia. J. Immunol. 200; 165: 4372-4278). The level of CXCR4 mRNA expression increases upon stimulation with IL-1β or TNFα (Dwinell, et al. (1999) Gastroenterology. 117: 359-367). RPE cells also migrated in response to SDF-1αindicating that SDF-1α/CXCR4 interactions may modulate the affects of chronic inflammation and subretinal neovascularization at the RPE site of the blood-retina barrier. (Crane U, Wallace C A, McKillop-Smith S, Forrester J V. CXCR4 receptor expression on human retinal pigment epithelial cells from the blood-retina barrier leads to chemokine secretion and migration in response to stromal cell-derived factor Ia. J. Immunol. 200; 165: 4372-4278).

Age-related macular degeneration is characterized by both primary and secondary damage of macular RPE cells. Early stages of ARMD are characterized by macular drusen, and irregular proliferation and atrophy of the RPE. The late stages of ARMD present with geographic RPE atrophy, RPE detachment and rupture, choroidal neovascularaization and fibrovascular disciform scarring. Common first symptoms include metamorphopisia and/or general central vision loss resulting in reading disability and difficulties in detecting faces. Late stages of ARMD cause central scomota, which is extremely disabling if occurrence is bilateral (Bressler and Bressler (1995) Ophthalmology. 1995; 102: 1206-1211).

In a separate embodiment, a method for the treatment of, prevention of, or reduced severity of inflammatory disease states, neovascularization, and wound healing including administering at least one compound described herein to a subject in need thereof. Vascular endothelial cells express a multitude of chemokine receptors, with CXCR4 being particularly prominent (Gupta, et al. (1998) J Biol Chem. 273: 4282; Volin, et al. (1998) Biochem Biophys Res Commnun. 242: 46).

A RT-PCR based strategy which utilized CXCR4 specific primers demonstrated that mRNA for the chemokine receptor CXCR4 is expressed not only in primary cultures and transformed type II alveolar epithelial cells (pneumocytes) but also in a number of epithelial cell lines derived from various other tissues. (Murdoch, et al. (1998) Immunology. 98(1): 36-41). Unlike with endothelial cells, CXCR4 is the only chemokine receptor expressed on epithelial cells. The receptor may have a functional role in epithelial pathology. CXCR4 expressed on the epithelium may facilitate the recruitment of phagocytic cells to sites of inflammation by direct effects on epithelial cells. CXCR4 may also have other functional roles within the immune response or participate in wound healing or neovascularization. CXCR4 may also be involved in the pathophysiology of several acute or chronic inflammatory disease states associated with the epithelium.

Certain inflammatory chemokines can be induced during an immune response to promote cells of the immune system to a site of infection. Inflammatory chemokines function mainly as chemoattractants for leukocytes, recruiting monocytes, neutrophils and other effector cells from the blood to sites of infection or tissue damage. Certain inflammatory chemokines activate cells to initiate an immune response or promote wound healing. Responses to chemokines include increasing or decreasing expression of membrane proteins, proliferation, and secretion of effector molecules.

In a particular embodiment, the compounds of the disclosure can be administered to a host at risk of, or suffering from, an inflammatory condition. In one embodiment, the compounds are administered for the treatment or prophylaxis of an inflammatory disorder. In certain embodiments, the inflammatory disorder or condition is mediated by chemokines.

Generally, inflammatory disorders include, but are not limited to, respiratory disorders (including asthma, COPD, chronic bronchitis and cystic fibrosis); cardiovascular related disorders (including atherosclerosis, post-angioplasty, restenosis, coronary artery diseases and angina); inflammatory diseases of the joints (including rheumatoid and osteoarthritis); skin disorders (including dermatitis, eczematous dermatitis and psoriasis); post transplantation late and chronic solid organ rejection; multiple sclerosis; autoimmune conditions (including systemic lupus erythematosus, dermatomyositis, polymyositis, Sjogren's syndrome, polymyalgia rheumatica, temporal arteritis, Behcet's disease, Guillain Barre, Wegener's granulomatosus, polyarteritis nodosa); inflammatory neuropathies (including inflammatory polyneuropathies); vasculitis (including Churg-Strauss syndrome, Takayasu's arteritis); inflammatory disorders of adipose tissue; and proliferative disorders (including Kaposi's sarcoma and other proliferative disorders of smooth muscle cells).

In one embodiment, compounds, compositions and methods of treatment of respiratory disorders comprising administering a compound as described herein to a subject in need thereof. Respiratory disorders that may be prevented or treated include a disease or disorder of the respiratory system that can affect any part of the respiratory tract. Respiratory disorders include, but are not limited to, a cold virus, bronchitis, pneumonia, tuberculosis, irritation of the lung tissue, hay fever and other respiratory allergies, asthma, bronchitis, simple and mucopurulent chronic bronchitis, unspecified chronic bronchitis (including chronic bronchitis NOS, chronic tracheitis and chronic tracheobronchitis), emphysema, other chronic obstructive pulmonary disease, asthma, status asthmaticus and bronchiectasis. Other respiratory disorders include allergic and non-allergic rhinitis as well as non-malignant proliferative and/or inflammatory disease of the airway passages and lungs. Non-malignant proliferative and/or inflammatory diseases of the airway passages or lungs means one or more of (1) alveolitis, such as extrinsic allergic alveolitis, and drug toxicity such as caused by, e.g. cytotoxic and/or alkylating agents; (2) vasculitis such as Wegener's granulomatosis, allergic granulomatosis, pulmonary hemangiomatosis and idiopathic pulmonary fibrosis, chronic eosinophilic pneumonia, eosinophilic granuloma and sarcoidoses.

In one embodiment, the compounds of the disclosure are administered to a patient suffering from a cardiovascular disorder related to inflammation. Cardiovascular inflammatory disorders include atherosclerosis, post-angioplasty, restenosis, coronary artery diseases, angina, and other cardiovascular diseases.

In certain embodiments the disorder is a non-cardiovascular inflammatory disorder such as rheumatoid and osteoarthritis, dermatitis, psoriasis, cystic fibrosis, post transplantation late and chronic solid organ rejection, eczematous dermatitis, Kaposi's sarcoma, or multiple sclerosis. In yet another embodiment, the compounds disclosed herein can be selected to treat anti-inflammatory conditions that are mediated by mononuclear leucocytes.

In addition, the disclosure is directed to methods of treating animal subjects, in particular, veterinary and human subjects, to enhance or elevate the number of progenitor cells and/or stem cells. The progenitor and/or stem cells may be harvested and used in cell transplantation. In one embodiment, bone marrow progenitor and/or stem cells are mobilized for myocardial repair. Further, the disclosure is directed to methods of treating animal subjects, in particular, veterinary and human patients, who are defective in white blood cell (WBQ 8 count, or who would benefit from elevation of WBC levels using the compounds disclosed herein. Moreover, the disclosure is directed to methods of effecting regeneration of cardiac tissue in a subject in need of such regeneration using the disclosed compounds.

The compounds of the disclosure may be used for the treatment of diseases that are associated with immunosuppression such as individuals undergoing chemotherapy, radiation therapy, enhanced wound healing and bum treatment, therapy for autoimmune disease or other drug therapy (e.g., corticosteroid therapy) or combination of conventional drugs used in the treatment of autoimmune diseases and graft/transplantation rejection, which causes immunosuppression; immunosuppression due to congenital deficiency in receptor function or other causes; and infectious diseases, such as parasitic diseases, including but not limited to, helminth infections, such as nematodes (round disclosure thus targets a broad spectrum of conditions for which elevation of progenitor cells and/or stem cells in a subject would be beneficial or, where harvesting of progenitor cells and/or stem cell for subsequent stem cell transplantation would be beneficial. In addition, the method of the disclosure targets a broad spectrum of conditions characterized by a deficiency in white blood cell count, or which would benefit from elevation of said WBC count.

In certain embodiments, the compounds described herein are useful for the treatment of viral infections where the virus utilized CXCR4 to infect cells.

In one embodiment, the disclosure relates to a method of treating or preventing HIV infection or reduction of symptoms associated with AIDS is provided including administering a compound disclosed herein to a subject. In certain embodiments, the compound can be provided to a subject before treatment of infection with another compound. In a separate embodiment, the compound is provided to a patient that has been treated for HIV infection to reduce the likelihood of recurrence, or reduce mortality associated with AIDS related symptoms. In another embodiment, the compound is administered to a subject at high risk of suffering from HIV infections.

HIV is a lentivirus (a member of the retrovirus family) that causes acquired immunodeficiency syndrome (AIDS). Lentiviruses are transmitted as single-stranded, positive-sense, enveloped RNA viruses. Upon entry of the target cell, the viral RNA genome is converted to double-stranded DNA by a virally encoded reverse transcriptase. This viral DNA is then integrated into the cellular DNA by a virally encoded integrase, along with host cellular co-factors. There are two species of HIV. HIV-1 is sometimes termed LAV or HTLV-III.

HIV infects primarily vital cells in the human immune system such as helper T cells (CD4+ T cells), macrophages, and dendritic cells. HIV infection leads to low levels of CD4+ T cells. When CD4+ T cell numbers decline below a critical level, cell-mediated immunity is lost, and the body becomes progressively more susceptible to other viral or bacterial infections. Subjects with HIV typically develop malignancies associated with the progressive failure of the immune system.

The viral envelope is composed of two layers of phospholipids taken from the membrane of a human cell when a newly formed virus particle buds from the cell. Embedded in the viral envelope are proteins from the host cell and a HIV protein known as Env. Env contains glycoproteins gp120, and gp41. The RNA genome consists of at structural landmarks (LTR, TAR, RRE, PE, SLIP, CRS, and INS) and nine genes (gag, pol, and env, tat, rev, nef, vif, vpr, vpu, and sometimes a tenth tev, which is a fusion of tat env and rev) encoding 19 proteins. Three of these genes, gag, pol, and env, contain information needed to make the structural proteins for new virus particles. HIV-1 diagnosis is typically done with antibodies in an ELISA, Western blot, or immunoaffinity assays or by nucleic acid testing (e.g., viral RNA or DNA amplification).

Subjects, including humans suffering from, or at risk for, HIV infection can be treated by administering an effective amount of the active compound or a pharmaceutically acceptable prodrug or salt thereof in the presence of a pharmaceutically acceptable carrier or diluent.

The administration can be prophylactically for the prevention of HIV infection or reduction of symptoms associated with AIDS. The active materials can be administered by any appropriate route, for example, orally, parenterally, intravenously, intradermally, subcutaneously, or topically, in liquid or solid form. However, the compounds are particularly suited to oral delivery.

In a separate embodiment, a method for the treatment or prevention of HIV infection or reduction of symptoms associated with AIDS by administering a compound of the present disclosure, or a pharmaceutically acceptable salt, solvate, prodrug, or ester thereof to a subject in need of treatment is provided. The compounds of the disclosure, or a pharmaceutically acceptable salt, solvate, prodrug, or ester thereof can be administered to a subject in need thereof to reduce the severity of AIDS related disorders. In one embodiment of the disclosure, the subject is a human.

In a separate embodiment, a method for the treatment of, prevention of, or reduced severity of liver disease associated with viral infections including administering at least one compound described herein is provided.

Chronic hepatitis C virus (HCV) and hepatitis B virus (HBC) infection is accompanied by inflammation and fibrosis eventually leading to cirrhosis. A study testing the expression and function of CXCR4 on liver-infiltrating lymphocytes (LIL) revealed an important role for the CXCL12/CXCR4 pathway in recruitment and retention of immune cells in the liver during chronic HCV and HBV infection (Wald et al., (2004) European Journal of Immunology. 34(4): 1164-1174). High levels of CXCR4 and TGFβ have been detected in liver samples obtained from patients infected with HCV. (Mitra et al., (1999) Int. J. Oncol. 14: 917-925). In vitro, TGF-β has been shown to up-regulate the expression of CXCR4 on T cells and to increase their migration. The CD69/TGFβ/CXCR4 pathway may be involved in the retention of recently activated lymphocytes in the liver (Wald et al., European Journal of Immunology, 2004; 34(4): 1164-1174).

In another embodiment, the disclosure relates to a method of treating symptoms associated with other infections associated with chemokine receptor activation, for example, liver diseases associated with flavivirus or pestivirus infection, and in particular, HCV or HBV, by contacting a cell with a compound of the present disclosure, or a pharmaceutically acceptable salt, solvate, prodrug, or ester thereof. The cell can be in a subject animal, in particular in a human.

Combination Therapies

In certain embodiments, the disclosure relates to pharmaceutical compositions comprising CXCR4 modulators disclosed herein with another active ingredient.

The cancer treatment may be applied as a sole therapy or may involve, conventional surgery or radiotherapy or chemotherapy. Such chemotherapy may include one or more of the following categories of anti-tumour agents:

(i) antiproliferative/antineoplastic drugs and combinations thereof, as used in medical oncology, such as alkylating agents (for example cis-platin, carboplatin, cyclophosphamide, nitrogen mustard, melphalan, chlorambucil, busulfan and nitrosoureas); antimetabolites (for example antifolates such as fluoropyrimidines like 5-fluorouracil and gemcitabine, tegafur, raltitrexed, methotrexate, cytosine arabinoside and hydroxyurea); antitumour antibiotics (for example anthracyclines like adriamycin, bleomycin, doxorubicin, daunomycin, epirubicin, idarubicin, mitomycin-C, dactinomycin and mithramycin); antimitotic agents (for example vinca alkaloids like vincristine, vinblastine, vindesine and vinorelbine and taxoids like taxol and taxotere); and topoisomerase inhibitors (for example epipodophyllotoxins like etoposide and teniposide, amsacrine, topotecan and camptothecin); and proteosome inhibitors (for example bortezomib [Velcade®]); and the agent anegrilide [Agrylin®]; and the agent alpha-interferon (ii) cytostatic agents such as antioestrogens (for example tamoxifen, toremifene, raloxifene, droloxifene and iodoxyfene), oestrogen receptor down regulators (for example fulvestrant), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrozole, vorazole and exemestane) and inhibitors of 5α-reductase such as finasteride;

(iii) agents which inhibit cancer cell invasion (for example metalloproteinase inhibitors like marimastat and inhibitors of urokinase plasminogen activator receptor function);

(iv) inhibitors of growth factor function, for example such inhibitors include growth factor antibodies, growth factor receptor antibodies (for example the anti-Her2 antibody trastuzumab and the anti-epidermal growth factor receptor (EGFR) antibody, cetuximab), farnesyl transferase inhibitors, tyrosine kinase inhibitors and serine/threonine kinase inhibitors, for example inhibitors of the epidermal growth factor family (for example EGFR family tyrosine kinase inhibitors such as: N-(3-chloro-4-fluorophenyl)-7-methoxy-6-(3-morpholinopropoxy)quinazolin-4-amine (gefitinib), N-(3-ethynylphenyl)-6,7-bis(2-methoxyethoxy)quinazolin-4-amine (erlotinib), and 6-acrylamido-N-(3-chloro-4-fluorophenyl)-7-(3-morpholinopropoxy)quinazolin-4-amine (CI 1033), for example inhibitors of the platelet-derived growth factor family and for example inhibitors of the hepatocyte growth factor family, for example inhibitors or phosphotidylinositol 3-kinase (PI3K) and for example inhibitors of mitogen activated protein kinase kinase (MEK1/2) and for example inhibitors of protein kinase B (PKB/Akt), for example inhibitors of Src tyrosine kinase family and/or Abelson (AbI) tyrosine kinase family such as dasatinib (BMS-354825) and imatinib mesylate (Gleevec™); and any agents that modify STAT signalling;

(v) antiangiogenic agents such as those which inhibit the effects of vascular endothelial growth factor, (for example the anti-vascular endothelial cell growth factor antibody bevacizumab [Avastin™]) and compounds that work by other mechanisms (for example linomide, inhibitors of integrin ocvβ3 function and angiostatin);

(vi) vascular damaging agents such as Combretastatin A4;

(vii) antisense therapies, for example those which are directed to the targets listed above, such as an anti-ras antisense; and (viii) immunotherapy approaches, including for example ex-vivo and in-vivo approaches to increase the immunogenicity of patient tumour cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumour cell lines and approaches using anti-idiotypic antibodies, and approaches using the immunomodulatory drugs thalidomide and lenalidomide [Revlimid®].

In certain embodiments, the disclosure relates to administering chemokine CXCR4 receptor modulators disclosed herein in combination with natural ligands of CXCR4. The natural ligands for the chemokine receptor CXCR4 (SDF-1) can act as potent inhibitors of infection by the human immunodeficiency virus type 1 (HIV-1) at the level of viral entry. Unlike antibody-mediated inhibition, chemokine-mediated inhibition is broadly effective. Different HIV-1 strains can utilize the same co-receptor(s) for viral entry and, therefore, can be blocked by the same chemokine(s). HIV-1 strains that are highly resistant to neutralization by V3-specific antibodies are sensitive to inhibition by chemokines. Therefore, the use of chemokine-modulators constitutes a therapeutic approach to prevent infection by HIV-1. Alkhatib et al., Science. 1996, 272: 1955-1988 and Challita-Eid et al., AIDS Research and Human Retroviruses, 1998, 14(18): 1617-1624.

In some embodiments, the disclosure relates to treating a viral infection by administering a CXCR4 modulator in combination with another, second antiviral agent. In specific embodiments, the compounds described herein are administered in combination or alternation with at least one compound that inhibits HIV entry into a cell through a mechanism not dependent on CXCR4, and in particular embodiments, are administered in combination or alternation with a compound that inhibits CCR5, gp120, gp41 or CD4 binding or activity. In some embodiments, such a compound is at least one of Maraviroc (Celsentri) or Enfuvirtide (Fuzeon). In yet further embodiments such compound is selected from TNX-355, PRO 250, BMS-488043, a theaflavin, Vicriviroc, Gruffithsin, DCM205, ESN196, TBR220, TMB355, Nifeviroc, BMS663068, CYT107, Sifuvirtide, AMD070, PF232798, SP01A.

In further embodiments, the subject is co-administered with abacavir, acyclovir, acyclovir, adefovir, amantadine, amprenavir, ampligen, arbidol, atazanavir, atripla, boceprevir, cidofovir, combivir,darunavir, delavirdine, didanosine, docosanol, edoxudine, efavirenz, emtricitabine, enfuvirtide, entecavir, famciclovir, fomivirsen, fosamprenavir, foscarnet, fosfonet, ganciclovir, ibacitabine, imunovir, idoxuridine, imiquimod, indinavir, inosine, interferon type III, interferon type II, interferon type I, lamivudine, lopinavir, loviride, maraviroc, moroxydine, methisazone, nelfinavir, nevirapine, nexavir, oseltamivir (Tamiflu), peginterferon alfa-2a, penciclovir, peramivir, pleconaril, podophyllotoxin, raltegravir, ribavirin, rimantadine, ritonavir, pyramidine, saquinavir, stavudine, tenofovir, tenofovir disoproxil, tipranavir, trifluridine, trizivir, tromantadine, truvada, valaciclovir (Valtrex), valganciclovir, vicriviroc, vidarabine, viramidine zalcitabine, zanamivir (Relenza), and/or zidovudine.

HIV is typically treated with a combination of antiviral agent, e.g., two nucleoside-analogue reverse transcription inhibitors and one non-nucleoside-analogue reverse transcription inhibitor or protease inhibitor. The three drug combination is commonly known as a triple cocktail. In certain embodiments, the disclosure relates to treating a subject diagnosed with HIV by administering a chemokine CXCR4 receptor modulator disclosed herein in combination with two nucleoside-analogue reverse transcription inhibitors and/or one non-nucleoside-analogue reverse transcription inhibitor or protease inhibitor.

In certain embodiments, the disclosure relates to treating a subject by administering a chemokine CXCR4 receptor modulator disclosed herein, emtricitabine, tenofovir, and efavirenz. In certain embodiments, the disclosure relates to treating a subject by administering a chemokine CXCR4 receptor modulator disclosed herein, emtricitabine, tenofovir and raltegravir. In certain embodiments, the disclosure relates to treating a subject by administering a chemokine CXCR4 receptor modulator disclosed herein, emtricitabine, tenofovir, ritonavir and darunavir. In certain embodiments, the disclosure relates to treating a subject by administering a chemokine CXCR4 receptor modulator disclosed herein, emtricitabine, tenofovir, ritonavir and atazanavir.

In certain embodiments, the disclosure relates to administering a CXCR4 antagonist disclosed herein in combination with a CCR5 antagonist such as maraviroc (selzentry) or vicriviroc.

Banana lectin (BanLec or BanLec-1) is one of the predominant proteins in the pulp of ripe bananas and has binding specificity for mannose and mannose-containing oligosaccharides. BanLec binds to the HIV-1 envelope protein gp120. In certain embodiments, the disclosure relates to treating viral infections, such as HIV, by administering a chemokine CXCR4 receptor modulator disclosed herein in combination with a banana lectin.

Formulations

Pharmaceutical compositions disclosed herein may be in the form of pharmaceutically acceptable salts, as generally described below. Some preferred, but non-limiting examples of suitable pharmaceutically acceptable organic and/or inorganic acids are hydrochloric acid, hydrobromic acid, sulfuric acid, nitric acid, acetic acid and citric acid, as well as other pharmaceutically acceptable acids known per se (for which reference is made to the references referred to below).

When the compounds of the disclosure contain an acidic group as well as a basic group, the compounds of the disclosure may also form internal salts, and such compounds are within the scope of the disclosure. When a compound contains a hydrogen-donating heteroatom (e.g. NH), salts are contemplated to covers isomers formed by transfer of said hydrogen atom to a basic group or atom within the molecule.

Pharmaceutically acceptable salts of the compounds include the acid addition and base salts thereof. Suitable acid addition salts are formed from acids which form non-toxic salts. Examples include the acetate, adipate, aspartate, benzoate, besylate, bicarbonate/carbonate, bisulphate/sulphate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, trifluoroacetate and xinofoate salts. Suitable base salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine and zinc salts. Hemisalts of acids and bases may also be formed, for example, hemisulphate and hemicalcium salts. For a review on suitable salts, see Handbook of Pharmaceutical Salts: Properties, Selection, and Use by Stahl and Wermuth (Wiley-VCH, 2002), incorporated herein by reference.

The compounds described herein may be administered in the form of prodrugs. A prodrug can include a covalently bonded carrier which releases the active parent drug when administered to a mammalian subject. Prodrugs can be prepared by modifying functional groups present in the compounds in such a way that the modifications are cleaved, either in routine manipulation or in vivo, to the parent compounds. Prodrugs include, for example, compounds wherein a hydroxyl group is bonded to any group that, when administered to a mammalian subject, cleaves to form a free hydroxyl group. Examples of prodrugs include, but are not limited to, acetate, formate and benzoate derivatives of alcohol functional groups in the compounds. Methods of structuring a compound as prodrugs can be found in the book of Testa and Mayer, Hydrolysis in Drug and Prodrug Metabolism, Wiley (2006). Typical prodrugs form the active metabolite by transformation of the prodrug by hydrolytic enzymes, the hydrolysis of amide, lactams, peptides, carboxylic acid esters, epoxides or the cleavage of esters of inorganic acids.

Pharmaceutical compositions for use in the present disclosure typically comprise an effective amount of a compound and a suitable pharmaceutical acceptable carrier. The preparations may be prepared in a manner known per se, which usually involves mixing the at least one compound according to the disclosure with the one or more pharmaceutically acceptable carriers, and, if desired, in combination with other pharmaceutical active compounds, when necessary under aseptic conditions. Reference is again made to U.S. Pat. Nos. 6,372,778; 6,369,086; 6,369,087 and 6,372,733 and the further references mentioned above, as well as to the standard handbooks, such as the latest edition of Remington's Pharmaceutical Sciences.

Generally, for pharmaceutical use, the compounds may be formulated as a pharmaceutical preparation comprising at least one compound and at least one pharmaceutically acceptable carrier, diluent or excipient and/or adjuvant, and optionally one or more further pharmaceutically active compounds.

The pharmaceutical preparations of the disclosure are preferably in a unit dosage form, and may be suitably packaged, for example in a box, blister, vial, bottle, sachet, ampoule or in any other suitable single-dose or multi-dose holder or container (which may be properly labeled); optionally with one or more leaflets containing product information and/or instructions for use. Generally, such unit dosages will contain between 1 and 1000 mg, and usually between 5 and 500 mg, of the at least one compound of the disclosure, e.g. about 10, 25, 50, 100, 200, 300 or 400 mg per unit dosage.

The compounds can be administered by a variety of routes including the oral, ocular, rectal, transdermal, subcutaneous, intravenous, intramuscular or intranasal routes, depending mainly on the specific preparation used. The compound will generally be administered in an "effective amount", by which is meant any amount of a compound that, upon suitable administration, is sufficient to achieve the desired therapeutic or prophylactic effect in the subject to which it is administered. Usually, depending on the condition to be prevented or treated and the route of administration, such an effective amount will usually be between 0.01 to 1000 mg per kilogram body weight of the patient per day, more often between 0.1 and 500 mg, such as between 1 and 250 mg, for example about 5, 10, 20, 50, 100, 150, 200 or 250 mg, per kilogram body weight of the patient per day, which may be administered as a single daily dose, divided over one or more daily doses. The amount(s) to be administered, the route of administration and the further treatment regimen may be determined by the treating clinician, depending on factors such as the age, gender and general condition of the patient and the nature and severity of the disease/symptoms to be treated. Reference is again made to U.S. Pat. Nos. 6,372,778; 6,369,086; 6,369,087; and 6,372,733 and the further references mentioned above, as well as to the standard handbooks, such as the latest edition of Remington's Pharmaceutical Sciences.

Depending upon the manner of introduction, the compounds described herein may be formulated in a variety of ways. Formulations containing one or more compounds can be prepared in various pharmaceutical forms, such as granules, tablets, capsules, suppositories, powders, controlled release formulations, suspensions, emulsions, creams, gels, ointments, salves, lotions, or aerosols and the like. Preferably, these formulations are employed in solid dosage forms suitable for simple, and preferably oral, administration of precise dosages. Solid dosage forms for oral administration include, but are not limited to, tablets, soft or hard gelatin or non-gelatin capsules, and caplets. However, liquid dosage forms, such as solutions, syrups, suspension, shakes, etc. can also be utilized. In another embodiment, the formulation is administered topically. Suitable topical formulations include, but are not limited to, lotions, ointments, creams, and gels. In a preferred embodiment, the topical formulation is a gel. In another embodiment, the formulation is administered intranasally.

Formulations containing one or more of the compounds described herein may be prepared using a pharmaceutically acceptable carrier composed of materials that are considered safe and effective and may be administered to an individual without causing undesirable biological side effects or unwanted interactions. The carrier is all components present in the pharmaceutical formulation other than the active ingredient or ingredients. As generally used herein "carrier" includes, but is not limited to, diluents, binders, lubricants, disintegrators, fillers, pH modifying agents, preservatives, antioxidants, solubility enhancers, and coating compositions.

Carrier also includes all components of the coating composition which may include plasticizers, pigments, colorants, stabilizing agents, and glidants. Delayed release, extended release, and/or pulsatile release dosage formulations may be prepared as described in standard references such as "Pharmaceutical dosage form tablets", eds. Liberman et. al. (New York, Marcel Dekker, Inc., 1989), "Remington—The science and practice of pharmacy", 20th ed., Lippincott Williams & Wilkins, Baltimore, Md., 2000, and "Pharmaceutical dosage forms and drug delivery systems", 6th Edition, Ansel et al., (Media, PA: Williams and Wilkins, 1995). These references provide information on carriers, materials, equipment and process for preparing tablets and capsules and delayed release dosage forms of tablets, capsules, and granules.

Examples of suitable coating materials include, but are not limited to, cellulose polymers such as cellulose acetate phthalate, hydroxypropyl cellulose, hydroxypropyl methylcellulose, hydroxypropyl methylcellulose phthalate and hydroxypropyl methylcellulose acetate succinate; polyvinyl acetate phthalate, acrylic acid polymers and copolymers, and methacrylic resins that are commercially available under the trade name EUDRAGIT® (Roth Pharma, Westerstadt, Germany), zein, shellac, and polysaccharides.

Additionally, the coating material may contain conventional carriers such as plasticizers, pigments, colorants, glidants, stabilization agents, pore formers and surfactants.

Optional pharmaceutically acceptable excipients present in the drug-containing tablets, beads, granules or particles include, but are not limited to, diluents, binders, lubricants, disintegrants, colorants, stabilizers, and surfactants. Diluents, also referred to as "fillers," are typically necessary to increase the bulk of a solid dosage form so that a practical size is provided for compression of tablets or formation of beads and granules. Suitable diluents include, but are not limited to, dicalcium phosphate dihydrate, calcium sulfate, lactose, sucrose, mannitol, sorbitol, cellulose, microcrystalline cellulose, kaolin, sodium chloride, dry starch, hydrolyzed starches, pregelatinized starch, silicone dioxide, titanium oxide, magnesium aluminum silicate and powdered sugar.

Binders are used to impart cohesive qualities to a solid dosage formulation, and thus ensure that a tablet or bead or granule remains intact after the formation of the dosage forms. Suitable binder materials include, but are not limited to, starch, pregelatinized starch, gelatin, sugars (including sucrose, glucose, dextrose, lactose and sorbitol), polyethylene glycol, waxes, natural and synthetic gums such as acacia, tragacanth, sodium alginate, cellulose, including hydroxypropylmethylcellulose, hydroxypropylcellulose, ethylcellulose, and veegum, and synthetic polymers such as acrylic acid and methacrylic acid copolymers, methacrylic acid copolymers, methyl methacrylate copolymers, aminoalkyl methacrylate copolymers, polyacrylic acid/polymethacrylic acid and polyvinylpyrrolidone.

Lubricants are used to facilitate tablet manufacture. Examples of suitable lubricants include, but are not limited to, magnesium stearate, calcium stearate, stearic acid, glycerol behenate, polyethylene glycol, talc, and mineral oil.

Disintegrants are used to facilitate dosage form disintegration or "breakup" after administration, and generally include, but are not limited to, starch, sodium starch glycolate, sodium carboxymethyl starch, sodium carboxymethylcellulose, hydroxypropyl cellulose, pregelatinized starch, clays, cellulose, alginine, gums or cross linked polymers, such as cross-linked PVP (Polyplasdone XL from GAF Chemical Corp).

Stabilizers are used to inhibit or retard drug decomposition reactions which include, by way of example, oxidative reactions.

Surfactants may be anionic, cationic, amphoteric or nonionic surface active agents. Suitable anionic surfactants include, but are not limited to, those containing carboxylate, sulfonate and sulfate ions. Examples of anionic surfactants include sodium, potassium, ammonium of long chain alkyl sulfonates and alkyl aryl sulfonates such as sodium dodecylbenzene sulfonate; dialkyl sodium sulfosuccinates, such as sodium dodecylbenzene sulfonate; dialkyl sodium sulfosuccinates, such as sodium bis-(2-ethylthioxyl)-sulfosuccinate; and alkyl sulfates such as sodium lauryl sulfate. Cationic surfactants include, but are not limited to, quaternary ammonium compounds such as benzalkonium chloride, benzethonium chloride, cetrimonium bromide, stearyl dimethylbenzyl ammonium chloride, polyoxyethylene and coconut amine. Examples of nonionic surfactants include ethylene glycol monostearate, propylene glycol myristate, glyceryl monostearate, glyceryl stearate, polyglyceryl-4-oleate, sorbitan acylate, sucrose acylate, PEG-150 laurate, PEG-400 monolaurate, polyoxyethylene monolaurate, polysorbates, polyoxyethylene octylphenylether, PEG-1000 cetyl ether, polyoxyethylene tridecyl ether, polypropylene glycol butyl ether, Poloxamer® 401, stearoyl monoisopropanolamide, and polyoxyethylene hydrogenated tallow amide. Examples of amphoteric surfactants include sodium N-dodecyl-beta-alanine, sodium N-lauryl-beta-iminodipropionate, myristoamphoacetate, lauryl betaine and lauryl sulfobetaine.

If desired, the tablets, beads, granules, or particles may also contain minor amount of nontoxic auxiliary substances such as wetting or emulsifying agents, dyes, pH buffering agents, or preservatives.

The concentration of the compound(s) to carrier and/or other substances may vary from about 0.5 to about 100 wt % (weight percent). For oral use, the pharmaceutical formulation will generally contain from about 5 to about 100% by weight of the active material. For other uses, the pharmaceutical formulation will generally have from about 0.5 to about 50 wt. % of the active material.

The compositions described herein can be formulation for modified or controlled release. Examples of controlled release dosage forms include extended release dosage forms, delayed release dosage forms, pulsatile release dosage forms, and combinations thereof.

The extended release formulations are generally prepared as diffusion or osmotic systems, for example, as described in "Remington—The science and practice of pharmacy" (20th ed., Lippincott Williams & Wilkins, Baltimore, Md., 2000). A diffusion system typically consists of two types of devices, a reservoir and a matrix, and is well known and described in the art. The matrix devices are generally prepared by compressing the drug with a slowly dissolving polymer carrier into a tablet form. The three major types of materials used in the preparation of matrix devices are insoluble plastics, hydrophilic polymers, and fatty compounds. Plastic matrices include, but are not limited to, methyl acrylate-methyl methacrylate, polyvinyl chloride, and polyethylene. Hydrophilic polymers include, but are not limited to, cellulosic polymers such as methyl and ethyl cellulose, hydroxyalkylcelluloses such as hydroxypropyl-cellulose, hydroxypropylmethylcellulose, sodium carboxymethylcellulose, and Carbopol® 934, polyethylene oxides and mixtures thereof. Fatty compounds include, but are not limited to, various waxes such as carnauba wax and glyceryl tristearate and wax-type substances including hydrogenated castor oil or hydrogenated vegetable oil, or mixtures thereof.

In certain preferred embodiments, the plastic material is a pharmaceutically acceptable acrylic polymer, including but not limited to, acrylic acid and methacrylic acid copolymers, methyl methacrylate, methyl methacrylate copolymers, ethoxyethyl methacrylates, cyanoethyl methacrylate, aminoalkyl methacrylate copolymer, poly(acrylic acid), poly (methacrylic acid), methacrylic acid alkylamine copolymer poly(methyl methacrylate), poly(methacrylic acid)(anhydride), polymethacrylate, polyacrylamide, poly(methacrylic acid anhydride), and glycidyl methacrylate copolymers.

In certain preferred embodiments, the acrylic polymer is comprised of one or more ammonio methacrylate copolymers. Ammonio methacrylate copolymers are well known in the art, and are described in NF XVII as fully polymerized copolymers of acrylic and methacrylic acid esters with a low content of quaternary ammonium groups.

In one preferred embodiment, the acrylic polymer is an acrylic resin lacquer such as that which is commercially available from Rohm Pharma under the tradename Eudragit®. In further preferred embodiments, the acrylic polymer comprises a mixture of two acrylic resin lacquers commercially available from Rohm Pharma under the tradenames Eudragit® RL30D and Eudragit® RS30D, respectively. Eudragit® RL30D and Eudragit® RS30D are copolymers of acrylic and methacrylic esters with a low content of quaternary ammonium groups, the molar ratio of ammonium groups to the remaining neutral (meth)acrylic esters being 1:20 in Eudragit® RL30D and 1:40 in Eudragit® RS30D. The mean molecular weight is about 150,000. Edragit® S-100 and Eudragit® L-100 are also preferred. The code designations RL (high permeability) and RS (low permeability) refer to the permeability properties of these agents. Eudragit® RL/RS mixtures are insoluble in water and in digestive fluids. However, multiparticulate systems formed to include the same are swellable and permeable in aqueous solutions and digestive fluids.

The polymers described above such as Eudragit® RL/RS may be mixed together in any desired ratio in order to ultimately obtain a sustained-release formulation having a desirable dissolution profile. Desirable sustained-release multiparticulate systems may be obtained, for instance, from 100% Eudragit® RL, 50% Eudragit® RL and 50% Eudragit® RS, and 10% Eudragit® RL and 90% Eudragit® RS. One skilled in the art will recognize that other acrylic polymers may also be used, such as, for example, Eudragit® L.

Alternatively, extended release formulations can be prepared using osmotic systems or by applying a semi-permeable coating to the dosage form. In the latter case, the desired drug release profile can be achieved by combining low permeable and high permeable coating materials in suitable proportion.

The devices with different drug release mechanisms described above can be combined in a final dosage form comprising single or multiple units. Examples of multiple units include, but are not limited to, multilayer tablets and capsules containing tablets, beads, or granules An immediate release portion can be added to the extended release system by means of either applying an immediate release layer on top of the extended release core using a coating or compression process or in a multiple unit system such as a capsule containing extended and immediate release beads.

Extended release tablets containing hydrophilic polymers are prepared by techniques commonly known in the art such as direct compression, wet granulation, or dry granulation. Their formulations usually incorporate polymers, diluents, binders, and lubricants as well as the active pharmaceutical ingredient. The usual diluents include inert powdered substances such as starches, powdered cellulose, especially crystalline and microcrystalline cellulose, sugars such as fructose, mannitol and sucrose, grain flours and similar edible powders. Typical diluents include, for example, various types of starch, lactose, mannitol, kaolin, calcium phosphate or sulfate, inorganic salts such as sodium chloride and powdered sugar. Powdered cellulose derivatives are also useful. Typical tablet binders include substances such as starch, gelatin and sugars such as lactose, fructose, and glucose. Natural and synthetic gums, including acacia, alginates, methylcellulose, and polyvinylpyrrolidone can also be used. Polyethylene glycol, hydrophilic polymers, ethylcellulose and waxes can also serve as binders. A lubricant is necessary in a tablet formulation to prevent the tablet and punches from sticking in the die. The lubricant is chosen from such slippery solids as talc, magnesium and calcium stearate, stearic acid and hydrogenated vegetable oils.

Extended release tablets containing wax materials are generally prepared using methods known in the art such as a direct blend method, a congealing method, and an aqueous dispersion method. In congealing method, the drug is mixed with a wax material and either spray-congealed or congealed and screened and processed.

Delayed release formulations are created by coating a solid dosage form with a polymer film, which is insoluble in the acidic environment of the stomach, and soluble in the neutral environment of the small intestine.

The delayed release dosage units can be prepared, for example, by coating a drug or a drug-containing composition with a selected coating material. The drug-containing composition may be, e.g., a tablet for incorporation into a capsule, a tablet for use as an inner core in a "coated core" dosage form, or a plurality of drug-containing beads, particles or granules, for incorporation into either a tablet or capsule. Preferred coating materials include bioerodible, gradually hydrolyzable, gradually water-soluble, and/or enzymatically degradable polymers, and may be conventional "enteric" polymers. Enteric polymers, as will be appreciated by those skilled in the art, become soluble in the higher pH environment of the lower gastrointestinal tract or slowly erode as the dosage form passes through the gastrointestinal tract, while enzymatically degradable polymers are degraded by bacterial enzymes present in the lower gastrointestinal tract, particularly in the colon. Suitable coating materials for effecting delayed release include, but are not limited to, cellulosic polymers such as hydroxypropyl cellulose, hydroxyethyl cellulose, hydroxymethyl cellulose, hydroxypropyl methyl cellulose, hydroxypropyl methyl cellulose acetate succinate, hydroxypropylmethyl cellulose phthalate, methylcellulose, ethyl cellulose, cellulose acetate, cellulose acetate phthalate, cellulose acetate trimellitate and carboxymethylcellulose sodium; acrylic acid polymers and copolymers, preferably formed from acrylic acid, methacrylic acid, methyl acrylate, ethyl acrylate, methyl methacrylate and/or ethyl methacrylate, and other methacrylic resins that are commercially available under the tradename Eudragit® (Rohm Pharma; Westerstadt, Germany), including Eudragit® L30D-55 and L100-55 (soluble at pH 5.5 and above), Eudragit® L-100 (soluble at pH 6.0 and above), Eudragit® S (soluble at pH 7.0 and above, as a result of a higher degree of esterification), and Eudragits® NE, RL and RS (water-insoluble polymers having different degrees of permeability and expandability); vinyl polymers and copolymers such as polyvinyl pyrrolidone, vinyl acetate, vinylacetate phthalate, vinylacetate crotonic acid copolymer, and ethylene-vinyl acetate copolymer; enzymatically degradable polymers such as azo polymers, pectin, chitosan, amylose and guar gum; zein and shellac. Combinations of different coating materials may also be used. Multi-layer coatings using different polymers may also be applied.

The preferred coating weights for particular coating materials may be readily determined by those skilled in the art by evaluating individual release profiles for tablets, beads and granules prepared with different quantities of various coating materials. It is the combination of materials, method and form of application that produce the desired release characteristics, which one can determine only from the clinical studies.

The coating composition may include conventional additives, such as plasticizers, pigments, colorants, stabilizing agents, glidants, etc. A plasticizer is normally present to reduce the fragility of the coating, and will generally represent about 10 wt. % to 50 wt. % relative to the dry weight of the polymer. Examples of typical plasticizers include polyethylene glycol, propylene glycol, triacetin, dimethyl phthalate, diethyl phthalate, dibutyl phthalate, dibutyl sebacate, triethyl citrate, tributyl citrate, triethyl acetyl citrate, castor oil and acetylated monoglycerides. A stabilizing agent is preferably used to stabilize particles in the dispersion. Typical stabilizing agents are nonionic emulsifiers such as sorbitan esters, polysorbates and polyvinylpyrrolidone. Glidants are recommended to reduce sticking effects during film formation and drying, and will generally represent approximately 25 wt. % to 100 wt. % of the polymer weight in the coating solution. One effective glidant is talc. Other glidants such as magnesium stearate and glycerol monostearates may also be used. Pigments such as titanium dioxide may also be used. Small quantities of an anti-foaming agent, such as a silicone (e.g., simethicone), may also be added to the coating composition.

The formulation can provide pulsatile delivery of the one or more compounds. By "pulsatile" is meant that a plurality of drug doses are released at spaced apart intervals of time. Generally, upon ingestion of the dosage form, release of the initial dose is substantially immediate, i.e., the first drug release "pulse" occurs within about one hour of ingestion. This initial pulse is followed by a first time interval (lag time) during which very little or no drug is released from the dosage form, after which a second dose is then released. Similarly, a second nearly drug release-free interval between the second and third drug release pulses may be designed. The duration of the nearly drug release-free time interval will vary depending upon the dosage form design e.g., a twice daily dosing profile, a three times daily dosing profile, etc. For dosage forms providing a twice daily dosage profile, the nearly drug release-free interval has a duration of approximately 3 hours to 14 hours between the first and second dose. For dosage forms providing a three times daily profile, the nearly drug release-free interval has a duration of approximately 2 hours to 8 hours between each of the three doses.

In one embodiment, the pulsatile release profile is achieved with dosage forms that are closed and preferably sealed capsules housing at least two drug-containing "dosage units" wherein each dosage unit within the capsule provides a different drug release profile. Control of the delayed release dosage unit(s) is accomplished by a controlled release polymer coating on the dosage unit, or by incorporation of the active agent in a controlled release polymer matrix. Each dosage unit may comprise a compressed or molded tablet, wherein each tablet within the capsule provides a different drug release profile. For dosage forms mimicking a twice a day dosing profile, a first tablet releases drug substantially immediately following ingestion of the dosage form, while a second tablet releases drug approximately 3 hours to less than 14 hours following ingestion of the dosage form. For dosage forms mimicking a three times daily dosing profile, a first tablet releases drug substantially immediately following ingestion of the dosage form, a second tablet releases drug approximately 3 hours to less than 10 hours following ingestion of the dosage form, and the third tablet releases drug at least 5 hours to approximately 18 hours following ingestion of the dosage form. It is possible that the dosage form includes more than three tablets. While the dosage form will not generally include more than a third tablet, dosage forms housing more than three tablets can be utilized.

Alternatively, each dosage unit in the capsule may comprise a plurality of drug-containing beads, granules or particles. As is known in the art, drug-containing "beads" refer to beads made with drug and one or more excipients or polymers. Drug-containing beads can be produced by applying drug to an inert support, e.g., inert sugar beads coated with drug or by creating a "core" comprising both drug and one or more excipients. As is also known, drug-containing "granules" and "particles" comprise drug particles that may or may not include one or more additional excipients or polymers. In contrast to drug-containing beads, granules and particles do not contain an inert support. Granules generally comprise drug particles and require further processing. Generally, particles are smaller than granules, and are not further processed. Although beads, granules and particles may be formulated to provide immediate release, beads and granules are generally employed to provide delayed release.

In one embodiment, the compound is formulated for topical administration. Suitable topical dosage forms include lotions, creams, ointments, and gels. A "gel" is a semisolid system containing a dispersion of the active agent, i.e., Nox inhibitor, in a liquid vehicle that is rendered semisolid by the action of a thickening agent or polymeric material dissolved or suspended in the liquid vehicle. The liquid may include a lipophilic component, an aqueous component or both. Some emulsions may be gels or otherwise include a gel component. Some gels, however, are not emulsions because they do not contain a homogenized blend of immiscible components. Methods for preparing lotions, creams, ointments, and gels are well known in the art.

The compounds described herein can be administered adjunctively with other active compounds. These compounds include but are not limited to analgesics, anti-inflammatory drugs, antipyretics, antidepressants, antiepileptics, antihistamines, antimigraine drugs, antimuscarinics, anxioltyics, sedatives, hypnotics, antipsychotics, bronchodilators, anti-asthma drugs, cardiovascular drugs, corticosteroids, dopaminergics, electrolytes, gastro-intestinal drugs, muscle relaxants, nutritional agents, vitamins, parasympathomimetics, stimulants, anorectics and anti-narcoleptics. "Adjunctive administration", as used herein, means the compounds can be administered in the same dosage form or in separate dosage forms with one or more other active agents.

EXPERIMENTAL

Synthesis

The synthetic route chosen to synthesize certain compounds are illustrated below and in FIGS. 1A-D.

General Procedure for the synthesis of the 2,6-Pyridine analogs (2). To a solution of pyridine-2,6-dicarbaldehyde (50 mg, 0.37 mmol) in methanol (2 mL) was added the aniline derivative of choice (0.81 mmol) and $ZnCl_2$ (100 mg, 0.74 mmol). The solution was stirred for two hours at room temperature. $NaBH_3CN$ (46.5 mg, 0.81 mmol) was then added and the solution as stirred overnight. The crude product was purified by column chromatography.

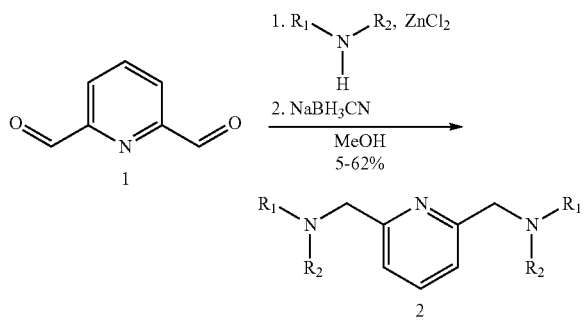

$R_1$ = H and $R_1$ = phenyl (a) 3-flurophenyl (b) 4-flurophenyl (c)
2-Methoxyophenyl (d) 4-methoxyphenyl (e)
3-chlorophenyl (f) 4-chlorophenyl (g) 3-trifluoromethylphenyl (h)
4-trifluoromethylphenyl (i) 3-nitrophenyl (j) 4-nitrophenyl (k)
3-methylphenyl (l) 4-methylphenyl (m) 4-ethylphenyl (n)
4-thiomethylphenyl (o) pyridinyl (p) pyrimidyl (q)
$R_1$ and $R_2$ = piperidyl (r) pyrrolidyl (s) morpholine (t)
$R_1$ = Methyl and $R_2$ = Benzyl (u)

2,6-Bis(2-ethylanilinomethyl)pyridine

The product was obtained in 53% yield as a brown solid. 1H NMR (399.99 MHz, CDCl3): δ ppm 1.31 (t, J=7.45 Hz, 6H), 2.60 (q, J=7.58 Hz, 4H), 4.52 (s, 4H), 6.61 (d, J=7.83 Hz, 2H), 6.73 (t, J=7.33 Hz, 2H), 7.06-7.14 (m, 4H), 7.18-7.25 (m, 2H), 7.58 (t, J=7.71 Hz, 1H); 13C NMR (399.9 MHz, CDCl3): δ ppm 158.17, 145.32, 137.29, 127.89, 127.04, 119.98, 117.43, 110.50, 49.36, 23.98, 12.92. HRMS: m/z [M+H]+ calcd for C23H27N3: 346.2278, found: 346.2276.

2,6-Bis(morpholinylmethyl)pyridine

The product obtained was a white semi-solid in 1% yield. 1H NMR (399.99 MHz, CDCl3): δ ppm 7.73 (1H t), 7.47 (2H d), 5.30 (4H s), 2.60 (8H m), 1.65 (8H m), 1.50 (4H, m); 13C NMR (399.9 MHz, CDCl3): δ ppm 152.75, 137.55, 123.65, 120.96, 60.43, 63.80, 25.68, 25.11, 23.78. HRMS: m/z [M+H]+ calcd for C15H23N3O2: 278.1863, found: 278.1852.

General Procedure for the Preparation of 2,5-dicarbaldehyde Pyridine Analogs (9a-9c)

Figure 1B:
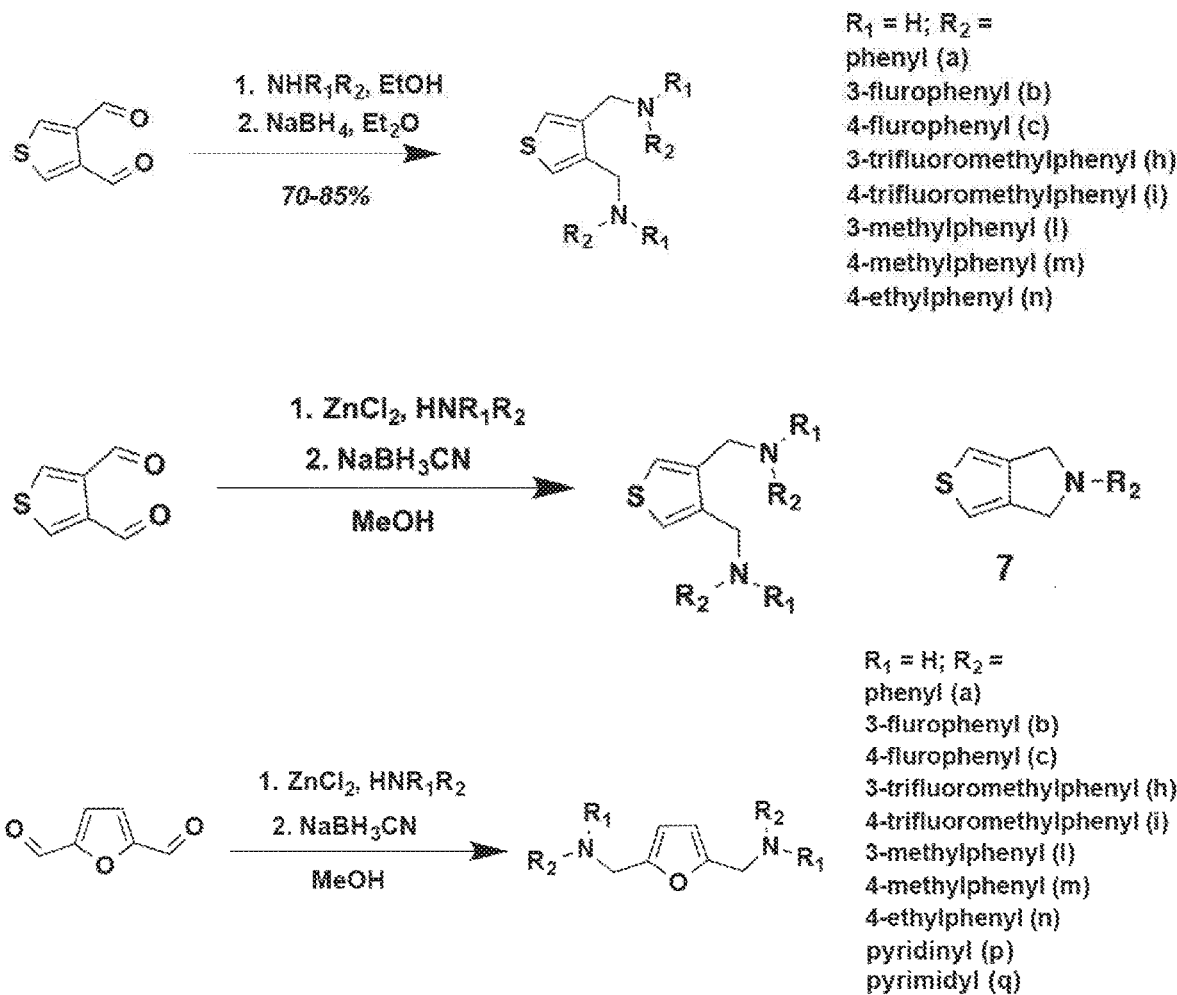
FIG. 1B illustrates the preparation of embodiments of this disclosure.
Figure 1C:
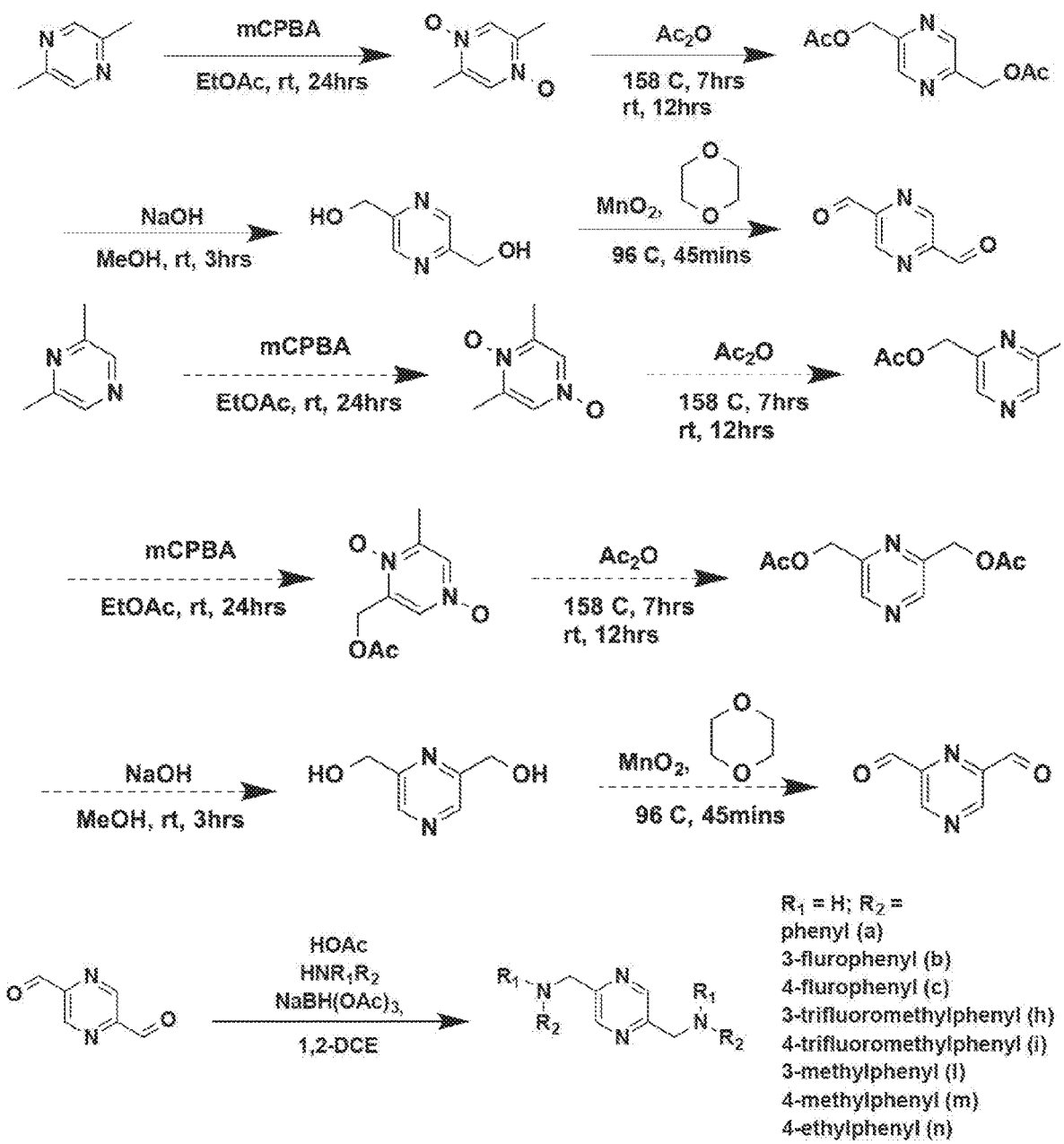
FIG. 1C illustrates the preparation of embodiments of this disclosure.
Figure 1D:
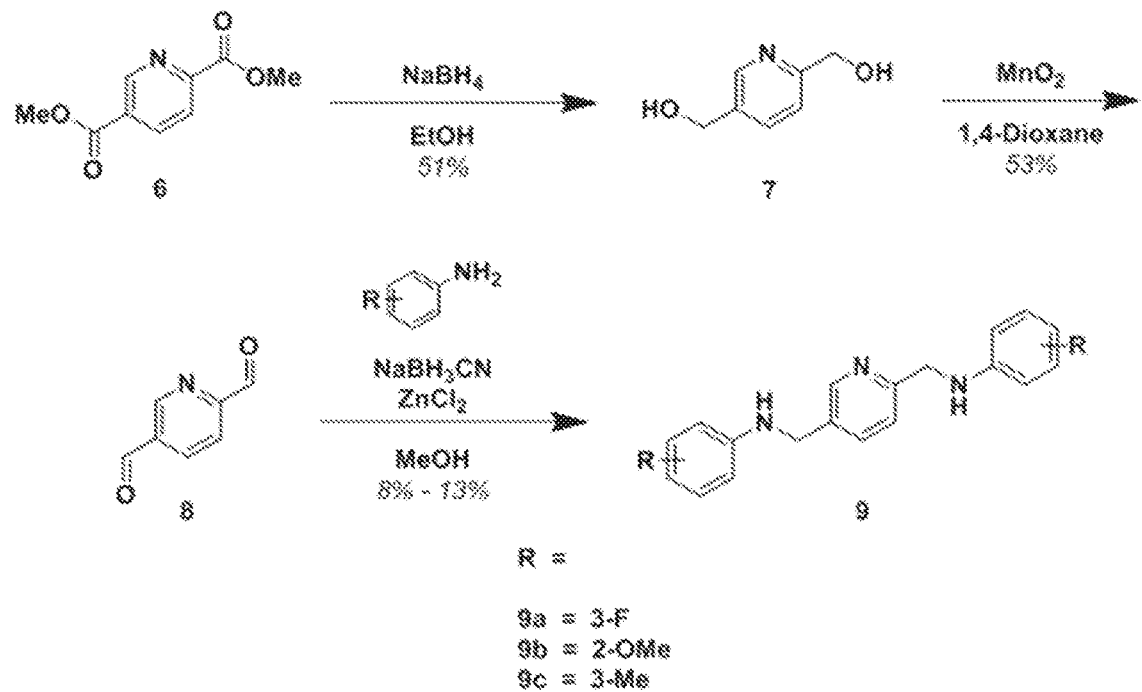
FIG. 1D illustrates the preparation of embodiments of this disclosure.

FIG. 1D illustrates the preparation of 2,5-dicarbaldehyde pyridine analogs. To a stirred solution pyridine-2,5-dicarbaldehyde (1.0 equiv.) in 1,2-dichloroethane (0.27 M) were added an aniline (2.2 equiv.), and sodium triacetoxyborohydride (3.0 equiv.). Acetic acid (2.0 equiv.) was added after five minutes. The reaction was allowed to stir at room temperature for 5 hours and progress followed by TLC. The reaction mixture was quenched with NaOH and extracted with ethyl acetate. The organic layer was dried over MgSO4, filtered and concentrated under reduced pressure. Crude products were purified by column chromatography on silica gel to afford products.

N'-(Pyridine-2,5-diylbis(methylene))bis(4-ethylaniline) (9a)

Product was obtained in 7.8% yield. 1H NMR (399.99 MHz, CDCl3): δ ppm 8.56-8.59 (m, 1H), 7.62-7.67 (m, 2H), 7.37-7.41 (m, 2H), 7.29-7.33 (m, 2H), 6.59 (dd, J=8.34, 13.64 Hz, 4H), 4.43 (s, 1H), 4.32 (s, 1H), 2.54 (q, J=7.60 Hz, 4H), 1.14-1.27 (m, 6H); HRMS: m/z [M+H]+ calcd for C23H28N3: 346.2283, found: 346.2287.

N,N'-(Pyridine-2,5-diylbis(methylene))bis(3-fluoroaniline) (9b)

Product was obtained in 13.41% yield. 1H NMR (399.99 MHz, CDCl3): δ ppm 8.58 (br. s., 1H), 7.58-7.72 (m, 1H), 7.28 (d, J=9.09 Hz, 1H), 7.03-7.14 (m, 2H), 6.25-6.46 (m, 6H), 4.43 (br. s., 2H), 4.33 (br. s., 2H); HRMS: m/z [M+H]+ calcd for C19H18F2N3: 326.1463, found: 326.1453.

N,N'-(Pyridine-2,5-diylbis(methylene))bis(3-methylaniline) (9c)

Product was obtained in 8.37% yield. 1H NMR (399.99 MHz, CDCl3): δ ppm 8.58 (s, 1H), 7.06 (t, J=7.58 Hz, 1H), 6.56 (t, J=7.83 Hz, 1H), 6.41-6.51 (m, 6H), 4.44 (s, 2H), 4.33 (s, 2H), 2.27 (s, 6H); HRMS: m/z [M+H]+ calcd for C21H24N3: 318.1965, found: 318.1965.

2,5-Dicarbaldehyde Pyridine Synthesis pyridine-2,5-diyldimethanol (7)

2,5-dimethyl carboxylate pyridine (1 equiv.) in EtOH was cooled to 0° C. Sodium borohydride (7 equiv.) was added to the cooled 0° C. reaction mixture. The reaction mixture was stirred for 1 hour at 0° C., 3 hours at rt, and refluxed for 12 hours and progress followed by TLC. The reaction was quenched with distilled water. The reaction mixture was then centrifuged and the supernatant was poured off. Silica gel was then added to the supernatant liquid and concentrated under reduced pressure. The silica gel and crude solid was purified by column chromatography (20:1 DCM:MeOH) to afford the 2,5-dimethanol pyridine. Product was obtained in 51.39% yield. HRMS: m/z [M+H]+ calcd for C7H10O2N: 140.0706, found: 140.0703.

4.1.4 Pyridine-2,5-dicarbaldehyde (8)

To a stirred solution 2,5-dimethanol pyridine (1 equiv.) in anhydrous 1,4-dioxane (0.14M) was added dried activated MnO2 (5 equiv.). The reaction mixture was stirred at 96° C. under reflux under nitrogen for 1 hour and progress followed by TLC. The reaction was cooled, quenched with distilled water, filtered, and concentrated under reduced pressure. Crude products were purified by column chromatography (4:1 Hexane:Ethyl acetate) on silica gel to afford 2,5-dicarbaldehyde pyridine. Product was obtained in 52.80% yield. 1H NMR (399.99 MHz, CDCl3): δ ppm 10.24 (s, 1H), 10.18 (s, 1H), 9.26 (s, 1H), 8.36 (d, J=10.10 Hz, 1H), 8.13 (d, J=10.10 Hz, 1H). 13C NMR (399.9 MHz, CDCl3): δ ppm 121.45, 133.25, 137.0, 151.59, 155.32, 189.56, 192.05

Secondary Amines

Methods to prepare symmetrical bis-secondary amine compounds include reductive amination of 1,4-dialdehydes. The reagents used in this preparation are secondary amines like N-alkyl anilines or cyclic amines. As illustrated in FIG. 1A, 1,4-bis(bromomethyl) benzene was used as the starting material, which reacted with corresponding secondary amines in anhydrous acetonitrile in the presence of potassium carbonate, and afforded the target compounds. Similarly, 2,6-bis(chloromethyl) pyridine reacted with amine derivatives in acetonitrile. Benzyl chloride is less active than benzyl bromide. Cesium carbonate was used to shorten the reaction time.

General Procedure for Synthesis of Compounds Ia-p

To a solution of 1,4-bis(bromomethyl)benzene (1 mmol) in anhydrous acetonitrile (10 mL) was added potassium carbonate (3 mmol) and the corresponding secondary amine (2.2 mmol). The reaction mixture was heated at reflux for 3 h. The resulting mixture was diluted with water (20 mL) and extracted with ethyl acetate (15 mL) three times. The combined organic layers were washed with brine, dried over anhydrous sodium sulfate, and concentrated in vacuo. The crude was purified by column chromatography with methanol/dichloromethane (150:1, v/v) to give the title compound as a colorless liquid or a white solid.

1,4-Bis(pyrrolidin-1-ylmethyl)benzene (Ia)

Colorless liquid, yield 95%. 1H NMR (400 MHz, CDCl3) δ 7.27 (s, 4H), 3.59 (s, 4H), 2.48-2.53 (m, 8H), 1.76-1.80 (m, 8H). 13C NMR (100 MHz, CDCl3) δ 137.95, 128.86, 60.54, 54.21, 23.49. HRMS calcd for C16H25N2 245.20123 [M+H]+, found 245.20084.

1,4-Bis(piperidin-1-ylmethyl)benzene (Ib)

White solid, yield 92%, m.p. 84-86° C. 1H NMR (400 MHz, CDCl3) δ 7.25 (s, 4H), 3.45 (s, 4H), 2.37 (s, 8H), 1.54-1.59 (m, 8H), 1.40-1.45 (m, 4H). 13C NMR (100 MHz, CDCl3) δ 137.31, 129.19, 63.87, 54.70, 26.19, 24.61. HRMS calcd for C18H29N2 273.23253 [M+H]+, found 273.23243.

1,4-Bis(morpholinomethyl)benzene (Ic)

White solid, yield 88%, m.p. 113-115° C. 1H NMR (400 MHz, CDCl3) δ 7.27 (s, 4H), 3.70-3.72 (m, 8H), 3.48 (s, 4H), 2.43-2.45 (m, 8H). 13C NMR (100 MHz, CDCl3) δ 136.83, 129.31, 67.20, 63.38, 53.80. HRMS calcd for C16H25O2N2 277.19105 [M+H]+, found 277.19089.

N,N'-(1,4-Phenylenebis(methylene))bis(N-methylaniline) (Id)

White solid, yield 83%, m.p. 77-79° C. 1H NMR (400 MHz, CDCl3) δ 7.18-7.24 (m, 4H), 7.17 (s, 4H), 6.68-6.76 (m, 6H), 4.51 (s, 4H), 3.00 (s, 6H). 13C NMR (100 MHz, CDCl3) δ 149.87, 137.80, 129.32, 127.13, 116.67, 112.51, 56.51, 38.66. HRMS calcd for C22H25N2 317.20123 [M+H]+, found 317.20070.

N,N'-(1,4-phenylenebis(methylene))bis(4-fluoro-N-methylaniline) (Ie)

White solid, yield 80%, m.p. 78-80° C. 1H NMR (400 MHz, CDCl3) δ 7.16 (s, 4H), 6.88-6.95 (m, 4H), 6.63-6.69 (m, 1H), 4.45 (s, 4H), 2.96 (s, 6H). 13C NMR (100 MHz, CDCl3) δ 156.78, 154.44, 146.65, 137.74, 127.26, 115.76, 115.54, 113.82, 113.74, 57.37, 39.23. HRMS calcd for C22H22N2F2 352.17456 [M]+, found 352.17423.

N,N'-(1,4-Phenylenebis(methylene))bis(1-(2-chlorophenyl)-N-methylmethanamine) (If)

Colorless liquid, yield 78%. 1H NMR (400 MHz, CDCl3) δ 7.56 (dd, J=1.5, 0.9 Hz, 1H), 7.54 (dd, J=1.5, 0.9 Hz, 1H), 7.34 (d, J=1.5 Hz, 1H), 7.32 (s, 1H), 7.32 (s, 4H), 7.22-7.26 (m, 2H), 7.14-7.19 (m, 2H), 3.63 (s, 4H), 3.57 (s, 4H), 2.20 (s, 6H). 13C NMR (100 MHz, CDCl3) δ 138.14, 137.14, 134.43, 130.90, 129.58, 129.01, 128.17, 126.80, 62.21, 58.67, 42.46. HRMS calcd for C24H27N2Cl2 413.15458 [M+H]+, found 413.15445.

N,N'-(1,4-Phenylenebis(methylene))bis(1-(3-chlorophenyl)-N-methylmethanamine) (Ig)

Colorless liquid, yield 80%. 1H NMR (400 MHz, CDCl3) δ 7.37 (s, 2H), 7.31 (4, 1H), 7.20-7.25 (m, 6H), 3.52 (s, 4H), 3.48 (s, 4H), 2.18 (s, 6H). 13C NMR (100 MHz, CDCl3) δ 141.73, 137.93, 134.34, 129.67, 129.08, 127.32, 127.17, 110.22, 61.87, 61.38, 42.42. HRMS calcd for C24H27N2Cl2 413.15458 [M+H]+, found 413.15482.

N,N'-(1,4-Phenylenebis(methylene))bis(1-(2-fluorophenyl)-N-methylmethanamine) (Ih)

Colorless liquid, yield 92%. 1H NMR (400 MHz, CDCl3) δ 7.44 (td, J=7.5, 1.9 Hz, 2H), 7.31 (s, 4H), 7.19-7.25 (m, 2H), 7.11 (td, J=7.5, 1.3 Hz, 2H), 6.99-7.04 (m, 2H), 3.59 (s, 3H), 3.54 (s, 3H), 2.20 (s, 6H). 13C NMR (100 MHz, CDCl3) δ 162.79, 160.35, 138.05, 131.52, 131.48, 129.01, 128.72, 128.63, 126.10, 125.95, 124.06, 124.02, 115.47, 115.24, 61.90, 54.30, 42.29. HRMS calcd for C24H27N2F2 381.21368 [M+H]+, found 381.21303.

N,N'-(1,4-Phenylenebis(methylene))bis(1-(3-fluorophenyl)-N-methylmethanamine) (Ii)

Colorless liquid, yield 85%. 1H NMR (400 MHz, CDCl3) δ 7.31 (s, 4H), 7.24-7.29 (m, 2H), 7.09-7.13 (m, 4H), 6.90-6.95 (m, 2H), 3.51 (s, 4H), 3.49 (s, 4H), 2.18 (s, 6H). 13C NMR (100 MHz, CDCl3) δ 164.39, 161.94, 142.49, 142.42, 138.04, 129.80, 129.72, 129.00, 124.50, 124.47, 115.80, 115.59, 114.06, 113.84, 61.86, 61.43, 42.47. HRMS calcd for C24H27N2F2 381.21368 [M+H]+, found 381.21330.

N,N'-(1,4-Phenylenebis(methylene))bis(1-(4-fluorophenyl)-N-methylmethanamine) (Ij)

White solid, yield 81%, mp 80-82° C. 1H NMR (400 MHz, CDCl3) δ 7.28-7.33 (m, 8H), 6.97-7.03 (m, 4H), 3.49 (s, 4H), 3.47 (s, 4H), 2.16 (s, 6H). 13C NMR (100 MHz, CDCl3) δ 163.34, 160.91, 138.11, 135.27, 130.57, 130.49, 129.01, 115.28, 115.07, 61.78, 61.23, 42.37. HRMS calcd for C24H27N2F2 381.21368 [M+H]+, found 381.21343.

N,N'-(1,4-Phenylenebis(methylene))bis(1-(3-methoxyphenyl)-N-methylmethanamine) (Ik)

Colorless liquid, yield 87%. 1H NMR (400 MHz, CDCl3) δ 7.31 (s, 4H), 7.21-7.26 (m, 2H), 6.93-6.95 (m, 4H), 6.79-6.81 (m, 1H), 6.78 (dd, J=2.7, 1.0 Hz, 1H), 3.81 (s, 6H), 3.50 (s, 4H), 3.49 (s, 4H), 2.18 (s, 6H). 13C NMR (101 MHz, CDCl3) δ 159.77, 141.22, 138.05, 129.30, 128.98, 121.41, 114.41, 112.56, 61.98, 61.71, 55.33, 42.49. HRMS calcd for C26H33N2O2 405.25365 [M+H]+, found 405.25331.

N,N'-(1,4-Phenylenebis(methylene))bis(N-benzylethanamine) (Il)

Colorless liquid, yield 78%. 1H NMR (400 MHz, CDCl3) δ 7.36-7.39 (m, 4H), 7.29-7.33 (m, 8H), 7.20-7.24 (m, 2H), 3.57 (s, 4H), 3.55 (s, 4H), 2.50 (q, J=7.1 Hz, 4H), 1.07 (t, J=7.1 Hz, 6H). 13C NMR (100 MHz, CDCl3) δ 140.27, 138.55, 128.93, 128.73, 128.31, 126.86, 57.89, 57.65, 47.24, 12.07. HRMS calcd for C26H33N2 373.26383 [M+H]+, found 373.26385.

N,N'-(1,4-Phenylenebis(methylene))bis(N-benzyl-1-cyclopropylmethanamine) (Im)

Colorless liquid, yield 80%. 1H NMR (400 MHz, CDCl3) δ 7.38-7.41 (m, 4H), 7.32 (s, 4H), 7.28-7.32 (m, 4H), 7.19-7.24 (m, 2H), 3.65 (s, 4H), 3.64 (s, 4H), 2.33 (s, 2H), 2.31 (s, 2H), 0.88-0.97 (m, 2H), 0.43-0.48 (m, 4H), 0.01-0.05 (m, 4H). 13C NMR (100 MHz, CDCl3) δ 140.42, 138.68, 128.89, 128.68, 128.29, 126.83, 58.52, 58.37, 58.16, 8.68, 4.17. HRMS calcd for C30H37N2 425.29513 [M+H]+, found 425.29508.

N,N'-(1,4-Phenylenebis(methylene))bis(N-methyl-1-(pyridin-2-yl)methanamine) (In)

Colorless liquid, yield 82%. 1H NMR (400 MHz, CDCl3) δ 8.54 (dd, J=1.8, 0.9 Hz, 1H), 8.53 (dd, J=1.8, 1.0 Hz, 1H), 7.66 (td, J=7.6, 1.8 Hz, 2H), 7.50-7.52 (m, 2H), 7.33 (s, 4H), 7.13-7.16 (m, 2H), 3.69 (s, 4H), 3.57 (s, 4H), 2.24 (s, 8H). 13C NMR (100 MHz, CDCl3) δ 159.87, 149.09, 137.83, 136.54, 128.99, 123.08, 122.02, 63.56, 61.98, 42.67. HRMS calcd for C22H27N4 347.22302 [M+H]+, found 347.22275.

N,N'-(1,4-Phenylenebis(methylene))bis(N-methyl-1-(pyridin-3-yl)methanamine) (Io)

Colorless liquid, yield 79%. 1H NMR (400 MHz, CDCl3) δ 8.57 (d, 2H), 8.50 (d, J=1.7 Hz, 1H), 8.49 (d, J=1.7 Hz, 1H), 7.71-7.72 (m, 1H), 7.69-7.70 (m, 1H), 7.31 (s, 4H), 7.24-7.28 (m, 2H), 3.53 (s, 4H), 3.52 (s, 4H), 2.19 (s, 6H). 13C NMR (100 MHz, CDCl3) δ 150.42, 148.63, 137.90, 136.78, 134.88, 129.04, 123.55, 61.82, 59.06, 42.40. HRMS calcd for C22H27N4 347.22302 [M+H]+, found 347.22288.

N,N'-(1,4-Phenylenebis(methylene))bis(N-methyl-1-(pyridin-4-yl)methanamine) (Ip)

Colorless liquid, yield 80%. 1H NMR (400 MHz, CDCl3) δ 8.54-8.55 (m, 4H), 7.31-7.33 (m, 8H), 3.53 (s, 4H), 3.51 (s, 4H), 2.20 (s, 6H). 13C NMR (100 MHz, CDCl3) δ 149.80, 149.02, 137.87, 129.01, 123.94, 61.96, 60.72, 42.61. HRMS calcd for C22H27N4 347.22302 [M+H]+, found 347.22290.

General Procedure for Synthesis of Compounds IIa-p

To a solution of 2,6-bis(chloromethyl)pyridine (1 mmol) in anhydrous acetonitrile (10 mL) was added cesium carbonate (3 mmol) and the corresponding secondary amine (2.2 mmol). The reaction mixture was heated at reflux for 5 h. The resulting mixture was diluted with water (20 mL) and extracted with ethyl acetate (15 mL) three times. The combined organic layers were washed with brine, dried over anhydrous sodium sulfate, and concentrated in vacuo. The crude was purified by column chromatography with methanol/dichloromethane (100:1, v/v) to give the title compound as a colorless liquid or a white solid.

2,6-Bis(pyrrolidin-1-ylmethyl)pyridine (IIa)

Colorless liquid, yield 86%. 1H NMR (400 MHz, CDCl3) δ 7.58 (t, J=7.7 Hz, 1H), 7.25 (s, 1H), 7.24 (s, 1H), 3.75 (s, 4H), 2.52-2.58 (m, 8H), 1.73-1.81 (m, 8H). 13C NMR (100 MHz, CDCl3) δ 158.77, 136.89, 121.15, 62.41, 54.43, 23.69. FIRMS calcd for C15H24N3 246.19647 [M+H]+, found 246.19644.

2,6-Bis(piperidin-1-ylmethyl)pyridine (IIb)

Colorless liquid, yield 80%. 1H NMR (400 MHz, CDCl3) δ 7.59 (t, J=7.7 Hz, 1H), 7.29 (s, 1H), 7.27 (s, 1H), 3.60 (s, 4H), 2.42-2.44 (m, 8H), 1.55-1.61 (m, 8H), 1.40-1.46 (m, 4H). 13C NMR (100 MHz, CDCl3) δ 158.71, 136.67, 121.20, 65.57, 54.99, 26.20, 24.52. HRMS calcd for C17H28N3 274.22777 [M+H]+, found 274.22757.

2,6-Bis(morpholinomethyl)pyridine (IIc)

White solid, yield 90%, m.p. 93-95° C. 1H NMR (400 MHz, CDCl3) δ 7.63 (t, J=7.7 Hz, 1H), 7.32 (s, 1H), 7.31 (s, 1H), 3.73 (t, 8H), 3.66 (s, 4H), 2.51 (t, 8H). 13C NMR (100 MHz, CDCl3) δ 157.90, 136.86, 121.56, 67.14, 65.02, 53.92. HRMS calcd for C15H24O2N3 278.18630 [M+H]+, found 278.18562.

N,N'-(Pyridine-2,6-diylbis(methylene))bis(N-methylaniline) (IId)

White solid, yield 75%, m.p. 91-93° C. 1H NMR (400 MHz, CDCl3) δ 7.49 (t, J=7.7 Hz, 1H), 7.20-7.25 (m, 4H), 7.02 (s, 1H), 7.00 (s, 1H), 6.70-6.75 (m, 6H), 4.65 (s, 4H), 3.13 (s, 6H). 13C NMR (100 MHz, CDCl3) δ 159.44, 149.41, 137.61, 129.41, 119.01, 116.82, 112.32, 59.00, 39.24. HRMS calcd for C21H24N3 318.19647 [M+H]+, found 318.19664.

N,N'-(Pyridine-2,6-diylbis(methylene))bis(4-fluoro-N-methylaniline) (IIe)

Colorless liquid, yield 70%. 1H NMR (400 MHz, CDCl3) δ 7.52 (t, J=7.7 Hz, 1H), 7.03 (t, J=0.8 Hz, 1H), 7.01 (t, J=0.8 Hz, 1H), 6.90-6.95 (m, 4H), 6.63-6.66 (m, 4H), 4.59 (s, 4H), 3.08 (s, 6H). 13C NMR (101 MHz, CDCl3) δ 159.34, 156.83, 154.49, 146.14, 137.64, 129.87, 128.55, 119.19, 115.86, 115.64, 113.45, 113.38, 59.63, 39.85. HRMS calcd for C21H22F2N3 354.17763 [M+H]+, found 354.17776.

N,N'-(Pyridine-2,6-diylbis(methylene))bis(1-(2-chlorophenyl)-N-methylmethanamine) (IIf)

Colorless liquid, yield 80%. 1H NMR (400 MHz, CDCl3) δ 7.63 (t, J=7.7 Hz, 1H), 7.57 (d, J=1.8 Hz, 1H), 7.55 (d, J=1.8 Hz, 1H), 7.42 (s, 1H), 7.40 (s, 1H), 7.34 (d, J=1.5 Hz, 1H), 7.33 (d, J=1.5 Hz, 1H), 7.15-7.25 (m, 4H), 3.77 (s, 4H), 3.72 (s, 4H), 2.29 (s, 6H). 13C NMR (100 MHz, CDCl3) δ 158.88, 137.10, 136.75, 134.51, 130.97, 129.63, 128.32, 126.79, 121.33, 63.86, 58.85, 42.77. FIRMS calcd for C23H26N3Cl2 414.14983 [M+H]+, found 414.14968.

N,N'-(Pyridine-2,6-diylbis(methylene))bis(1-(3-chlorophenyl)-N-methylmethanamine) (IIg)

Colorless liquid, yield 77%. 1H NMR (399 MHz, CDCl3) δ 7.68 (t, J=7.7 Hz, 1H), 7.39-7.41 (m, 4H), 7.20-7.25 (m, 6H), 3.70 (s, 4H), 3.55 (s, 4H), 2.24 (s, 6H). 13C NMR (100 MHz, CDCl3) δ 158.91, 141.55, 137.11, 134.34, 129.65, 129.08, 127.34, 127.16, 121.27, 63.69, 61.60, 42.76. HRMS calcd for C23H26N2Cl2 414.14983 [M+H]+, found 414.14902.

N,N'-(Pyridine-2,6-diylbis(methylene))bis(1-(2-fluorophenyl)-N-methylmethanamine) (IIh)

Colorless liquid, yield 79%. 1H NMR (400 MHz, CDCl3) δ 7.65 (t, J=7.7 Hz, 1H), 7.45 (td, J=7.5, 1.9 Hz, 2H), 7.41 (s, 1H), 7.39 (s, 1H), 7.20-7.25 (m, 2H), 7.10 (td, J=7.5, 1.3 Hz, 2H), 6.99-7.04 (m, 2H), 3.73 (s, 4H), 3.66 (s, 4H), 2.26 (s, 6H). 13C NMR (100 MHz, CDCl3) δ 162.76, 160.31, 158.86, 136.98, 131.57, 131.53, 128.81, 128.73, 125.67, 125.52, 123.98, 123.94, 121.21, 115.46, 115.24, 63.59, 54.60, 54.58, 42.47. HRMS calcd for C23H26N3F2 382.20893 [M+H]+, found 382.20767.

N,N'-(Pyridine-2,6-diylbis(methylene))bis(1-(3-fluorophenyl)-N-methylmethanamine) (IIi)

Colorless liquid, yield 80%. 1H NMR (400 MHz, CDCl3) δ 7.68 (t, J=7.7 Hz, 1H), 7.42 (s, 1H), 7.40 (s, 1H), 7.23-7.29 (m, 2H), 7.13-7.15 (m, 2H), 7.11-7.12 (m, 2H), 6.90-6.95 (m, 2H), 3.70 (s, 4H), 3.57 (s, 4H), 2.25 (s, 6H). 13C NMR (100 MHz, CDCl3) δ 164.31, 161.87, 158.89, 142.10, 142.03, 137.07, 129.77, 129.69, 124.49, 124.47, 121.17, 115.78, 115.56, 114.08, 113.87, 63.58, 61.59, 61.58, 42.68. HRMS calcd for C23H26N3F2 382.20893 [M+H]+, found 382.20915.

N,N'-(Pyridine-2,6-diylbis(methylene))bis(1-(4-fluorophenyl)-N-methylmethanamine) (IIj)

Colorless liquid, yield 77%. 1H NMR (400 MHz, CDCl3) δ 7.66 (t, J=7.7 Hz, 1H), 7.39 (s, 1H), 7.37 (s, 1H), 7.30-7.35 (m, 4H), 6.96-7.02 (m, 4H), 3.68 (s, 4H), 3.54 (s, 4H), 2.22 (s, 6H). 13C NMR (100 MHz, CDCl3) δ 163.28, 160.84, 158.94, 136.96, 134.86, 134.83, 130.55, 130.47, 121.14, 115.21, 115.00, 63.44, 61.34, 42.54. FIRMS calcd for C23H26N3F2 382.20893 [M+H]+, found 382.20773.

N,N'-(Pyridine-2,6-diylbis(methylene))bis(1-(3-methoxyphenyl)-N-methylmethanamine) (IIk)

Colorless liquid, yield 90%. 1H NMR (400 MHz, CDCl3) δ 7.65 (dd, J=7.9, 7.4 Hz, 1H), 7.42 (s, 1H), 7.40 (s, 1H), 7.20-7.24 (m, 2H), 6.94-6.97 (m, 4H), 6.80 (dd, J=2.7, 1.4 Hz, 1H), 6.78 (dd, J=2.7, 1.4 Hz, 1H), 3.81 (s, 6H), 3.69 (s, 4H), 3.56 (s, 4H), 2.25 (s, 6H). 13C NMR (100 MHz, CDCl3) δ 159.79, 159.13, 141.01, 137.03, 129.35, 121.45, 121.14, 114.49, 112.61, 63.63, 62.24, 55.38, 42.81. HRMS calcd for C25H32N3O2 406.24890 [M+H]+, found 406.24852.

N,N'-(Pyridine-2,6-diylbis(methylene))bis(N-benzylethanamine) (IIl)

Colorless liquid, yield 86%. 1H NMR (400 MHz, CDCl3) δ 7.62 (t, J=7.7 Hz, 1H), 7.44 (s, 1H), 7.42 (s, 1H), 7.36-7.39 (m, 4H), 7.26-7.32 (m, 4H), 7.19-7.23 (m, 2H), 3.72 (s, 4H), 3.62 (s, 4H), 2.55 (q, J=7.1 Hz, 4H), 1.08 (t, J=7.1 Hz, 6H). 13C NMR (100 MHz, CDCl3) δ 159.75, 139.86, 136.84, 128.88, 128.28, 126.89, 120.61, 59.87, 58.16, 47.80, 12.15. HRMS calcd for C25H32N3 374.25907 [M+H]+, found 374.25907.

N,N'-(Pyridine-2,6-diylbis(methylene))bis(N-benzyl-1-cyclopropylmethanamine) (IIm)

Colorless liquid, yield 72%. 1H NMR (400 MHz, CDCl3) δ 7.64 (dd, J=8.1, 7.2 Hz, 1H), 7.50 (s, 1H), 7.48 (s, 1H), 7.40-7.42 (m, 4H), 7.28-7.33 (m, 4H), 7.20-7.24 (m, 2H), 3.84 (s, 4H), 3.71 (s, 4H), 2.40 (s, 2H), 2.38 (s, 2H), 0.89-0.99 (m, 2H), 0.43-0.48 (m, 4H), 0.01-0.07 (m, 4H). 13C NMR (100 MHz, CDCl3) δ 159.88, 140.08, 136.85, 128.88, 128.33, 126.92, 120.66, 60.34, 59.01, 58.71, 8.72, 4.15. HRMS calcd for C29H36N3 426.29037 [M+H]+, found 426.28990.

N,N'-(Pyridine-2,6-diylbis(methylene))bis(N-methyl-1-(pyridin-2-yl)methanamine) (IIn)

Colorless liquid, yield 75%. 1H NMR (400 MHz, CDCl3) δ 8.51 (dd, J=1.8, 0.9 Hz, 1H), 8.50 (dd, J=1.8, 0.9 Hz, 1H), 7.64 (d, J=1.7 Hz, 1H), 7.62 (d, J=1.7 Hz, 1H), 7.60 (d, J=1.7 Hz, 1H), 7.49 (t, J=7.8, 1.1 Hz, 1H), 7.47 (t, J=7.8, 1.1 Hz, 1H), 7.38 (s, 1H), 7.36 (s, 1H), 7.13 (dd, J=4.9, 1.2 Hz, 1H), 7.11 (dd, J=4.9, 1.2 Hz, 1H), 3.74 (s, 4H), 3.73 (s, 4H), 2.27 (s, 6H). 13C NMR (100 MHz, CDCl3) δ 159.31, 158.63, 149.17, 137.03, 136.60, 123.23, 122.15, 121.41, 63.70, 63.63, 42.83. HRMS calcd for C21H26N5 348.21827 [M+H]+, found 348.21800. 4.1.3.15.

N,N'-(Pyridine-2,6-diylbis(methylene))bis(N-methyl-1-(pyridin-3-yl)methanamine) (IIo)

Colorless liquid, yield 74%. 1H NMR (400 MHz, CDCl3) δ 8.59 (d, J=0.8 Hz, 1H), 8.59 (d, J=0.8 Hz, 1H), 8.50 (d, J=1.7 Hz, 1H), 8.49 (d, J=1.7 Hz, 1H), 7.72 (t, J=2.0 Hz, 1H), 7.70 (t, J=2.0 Hz, 1H), 7.67 (t, J=7.7 Hz, 1H), 7.40 (s, 1H), 7.38 (s, 1H), 7.28-7.23 (m, 2H), 3.71 (s, 4H), 3.59 (s, 4H), 2.25 (s, 6H). 13C NMR (100 MHz, CDCl3) δ 158.80, 150.56, 148.73, 137.16, 136.75, 134.61, 123.48, 121.34, 63.60, 59.38, 42.70. HRMS calcd for C21H26N5 348.21827 [M+H]+, found 348.21814.

N,N'-(Pyridine-2,6-diylbis(methylene))bis(N-methyl-1-(pyridin-4-yl)methanamine) (IIp)

Colorless liquid, yield 81%. 1H NMR (400 MHz, CDCl3) δ 8.53-8.55 (m, 4H), 7.69 (t, J=7.7 Hz, 1H), 7.42 (s, 1H), 7.40 (s, 1H), 7.32-7.34 (m, 4H), 3.71 (s, 4H), 3.59 (s, 4H), 2.27 (s, 6H). 13C NMR (100 MHz, CDCl3) δ 158.70, 149.88, 148.62, 137.25, 123.92, 121.35, 63.72, 60.97, 42.91. HRMS calcd for C21H26N5 348.21827 [M+H]+, found 348.21813.

Primary Binding Affinity Screening

The compounds were initially screened with a binding affinity assay. This assay involves competition of a potent CXCR4 peptidic inhibitor, TN14003, with the test compound. MDA-MB-231 cells were pre-incubated with compounds at concentrations of 1, 10, 100, and 1000 nM, then incubated with biotinylated TN14003 and streptavidin-conjugated rhodamine to determine the binding efficiency of the new compounds to the CXCL12 binding domain of CXCR4. The effective concentration (EC) is defined as the lowest concentration at which a significant reduction in the rhodamine fluorescent color is observed as compared to the control reflecting the competitive displacement by peptide TN14003. Thus, this screening is a semi-quantitative, first pass measure of the level of activity. Nineteen compounds exhibited moderate to good activity (<1000 nM) in blocking the binding of peptide TN14003 to CXCR4. Ten substances displayed potent binding affinity, with EC values from 1 to 100 nM. They were all comparatively more effective than AMD3100 (1000 nM).

TABLE 1

Data for the binding affinity assay.

| Compd | EC (nM) |
|---|---|
| Ia | 1000 |
| Ib | 10 |
| Ic | >1000 |
| Id | 1000 |
| Ie | 100 |
| If | >1000 |
| Ig | 1000 |
| Ih | >1000 |
| AMD3100 | 1000 |
| Ii | >1000 |
| Ij | >1000 |
| Ik | 10 |
| Il | 1000 |
| Im | 1000 |
| In | >1000 |
| Io | >1000 |
| Ip | >1000 |
| IIa | 1 |
| IIb | 1 |
| IIc | 100 |
| IId | 1000 |
| IIe | 1000 |
| IIf | >1000 |
| IIg | 10 |
| IIh | 1000 |
| IIi | >1000 |
| IIj | 1000 |
| IIk | 10 |
| Il | >1000 |
| IIm | 1 |
| IIn | 10 |
| IIo | >1000 |
| IIp | >1000 |

For binding affinity assay, $2 \times 10^4$ MDA-MB-231 cells in 300 μL of cell culture medium were seeded in an 8-well slide chamber 2 days before the experiments were conducted. Various concentrations of different compounds (1, 10, 100, or 1000 nM) were added to the separate wells and incubated for 10 min at room temperature, and then the cells were fixed in 4% ice-cold paraformaldehyde. The cells were rehydrated in phosphate-buffered saline (PBS). The slides were subsequently incubated for 30 min at room temperature with 0.05 μg/mL biotinylated TN14003, washed three times with PBS, and incubated in streptavidin-rhodamine (1:150 dilution; Jackson ImmunoResearch Laboratories, West Grove, Pa.) for 30 min at room temperature. Finally, the slides were washed with PBS and mounted in an anti-fade mounting solution (Molecular Probes, Eugene, Oreg.), and the samples were analyzed on a Nikon Eclipse E800 microscope.

Matrigel® Invasion Assay

Figure 2:
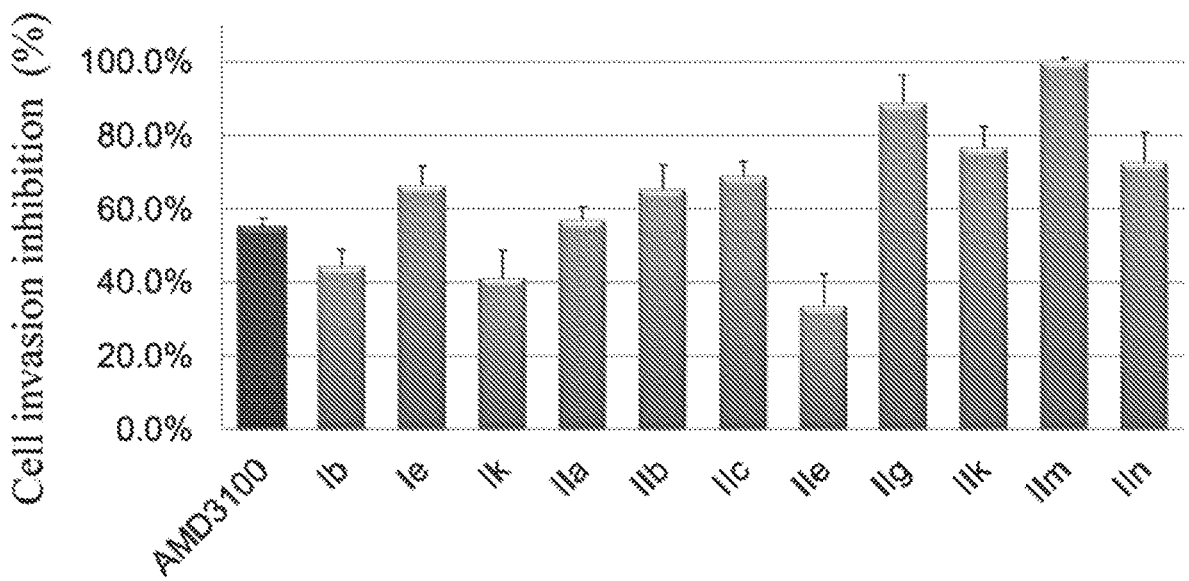
FIG. 2 shows data in a Matrigel® invasion inhibition assay of AMD3100 and compounds disclosed herein.

To model in vitro metastasis, a Matrigel® invasion assay was used as the functional assay. This assay was performed for those compounds with an EC value lower than 1000 nM in the binding affinity assay to test whether they could block the CXCR4/CXCL12-mediated chemotaxis and invasion at a single concentration of 100 nM. The compounds and cells were added to the upper chamber and CXCL12 was added to the lower chamber as a chemoattractant. A layer of Matrigel® matrix-coated permeable support (8 μm pore diameter) separates the upper and lower chambers. If the compounds demonstrate a strong CXCR4 inhibitory effect, fewer cells are able to move through the Matrigel®. The results of Matrigel® invasion are summarized in FIG. 2. Ib, Ik and IIe exhibited an inhibitory rate below 50%. The potency of Ie (66.4%), IIb (65.3%), IIc (68.9%), IIg (88.6%), IIk (76.7%), IIm (100%) and IIn (72.6%) was superior to the reference drug AMD3100 (62.0%).

TABLE 2

Data for compounds in an invasion assay.

| Compound | R1 | R2 | EC (nm) | Invasion Assay |
|---|---|---|---|---|
| 2,5-pyridine | H | 3-F Phenyl | 10 | 50% |
| 2,5-pyridine | H | 3-Me Phenyl | 100 | 60.2% |
| 2,5-pyridine | H | 4-Et Phenyl | 1 | 64% |
| 2,5-pyridine | H | 4-CF3 Phenyl | 1 | 52.1% |
| 2,5-pyridine | H | Morpholine | 10 | 63.3% |
| 3,4-thiophene | H | Phenyl | 10 | 72% |
| 7c | | 4-F Phenyl | 1 | 65.6% |
| 2,5-pyrazine | H | 4-F Phenyl | 100 | 76% |
| 2,5-furan | H | 4-F Phenyl | 100 | 53.2% |
| 2,5-furan | H | 4-Me Phenyl | 100 | 74.8% |

For compound 7c see FIG. 1B.

In Vivo Suppression Against Carrageenan-Induced Paw Edema

CXCR4 plays a role in the recruitment of inflammatory cells to sites of inflammation. Blocking CXCR4 is a therapeutic strategy in inflammatory diseases. A carrageenan-induced mouse paw edema model as an efficient model to evaluate the in vivo CXCR4 antagonistic activity for CXCR4 inhibitors.

Acute inflammation was induced by subcutaneous injection of 50 μL of λ-carrageenan (1% w/v in saline) into one of the hind paws of the female C57BL/6J mice (Jackson Laboratories); the other hind paw was injected with 50 μL of saline, which was used as a non-inflammation control. The selected compounds were dissolved in 10% DMSO and 90% of 45% (2-hydroxypropyl)-β-cyclodextrin (CD) in PBS. In the treatment group, compounds IIg, IIk, IIm and IIn were administered intraperitoneally (i.p.) at 10 mg/kg daily, while TN14003 was administered at 300 μg/kg, i.p., daily, 30 min following carrageenan challenge. The rationale for using 300 μg/kg for TN14003 was that this concentration was reported to be the minimum concentration needed to achieve the maximum efficacy of this compound in a breast cancer metastasis animal model. See Yoon et al. CXC chemokine receptor-4 antagonist blocks both growth of primary tumor and metastasis of head and neck cancer in xenograft mouse models. Cancer Res., 67 (2007), pp. 7518-7524. Control animals received corresponding i.p. injections of the vehicle. The animals were sacrificed 74 h after carrageenan challenge and 2 h after the last injection of the selected compounds. The final paws were photographed and measured for thickness from the "palm" to the back of the paw with a caliper. These were compared to the volume of carrageenan-untreated contralateral paw to obtain the edema volume; the volume of the contralateral paw was subtracted from the volume of the carrageenan injected paw to obtain the edema volume. The inflammation-suppression percentage was calculated by comparing the drug-treated group to the control group.

On the basis of the in vitro assay results, compounds (IIg, IIk, IIm and IIn) were investigated. Because of the in vivo toxicity of AMD3100, TN14003 was used as the reference drug for our animal experiments. Substances IIg and IIm demonstrated excellent CXCR4 antagonistic activity and in vivo potency of <20%. Compound IIk exhibited inhibition (31.0%). IIn showed a 50% inhibitory effect on inflammation, which was comparable to TN14003 (48%). After being treated with IIn, the inflammation induced in the left paw was clearly suppressed. The normal mouse paw tissue exhibits a dermis tightly connected to the epidermis through a basement membrane, and the papillary region is composed of loose areolar connective tissue (A1-3). However, the carrageenan-induced inflammatory tissue showed intense dermal papillae edema, and a dense infiltration of inflammatory cells (B1-3). Compound IIn significantly attenuated the mouse paw inflammation and damage in histological assay. Both the edema volume and the number of inflammatory cells decreased observably (C1-3). These data confirm that this selected anti-CXCR4 candidate can inhibit inflammation as anticipated. Since compound IIn, which possesses a pyridine pharmacophore, had the best suppression effect in vivo, the terminal ring we modified and compounds Io, Ip, IIo and IIp, bearing a nitrogen atom at the 3' or 4' position, were synthesized. These compounds exhibited poor ECs in the binding affinity assay (>1000 nM).

TABLE 3

Data for certain compounds

| Compound | EC (nM) | Invasion[a] | Carageenan[b] |
|---|---|---|---|
| 2,6-Bis(2-ethylanilinomethyl)pyridine | 1 | 59% | 18.1% |
| 2,6-Bis(4-ethylanilinomethyl)pyridine | 1 | 64% | 42.0% |
| 2,6-Bis(3-fluoroanilinomethyl)pyridine | 10 | 50% | 20.3% |
| 2,6-Bis(3-methoxyanilinomethyl)pyridine | 100 | 37% | 20.1% |
| 2,6-Bis(4-trifluoromethylanilinomethyl)pyridine | 1 | 52% | 20.3% |
| 2,6-Bis(morpholinylmethyl)pyridine | 10 | 63% | 39.1% |
| N,N'-(Pyridine-2,5-diylbis(methylene))bis(3-methylaniline) | 1 | 58% | — |
| AMD3100 | 1000 | 62% | — |
| WZ811 | 10 | 90% | 40% |

[a]The concentration used in the invasion assay was 100 nM.
[b]Mice were dosed used 10 mg of compound for every kg the mouse weighed.

The invention claimed is:

1. A pharmaceutical composition in the form of a tablet or capsule comprising a compound of Formula IL

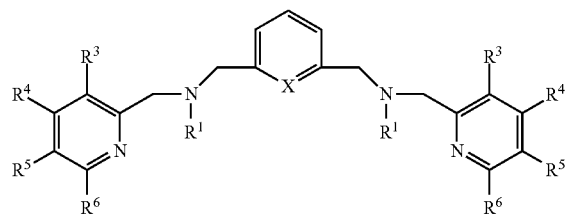

Formula IL wherein,

X is N or CH;

$R^1$ is alkyl optionally substituted with one or more, the same or different, $R^{10}$;

$R^3$, $R^4$, $R^5$, $R^6$, and $R^7$, are each individually and independently selected from hydrogen, alkyl, halogen, nitro, cyano, hydroxy, amino, mercapto, formyl, carboxy, carbamoyl, alkoxy, hydroxyalkyl, alkylthio, thioalkyl, alkylamino, aminoalkyl, (alkyl)$_2$amino, alkanoyl, alkoxycarbonyl, alkylsulfinyl, alkyl sulfonyl, aryl sulfonyl, carbocyclyl, benzoyl, benzyl, aryl, or heterocyclyl, wherein $R^3$, $R^4$, $R^5$, $R^6$, and $R^7$ are optionally substituted with one or more, the same or different, $R^{10}$; and $R^{10}$ is alkyl, halogen, nitro, cyano, hydroxy, amino, mercapto, formyl, carboxy, carbamoyl, alkoxy, hydroxyalkyl, alkylthio, thioalkyl, alkylamino, aminoalkyl, (alkyl)$_2$amino, alkanoyl, alkoxycarbonyl, alkylsulfinyl, alkyl sulfonyl, aryl sulfonyl, carbocyclyl, benzoyl, benzyl, aryl, or heterocyclyl, wherein $R^{10}$ is optionally substituted with one or more, the same or different, $R^{11}$; and $R^{11}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, isopropoxy, tert-butoxy, hydoxymethyl, hydroxyethyl, thiomethyl, thioethyl, aminomethyl, aminoethyl, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methyl sulfinyl, ethylsulfinyl, mesyl, ethyl sulfonyl, methoxycarbonyl, ethoxycarbonyl, isopropoxycarbonyl, tert-butoxycarbonyl, N-methyl sulfamoyl, N-ethyl sulfamoyl, N,N-dimethylsulfamoyl, N,N-diethylsulfamoyl, N-methyl-N-ethylsulfamoyl, benzoyl, benzyl, carbocyclyl, aryl, or heterocyclyl, or salt, ester, amide thereof and a pharmaceutically acceptable excipient.

2. The pharmaceutical composition of claim 1 further comprising another active ingredient.

3. The pharmaceutical composition of claim 1 further comprising another anti-cancer agent.

4. The pharmaceutical composition of claim 1 wherein the pharmaceutically acceptable excipient is selected from cellulose, cellulose acetate phthalate, hydroxypropyl cellulose, hydroxypropyl methylcellulose, hydroxypropyl methylcellulose phthalate, and hydroxypropyl methylcellulose acetate succinate.

5. The pharmaceutical composition of claim 1 wherein the pharmaceutically acceptable excipient is selected from dicalcium phosphate dihydrate, calcium sulfate dioxide, titanium oxide, and magnesium aluminum silicate.

6. The pharmaceutical composition of claim 1 wherein the pharmaceutically acceptable excipient is selected from gelatin, sucrose, glucose, dextrose, lactose, sorbitol, mannitol, and polyethylene glycol.

7. The pharmaceutical composition of claim 1 wherein the pharmaceutically acceptable excipient is selected from magnesium stearate, calcium stearate, stearic acid, and glycerol behenate.

8. A pharmaceutical composition in the form of a tablet or capsule comprising N,N'-(pyridine-2,6-diylbis(methylene)) bis(N-methyl-1-(pyridin-2-yl)methanamine) or salt thereof and a pharmaceutically acceptable excipient.

9. The pharmaceutical composition of claim 8 further comprising another anti-cancer agent.

10. The pharmaceutical composition of claim 8 wherein the pharmaceutically acceptable excipient is selected from cellulose, cellulose acetate phthalate, hydroxypropyl cellulose, hydroxypropyl methylcellulose, hydroxypropyl methylcellulose phthalate, and hydroxypropyl methylcellulose acetate succinate.

11. The pharmaceutical composition of claim 8 wherein the pharmaceutically acceptable excipient is selected from dicalcium phosphate dihydrate, calcium sulfate dioxide, titanium oxide, and magnesium aluminum silicate.

12. The pharmaceutical composition of claim 8 wherein the pharmaceutically acceptable excipient is selected from gelatin, sucrose, glucose, dextrose, lactose, sorbitol, mannitol, and polyethylene glycol.

13. The pharmaceutical composition of claim 8 wherein the pharmaceutically acceptable excipient is selected from magnesium stearate, calcium stearate, stearic acid, and glycerol behenate.

* * * * *